(12) United States Patent
Anding et al.

(10) Patent No.: US 12,295,627 B2
(45) Date of Patent: May 13, 2025

(54) STABILIZATION SYSTEMS

(71) Applicant: GLOBUS MEDICAL, INC., Audubon, PA (US)

(72) Inventors: Donald Anding, Philadelphia, PA (US); Andrew Davison, Downingtown, PA (US); James Gault, Philadelphia, PA (US); Alex Bada, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/816,834

(22) Filed: Aug. 2, 2022

(65) Prior Publication Data
US 2023/0044693 A1    Feb. 9, 2023

Related U.S. Application Data

(63) Continuation of application No. 16/030,895, filed on Jul. 10, 2018, now Pat. No. 11,432,857, which is a continuation-in-part of application No. 15/893,774, filed on Feb. 12, 2018, now Pat. No. 11,197,701, which is a continuation-in-part of application No. 15/405,368, filed on Jan. 13, 2017, now Pat. No. 10,751,098, which is a continuation-in-part of application No. 15/238,772, filed on Aug. 17, 2016, now Pat. No. 10,687,873.

(51) Int. Cl.
*A61B 17/80* (2006.01)
*A61B 17/84* (2006.01)
*A61B 17/86* (2006.01)

(52) U.S. Cl.
CPC .......... *A61B 17/8057* (2013.01); *A61B 17/80* (2013.01); *A61B 17/8014* (2013.01); *A61B 17/8042* (2013.01); *A61B 17/8052* (2013.01); *A61B 17/8085* (2013.01); *A61B 17/809* (2013.01); *A61B 17/848* (2013.01); *A61B 17/8605* (2013.01)

(58) Field of Classification Search
CPC .... A61B 17/809; A61B 17/8085; A61B 17/80
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,463,148 | A | 8/1969 | Treace |
| 3,695,259 | A | 10/1972 | Yost |
| 3,716,050 | A | 2/1973 | Johnston |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — David W Bates

(57) ABSTRACT

Devices, systems, and methods of bone stabilization. The bone stabilization system includes a variety of plates, including a tine plate. The tine plate may include an elongate body and first and second ears extending from the elongate body, each of the first and second ears defining a screw hole therethrough, and a first tine extending from the first ear and a second tine extending from the second ear, the first and second tines each terminating at a sharp point.

19 Claims, 43 Drawing Sheets

(56) References Cited

U.S. PATENT DOCUMENTS

| | | |
|---|---|---|
| 4,219,015 A | 8/1980 | Steinemann |
| 4,493,317 A | 1/1985 | Klaue |
| 4,513,744 A | 4/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,921,986 A | 7/1999 | Bonutti |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,335,204 B2 * | 2/2008 | Tornier ............ A61B 17/8061 606/280 |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 * | 2/2012 | Leither ............ A61B 17/8014 606/283 |
| 8,118,848 B2 * | 2/2012 | Ducharme ........ A61B 17/8061 606/291 |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,535,355 B2 * | 9/2013 | Prasad ............ A61B 17/8061 606/291 |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |

(56) References Cited

U.S. PATENT DOCUMENTS

| | | |
|---|---|---|
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| D840,035 S * | 2/2019 | Weiner .......... D24/155 |
| 2002/0045901 A1 | 4/2002 | Wagner et al. |
| 2003/0199875 A1* | 10/2003 | Mingozzi .......... A61B 17/8095 606/297 |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2005/0261688 A1 | 11/2005 | Grady et al. |
| 2006/0122607 A1* | 6/2006 | Kolb .......... A61B 17/1728 606/283 |
| 2006/0149265 A1 | 7/2006 | James et al. |
| 2006/0173459 A1* | 8/2006 | Kay .......... A61B 17/8061 606/280 |
| 2006/0241607 A1 | 10/2006 | Myerson et al. |
| 2007/0043366 A1* | 2/2007 | Pfefferle .......... A61B 17/8052 606/279 |
| 2007/0073298 A1* | 3/2007 | Beutter .......... A61B 17/80 606/301 |
| 2007/0173840 A1 | 7/2007 | Huebner |
| 2007/0185493 A1* | 8/2007 | Feibel .......... A61B 17/8061 606/71 |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234677 A1 | 9/2008 | Dahners et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0054930 A1* | 2/2009 | Aflatoon .......... A61B 17/7059 606/246 |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0123484 A1 | 5/2012 | Lietz et al. |
| 2012/0203227 A1 | 8/2012 | Martin |
| 2012/0232599 A1 | 9/2012 | Schoenly et al. |
| 2012/0265255 A1 | 10/2012 | Hilse et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0096630 A1 | 4/2013 | Lee et al. |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |

(56) References Cited

U.S. PATENT DOCUMENTS

| | | |
|---|---|---|
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0164990 A1* | 6/2017 | Weiner ............... A61B 17/8014 |
| 2017/0215931 A1* | 8/2017 | Cremer ............. A61B 17/8052 |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| JP | 1190348 A | 7/1989 |
| JP | H01190348 A | 7/1989 |
| JP | 2003210478 A | 7/2003 |
| JP | 2004529710 A | 9/2004 |
| JP | 2007151674 A | 6/2007 |
| JP | 2007289698 A | 11/2007 |
| JP | 2008500143 A | 1/2008 |
| JP | 2008-505700 A | 2/2008 |
| JP | 2010-522019 A | 7/2010 |
| JP | 2013-521046 A | 6/2013 |
| JP | 2016530001 A | 9/2016 |
| TW | 201316942 A | 5/2013 |
| WO | 2011109127 A1 | 9/2011 |
| WO | 2016079504 A1 | 5/2016 |
| WO | 2016134775 A1 | 9/2016 |

\* cited by examiner

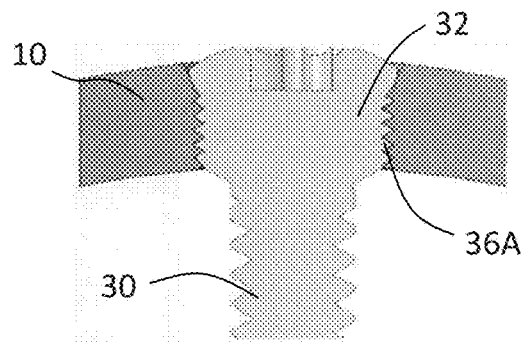
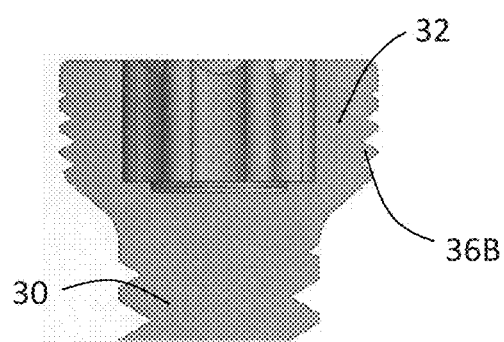
FIG. 19A  FIG. 19B
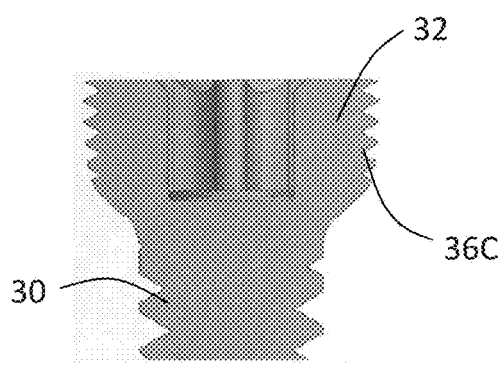
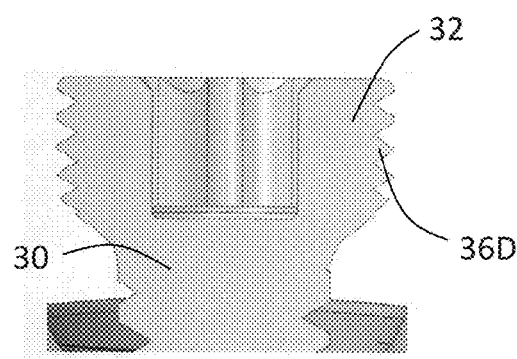
FIG. 19C  FIG. 19D
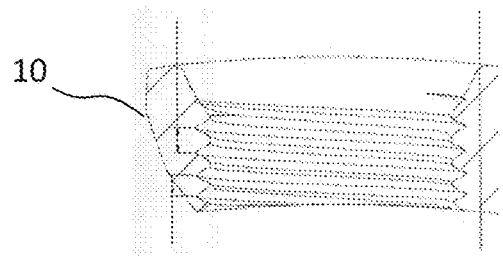
FIG. 19E

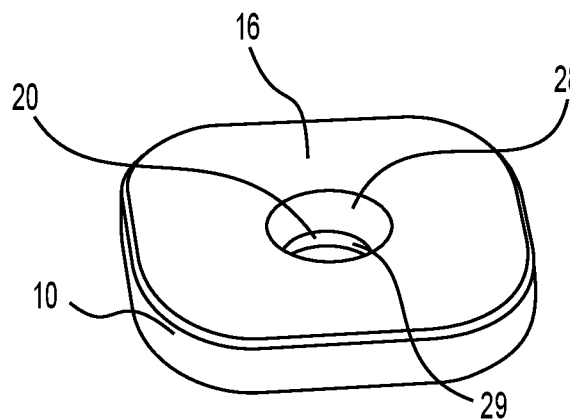
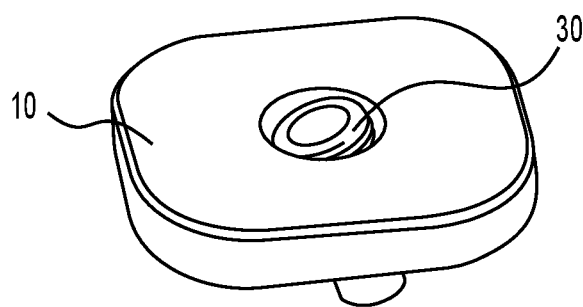
FIG. 26A  FIG. 26B
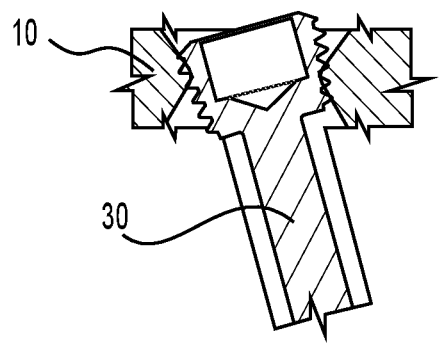
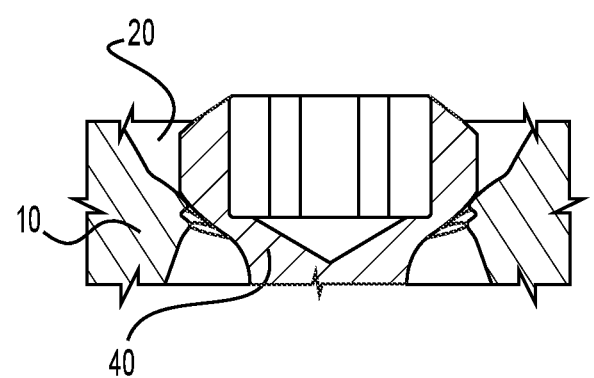
FIG. 26C  FIG. 26D

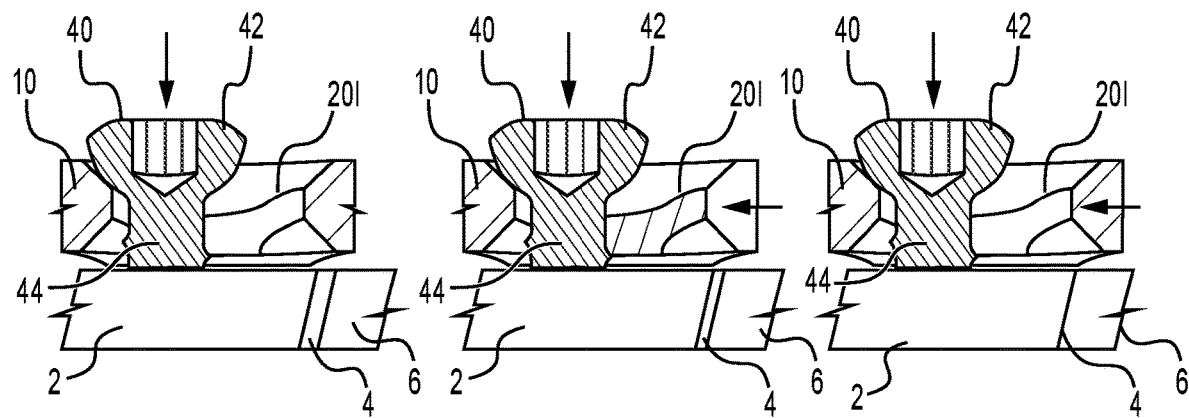
*FIG. 27A*  *FIG. 27B*  *FIG. 27C*
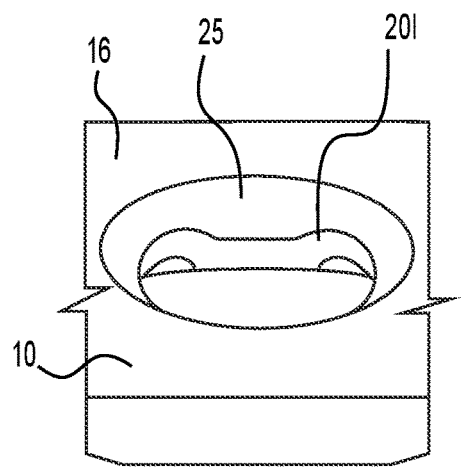  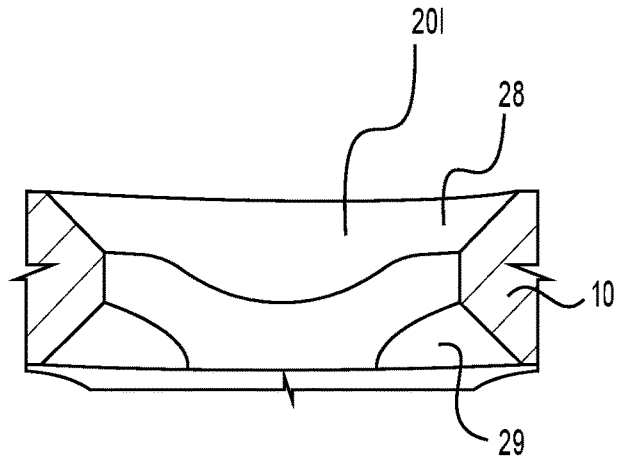
*FIG. 27D*  *FIG. 27E*

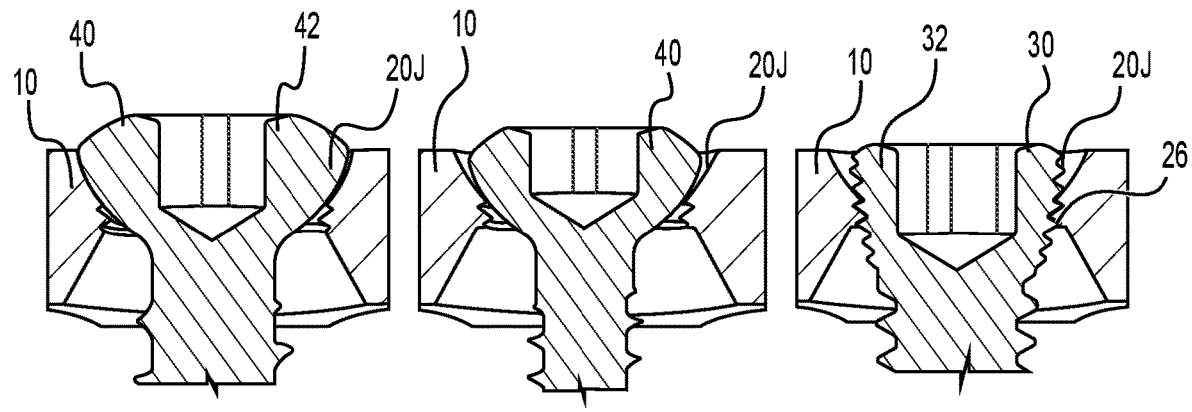
*FIG. 28A*  *FIG. 28B*  *FIG. 28C*
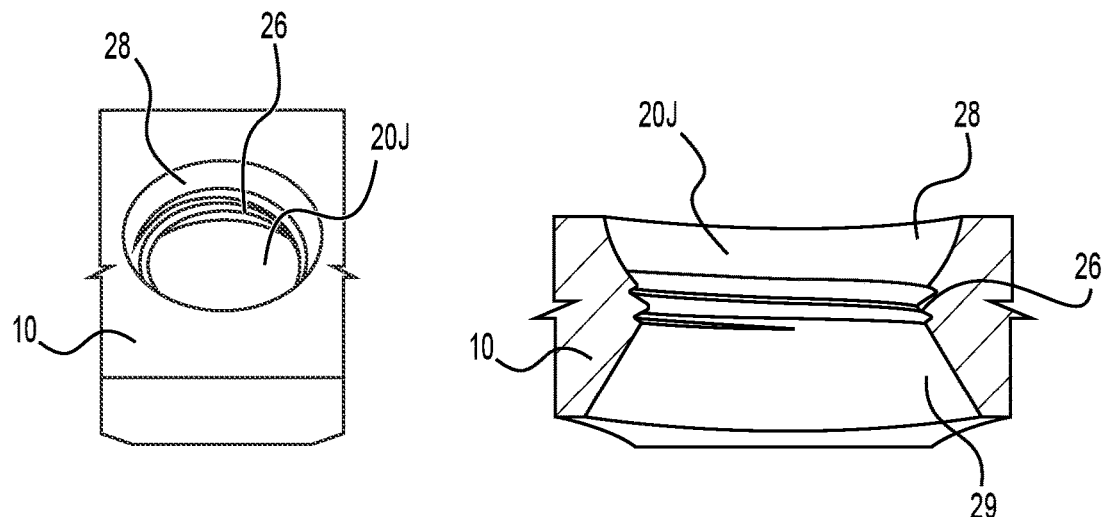
*FIG. 28D*  *FIG. 28E*

STABILIZATION SYSTEMS

CROSS REFERENCE TO RELATED APPLICATIONS

The present application is a continuation of U.S. patent application Ser. No. 16/030,895 filed Jul. 10, 2018, which is continuation-in-part of U.S. patent application Ser. No. 15/893,774, filed Feb. 12, 2018, which is a continuation-in-part of U.S. patent application Ser. No. 15/405,368 filed Jan. 13, 2017, which is a continuation-in-part of U.S. patent application Ser. No. 15/238,772, filed Aug. 17, 2016, each of which is hereby incorporated by reference in its entirety for all purposes.

FIELD

The present disclosure relates to surgical devices, and more particularly, stabilization systems, for example, for trauma applications.

BACKGROUND

Bone fractures are often repaired by internal fixation of the bone, such as diaphyseal or metaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture. Thus, there is a need for plating systems that provide stabilization to the appropriate anatomical area while providing appropriate locking and/or unlocking capability for dynamic compression of the bone.

SUMMARY

To meet this and other needs, devices, systems, and methods of bone stabilization are provided. The stabilization systems may include one or more plates and one or more fasteners. The fasteners may include locking and/or non-locking bone screws that a surgeon may select based on preference for a specific anatomical case. The locking fasteners may connect to the plate and the bone to thereby lock the plate to the bone. The non-locking fasteners may be able to dynamically compress the bone and create interfragmental compression.

According to one embodiment, a stabilization system includes a bone plate and a fastener. The bone plate has an upper surface and a lower surface configured to be in contact with bone, the bone plate having an opening extending from the upper surface to the lower surface. The opening includes a textured portion and non-textured portion, wherein the textured portion comprises a texture that is a non-threaded surface. The fastener is configured to be received by the opening and configured to be inserted into the bone. The opening is configured to receive either a locking fastener or a compression fastener. The locking fastener may have a threaded head portion configured to engage the textured portion and lock to the bone plate, and the compression fastener may have a substantially smooth head portion configured to dynamically compress the bone. The opening may include a combination compression and locking through hole formed by a first bore having a first bore axis and a second bore having a second bore axis different from the first bore axis. In some instances, one of the first and second bores may have an elongated opening, for example, to allow for translation of the non-locking, compression fastener.

According to another embodiment, a stabilization system includes a bone plate, a locking fastener, and a compression fastener. The bone plate has an upper surface and a lower surface configured to be in contact with bone, the bone plate having an opening extending from the upper surface to the lower surface, the opening including a textured portion and non-textured portion, wherein the textured portion comprises a texture that is a non-threaded surface. The locking fastener is configured to be received by one of the openings and configured to be inserted into the bone, wherein the locking fastener has a threaded head portion configured to lock to the bone plate. The compression fastener is configured to be received by one of the openings and configured to be inserted into the bone, wherein the compression fastener has a substantially smooth head portion configured to dynamically compress the bone. Each opening is configured to receive either the locking fastener or the compression fastener.

According to yet another embodiment, a stabilization system includes a bone plate and a fastener. The bone plate has an upper surface and a lower surface configured to be in contact with bone, the bone plate having an opening extending from the upper surface to the lower surface, wherein the opening is formed by at least three different partially overlapping bores including a first bore having at least a partial first internal thread, a second bore having at least a partial second internal thread, and a third bore having at least a partial third internal thread. The fastener is configured to be received by the opening and configured to be inserted into the bone, wherein the opening is configured to receive either a locking fastener or a compression fastener, the locking fastener having a threaded head portion configured to lock to the bone plate, and the compression fastener having a substantially smooth head portion configured to dynamically compress the bone.

According to yet another embodiment, a bone stabilization plate includes an elongate body extending from a first end to a second end and defining at least one screw hole therethrough. A mesh head is connected to the second end of the elongate body. The mesh head includes a plurality of rings, with each of the rings defining a screw hole. Bridge portions extend between and interconnect the rings. The bridge portions have a reduced thickness compared to the rings.

According to another embodiment, a bone stabilization plate includes a mesh body. The mesh body includes a plurality of rings, with each of the rings defining a screw hole. Bridge portions extend between and interconnect the rings. The bridge portions have a reduced thickness compared to the rings.

According to another embodiment, a bone stabilization plate includes an elongated body extending between first and second ends and having an upper surface and an opposed bone contacting surface. The bone contacting surface has a scalloped configuration and at least one of the ends has a beveled configuration. The body defines a plurality of screw holes and each of the screw holes have the same diameter.

According to yet another embodiment, a bone stabilization plate includes an elongate body extending from a first end to a second end along a longitudinal axis, the elongate body defining at least one screw hole therethrough, first and second ears extending from the second end of the elongate body, each of the first and second ears defining a screw hole therethrough, and a first tine extending from the first ear and a second tine extending from the second ear, the first and second tines each terminating at a sharp point.

Also provided are additional stabilization systems, methods for installing the stabilization systems, and kits including bone plates, fasteners, and components for installing the same.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 19A-19E shows alternative locking screw and openings in plates according to yet another embodiment;

FIGS. 26A-26D depict a plate assembly according to one embodiment where a locking or non-locking fastener may be positioned at an angle or perpendicular to the plate;

FIGS. 27A-27E depict a non-locking fastener with a dynamic compression slot in a plate according to one embodiment;

FIGS. 28A-28E show alternative fastener types and a stacked hole configuration in a plate according to another embodiment;

DETAILED DESCRIPTION

Figure 1:
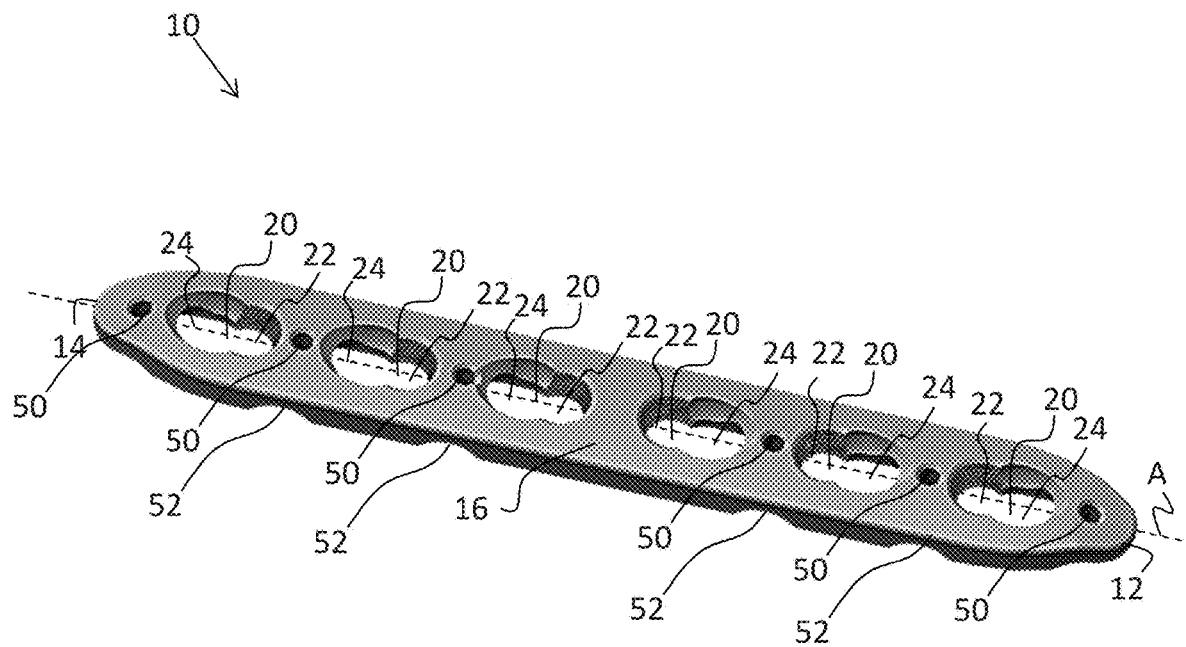
FIG. 1 depicts a top perspective view of a diaphyseal bone plate according to one embodiment.

Embodiments of the disclosure are generally directed to devices, systems, and methods for bone stabilization. Specifically, embodiments are directed to bone plating with locking and/or non-locking fasteners for dynamic compression of the bone. The hole designs may allow for fixed angle and/or polyaxial locking and/or non-locking of the fasteners. Some embodiments include blocking fasteners to prevent the bone fastener from backing out. Some embodiments further include locking fasteners with self-forming threads configured to displace the plate material, thereby locking the fastener to the plate.

The plates may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

The bone plate may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Referring now to the drawing, FIGS. 1-9 depict one embodiment of a plate 10 including one or more openings 20. The openings 20 extending through the plate 10 are configured to accept locking fasteners 30, non-locking fasteners 40, or a combination of both locking and non-locking fasteners 30, 40 that are able to dynamically compress the bone and/or affix the plate 10 to the bone. When plating diaphyseal bone, surgeons may use a combination of both locking and non-locking fasteners 30, 40 that are able to dynamically compress bone and to connect the bone and the plate 10. Dynamic compression may also be desirable to create interfragmental compression while tightening the fasteners 30, 40.

Figure 2:
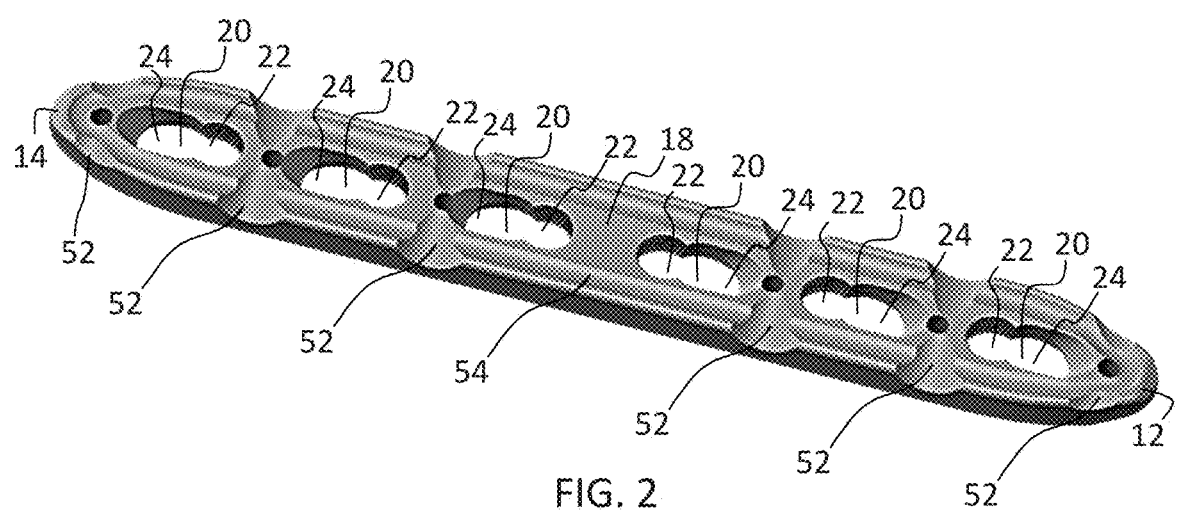
FIG. 2 depicts a bottom perspective view of the plate of FIG. 1.

As shown in FIGS. 1 and 2, the plate 10 has a body that extends from a first end 12 to a second end 14 along a central longitudinal axis A. The plate 10 includes a top surface 16 and an opposite, bottom surface 18 configured to contact adjacent bone. The top and bottom surfaces 16, 18 are connected by opposite side surfaces extending from the first to second ends 12, 14 of the plate 10. Although the plate 10 is shown having a generally longitudinal body, it will be appreciated that any suitable shape and contouring of the plate 10 may be provided depending on the location and type of fracture to be plated.

The plate 10 includes one or more through openings 20 configured to receive one or more bone fasteners 30, 40. The openings 20 extend through the body of the plate 10 from the top surface 16 to the bottom surface 18. Each of the openings 20 may be in the form of a combination opening that has at least two overlapping holes. As shown in FIG. 1, the combination opening 20 includes a first hole 22 overlapping a second hole 24. One of the holes 22 may be configured to be the locking hole 22, thereby able to receive and secure the locking fastener 30 to the plate 10, and the other of the holes 24 may be configured to be the dynamic compression hole 24, thereby allowing the non-locking fastener 40 to freely move in the hole 24 and apply dynamic compression. The locking hole 22 may have one or more locking features designed to engage with a locking fastener 30, and the dynamic compression hole 24 may be elongated, for example, along the central longitudinal axis A of the plate 10. The screw holes 22, 24 are not constrained to parallel axes. This hole geometry may be used in bone plates 10 to utilize either fixed angle or variable angle locking screws 30 and/or polyaxial non-locking screws 40 that can achieve dynamic compression.

The plate 10 may comprise any suitable number of openings 20 in any suitable configuration. As shown, the plate 10 is a generally an elongate plate 10 including six combination openings 20 positioned along the central longitudinal axis A of the plate 10. The combination openings 20 may also be oriented in any suitable orientation such that the locking holes 22 and dynamic compression holes 24 are optimized based on the type and location of the fracture. As shown, starting from the second end 14 of the plate 10, three of the combination openings 20 are aligned such that the dynamic compression holes 24 are positioned toward the second end 14, and the three combination openings 20 past the midline of the plate 10, are reversed and aligned such that the dynamic compression holes 24 are now positioned toward the first end 12 of the plate.

These openings 20 allow surgeons more flexibility for fastener placement, based on preference, anatomy, and fracture location. Surgeons may have differing opinions as to whether non-locking or locking screws 30, 40 (or some combination of the two) should be used in diaphyseal bone. Further, complexity of fracture location and shape makes having as many locations for fasteners 30, 40 as possible necessary. This design offers surgeons a versatile method to achieve higher accuracy in placement of locking and/or non-locking screws 30, 40.

Figure 4:
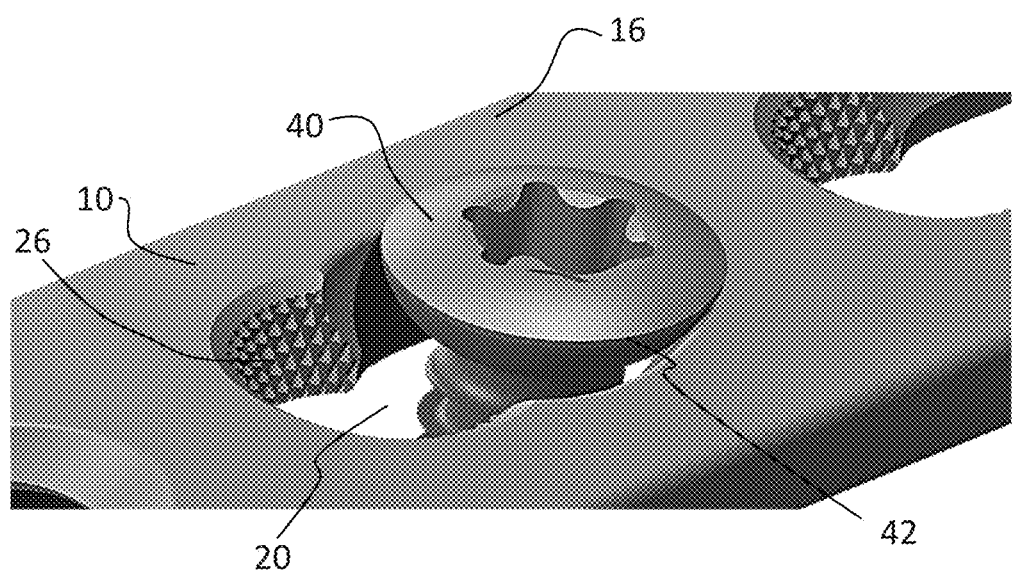
FIG. 4 shows the head of the fastener engaged with a portion of the combination hole.
Figure 5:
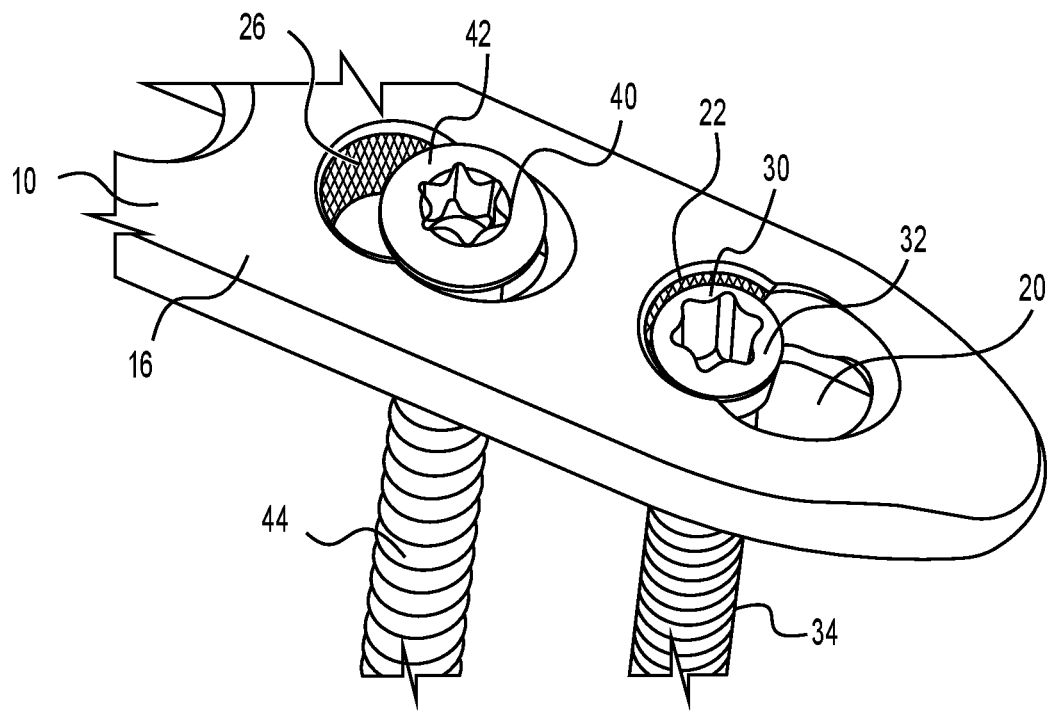
FIG. 5 is a top perspective view of two fasteners engaged with the two combination holes.
Figure 6:
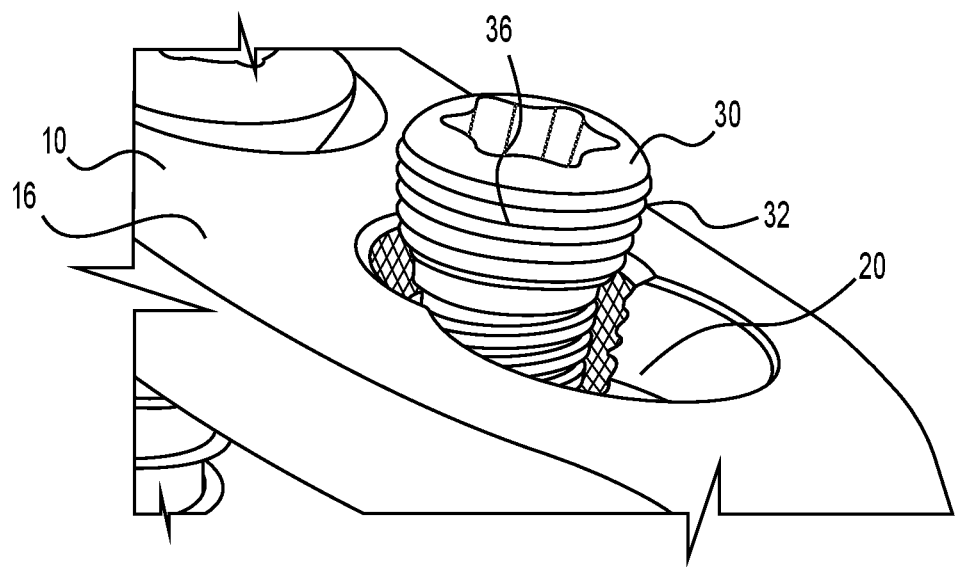
FIG. 6 is a close-up perspective view of the fastener head before engaging the textured portion of the combination hole.

As best seen in FIGS. 4-6, the locking and non-locking fasteners 30, 40 are shown. The locking and non-locking fasteners 30, 40 may include traditional fasteners known in the art. The locking and non-locking fasteners 30, 40 may comprise bone screws or the like. The fasteners 30, 40 may also include other fasteners or anchors configured to be secured or engaged with bone, such as nails, spikes, staples, pegs, barbs, hooks, or the like. The fasteners 30, 40 may include fixed and/or variable angle bone screws.

The locking fastener 30 may include a head portion 32 and a shaft portion 34 configured to engage bone. The shaft portion 34 may be threaded such that the fastener 30 may be threaded into the bone. The head portion 32 of the locking fastener 30 includes a textured area 36 around its outer surface sized and configured to engage with the locking hole 22 of the combination opening 20. The textured area 36 may include threads, ridges, bumps, dimples, serrations, or other types of textured areas. As shown, the texture area 36 preferably includes a threaded portion extending substantially from the top of the head portion 32 to the bottom of the head portion 32 proximate to the shaft portion 34. Thus, when the textured area 36 engages the locking hole 22, the locking fastener 30 is thereby locked to the plate 10.

The non-locking fastener 40 includes a head portion 42 and a shaft portion 44 configured to engage bone. The shaft portion 44 may be threaded such that the fastener 40 may be threaded into the bone. The head portion 42 of the non-locking fastener 40 is substantially smooth around its outer surface such that is able to slide along the elongated compression hole 24. Thus, the non-locking fastener 30 may be coupled to the plate 10, but not locked thereto to enable dynamic compression of the bone. It will be recognized that the head portions 32, 42 of the fasteners 30, 40 may include a recess configured to receive a driver or the like.

As best seen in FIGS. 2 and 4, the locking hole portion 22 of the combination opening 20 includes a textured portion 26. The textured portion 26 may include threads, ridges, bumps, dimples, serrations, knurls, or other types of textured areas. The textured portion 26 may be of the same type (e.g., mating surfaces) or different from the textured area 36 of the locking fastener 30. As shown, the textured portion 26 is serrated or knurled along an inner portion of the hole 22. The knurled surface may include straight, angled, or crossed lines cut or rolled into the material. In the embodiment shown in FIG. 1-6, the textured portion 26 extends along substantially the entire inner surface of the hole 22. With reference to the embodiment shown in FIGS. 7-9, the combination hole 20 is substantially the same as that shown in FIGS. 1-6 except that the textured portion 26 the locking hole 22 now includes a thin centralized textured ribbon of material. For example, the textured portion 26 takes up about half or less of the surface area of the hole 22. In this instance, only a portion of the textured area 36 of the head portion 32 of the locking fastener 30 engages with and locks to the textured portion 26 of the hole 22.

Figure 7:
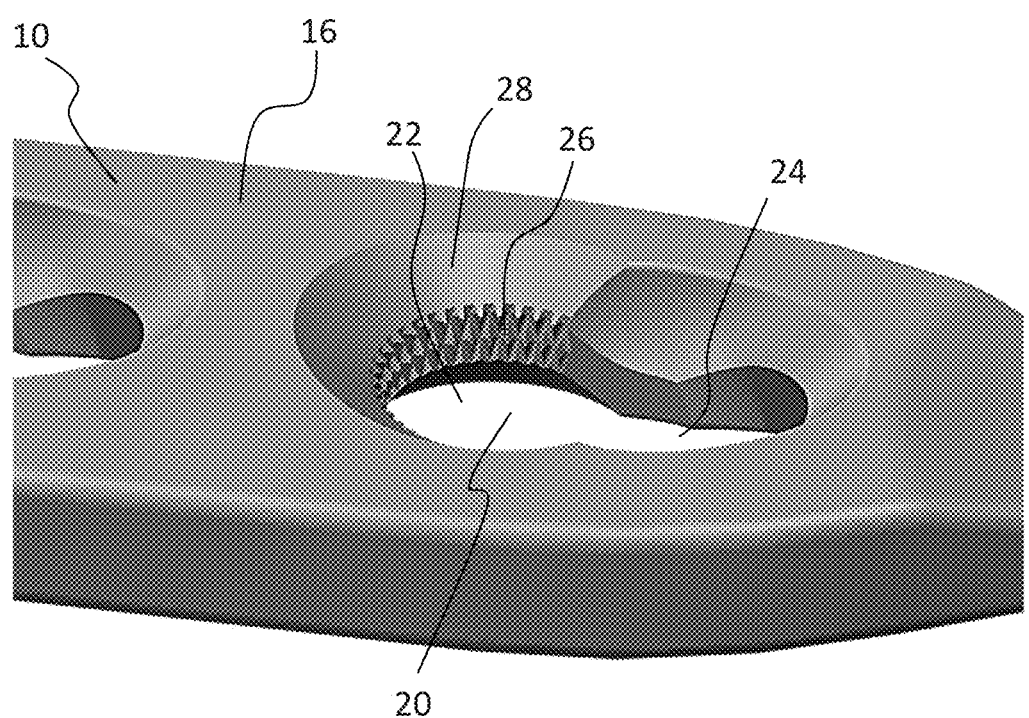
FIG. 7 is a close-up view of an alternative version of a combination hole according to another embodiment.
Figure 8:
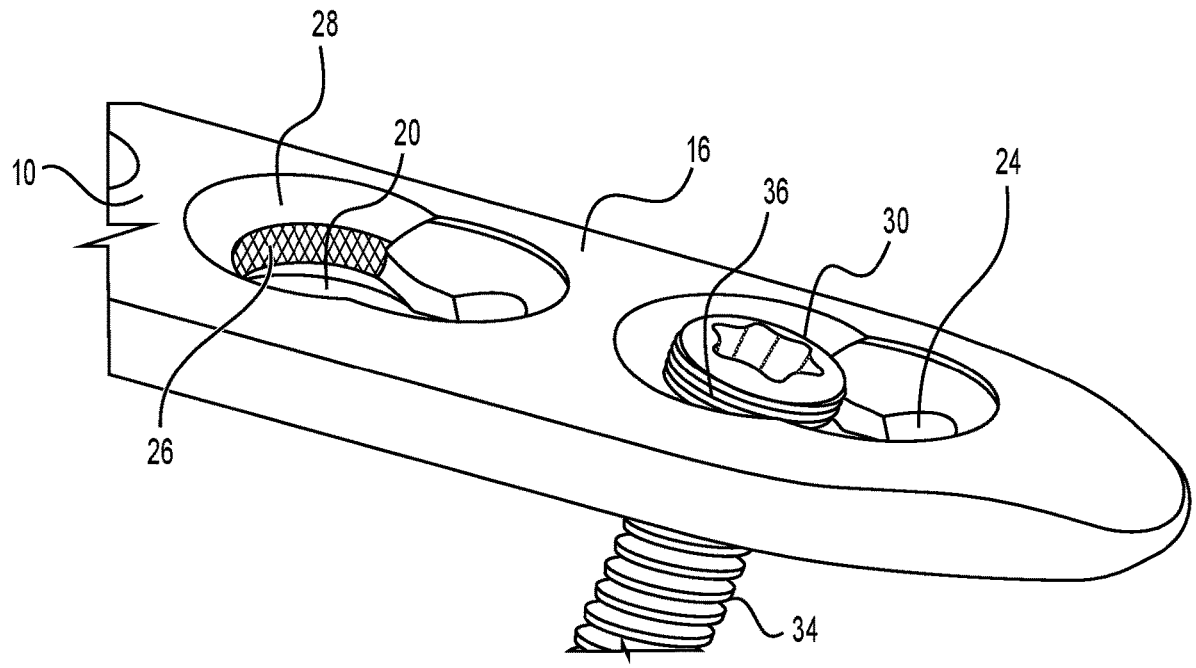
FIG. 8 is a perspective view of a fastener inserted through the combination hole of FIG. 7.
Figure 9:
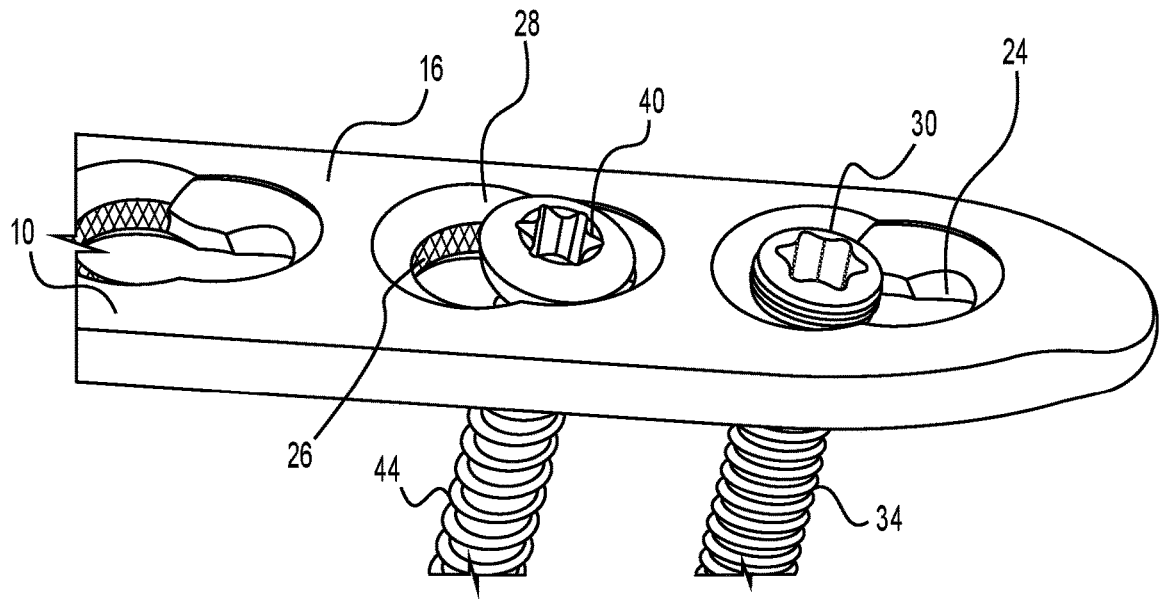
FIG. 9 is a perspective view of two fastener inserted through the combination holes of FIG. 7.

An upper portion of the hole 22 may be tapered 28, without texturing, for example, to facilitate alignment of the fastener 30 with the opening 20. As shown in FIGS. 6-8, this tapered portion 28 is enlarged in area relative to the embodiment in FIGS. 1-5. The hole 22 may be configured to receive a fixed or variable angle fastener 30. The hole 22 may be generally conical in shape such that it is wider near the top surface 16 of the plate 10 and narrower toward the bottom surface 18 of the plate 10. The tapered portion 28 and/or the textured area 26 may be conical in shape. In this embodiment, the locking hole 22 is a textured fixed angle conical hole configured to receive locking fastener 30. The textured holes 22 may deform as the fastener head 32 interferes with the textured portion 26 of the hole 22, thereby providing a positive lock between the fastener 30 and the plate 10.

The second hole portion 24 of the combination opening 20 may be an elongated dynamic compression hole. The dynamic compression hole 24 may be elongated such that it has a length greater than its width. The hole 24 may be elongated along the longitudinal axis A of the plate 10. In the alternative, the hole 24 may be generally cylindrical such that the hole 24 only permits polyaxial movement of the fastener 40. The inner surface of the hole 24 may be substantially smooth such that the non-locking fastener 40 is able to freely pivot and/or slide along the elongated hole 24. This provides for at least two directions of compressive force (e.g., along the longitudinal axis A and perpendicular to the longitudinal axis A). The head portion 42 of the non-locking fastener 40 may be substantially smooth around its outer surface. The head portion 42 is sized and configured to engage with and be retained within the hole portion 24 of the combination opening 20. The hole 24 may be configured to receive a fixed or variable angle fastener 40. In one embodiment, the hole 24 may be generally conical in shape and/or tapered such that it is wider near the top surface 16 of the plate 10 and narrower toward the bottom surface 18 of the plate 10. In this embodiment, the hole 24 is a smooth variable angle conical hole configured to receive the non-locking fastener 40. The hole 24 may receive the fastener head 42 allowing movement of the fastener 40, for example, in a polyaxial fashion and/or along the length of the hole 22, thereby providing dynamic compression of the bone.

The plate 10 may have one or more additional features. For example, the plate 10 may include one or more through holes 50 extending through the plate 10. For example, holes 50 may extend from the top surface 16 to the bottom surface 18 of the plate 10. These holes 50 may be configured to receive k-wires (not shown). In the embodiment shown, six holes 50 are provided along the central longitudinal axis A of the plate 10 to receive one or more k-wires. Although it will be appreciated that any number and location of holes 50 may be provided for receiving k-wires. The plate 10 may also include one or more reliefs to minimize contact of the plate 10 with the bone and preserve the anatomy. For example, the relief may be in the form of one or more conical cuts 52 along the bottom surface 18 of the plate 10. The conical cuts 52 may be positioned on either side of the k-wire holes 50 and extend outward towards the side surfaces of the plate 10. Each conical cut 52 may include a narrowed portion proximate to the k-wire hole 50 (e.g., along the central longitudinal axis A of the plate 10) and a widened portion proximate to the outer side surfaces. Although twelve conical cuts 52 are provided around the six k-wire holes 50, it is envisioned that the conical cuts 52 may be provided at any suitable location and number as would be recognized by one of skill in the art. The plate 10 may further include one or more perimeter reliefs 54 extending around the bottom surface 18 of the plate 10 to reduce unnecessary contact with bone as an anatomy preserving measure. As shown, the perimeter relief 54 is a cutout in the bottom surface 18 of the plate 10 which extends around the outer perimeter of the plate 10. The perimeter relief 54 is interrupted by each of the conical cuts 52. The perimeter relief 54 generally leaves an outer edge surface (e.g., around the sides and first and second ends 12, 14 of the plate 10) except where interrupted by the conical cuts 52 and a central portion of the bottom surface raised relative to the relief 54. The width and depth of the relief 54 may be of any suitable dimension to provide adequate contact between the plate 10 and the bone while minimizing unnecessary contact to preserve the anatomy.

Turning now to FIGS. 10-18, alternative types of openings 20A-20G, which provide for locking and/or non-locking, dynamic compression, and the like, are provided. Although only the holes are exemplified in these figures, it will be appreciated that the plate 10 may be of any suitable size, shape, and dimension depending on the plating application. As many of the features of these openings are similar to the combination openings 20 described already for FIGS. 1-9, only the different features will be further explained.

Figure 10A:
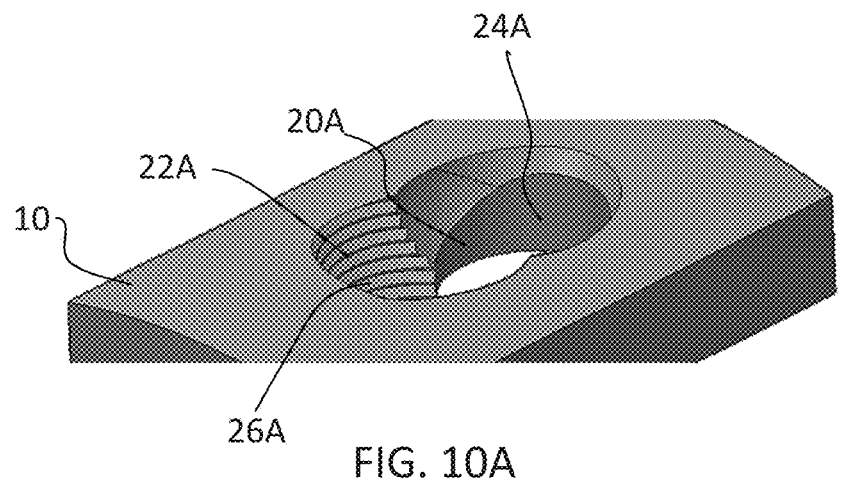
FIGS. 10A-10C show a perspective view, top view, and cross-section view, respectively, of another embodiment of a combination hole.
Figure 10B:
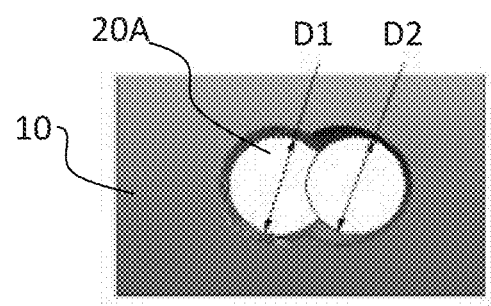
Figure 10C:
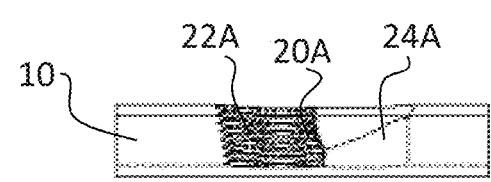

With reference to FIGS. 10A-10C, the combination opening 20A is similar to combination opening 20 except that the dynamic compression hole 24A has the same general diameter as the locking hole 22A, and the locking hole 22A includes a different type of textured portion 26A. In this embodiment, the locking hole 22A has a first diameter D1, and the dynamic compression hole 24A has a second diameter D2. Unlike the elongated hole 24 described earlier, dynamic compression hole 24A has substantially same diameter as the locking hole 22A. Thus, the first and second diameters D1, D2 are substantially the same. The hole 24A may be formed by milling or drilling a sphere out of the plate 10 in the center of the circle with tapers or ramps on either side. The hole 24A is not elongated, but is generally circular and the non-locking fastener 40 will be allowed to translate in the hole 24A because the diameter of the head portion 42 and/or shaft (e.g., bone thread) will be smaller than the size of the hole 24A in the plate 10. With respect to hole 22A, the textured portion 26A of the hole 22A may be in the form of a tapered thread. This tapered thread may generally correspond to a similar tapered thread on the locking fastener 30. This hole 22A also does not include a tapered portion, and the textured portion 26A begins at the intersection with the top surface 16 of the plate 10. This alternative opening 20A also provides for the use of both locking and non-locking fasteners 30, 40 that are able to dynamically compress bone and/or lock the plate 10 to the bone.

Figure 11A:
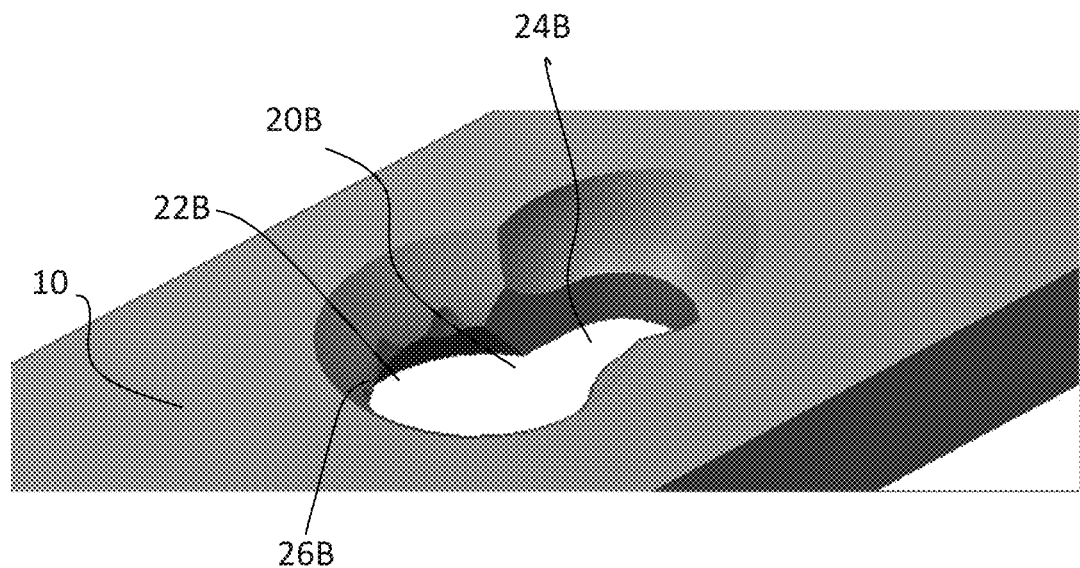
FIGS. 11A-11C show a perspective view, top view, and cross-section view, respectively, of another embodiment of a combination hole.
Figure 11B:
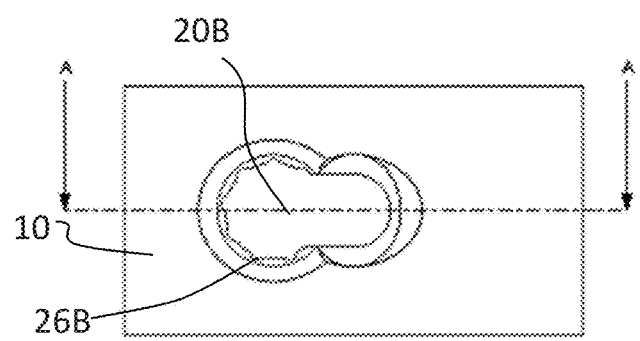
Figure 11C:
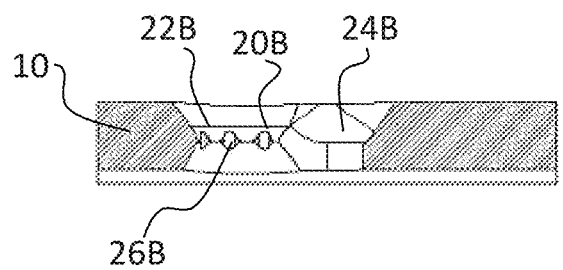

Turning now to FIGS. 11A-11C, the combination opening 20B is similar to other combination openings except that the locking hole 22B includes a different type of textured portion 26B. The textured portion 26B includes a series of alternating recesses and protrusions around a central portion of the hole 22B. The recesses may be in form of a wave of alternating cutouts extending around the inner perimeter of the hole 22B. The textured portion 26B may lock the fastener 30 with a friction fit or may be modified during insertion of the fastener 30 to form a lock in situ. In this embodiment, the locking hole may allow for polyaxial locking. The plate 10 and the locking fastener 30 may be made of dissimilar materials having dissimilar hardness values. For example, the fastener 30 may have a higher hardness (e.g., on the Rockwell scale) relative to the plate 10, which may be formed of a material having a lower relative hardness value. Due to the increased hardness, the head portion 32 of the locking fastener 30 may create a thread in the plate 10 as the fastener 30 is inserted (e.g., threaded) into the hole 22B, thereby locking the fastener 30 to the plate 10.

Figure 12A:
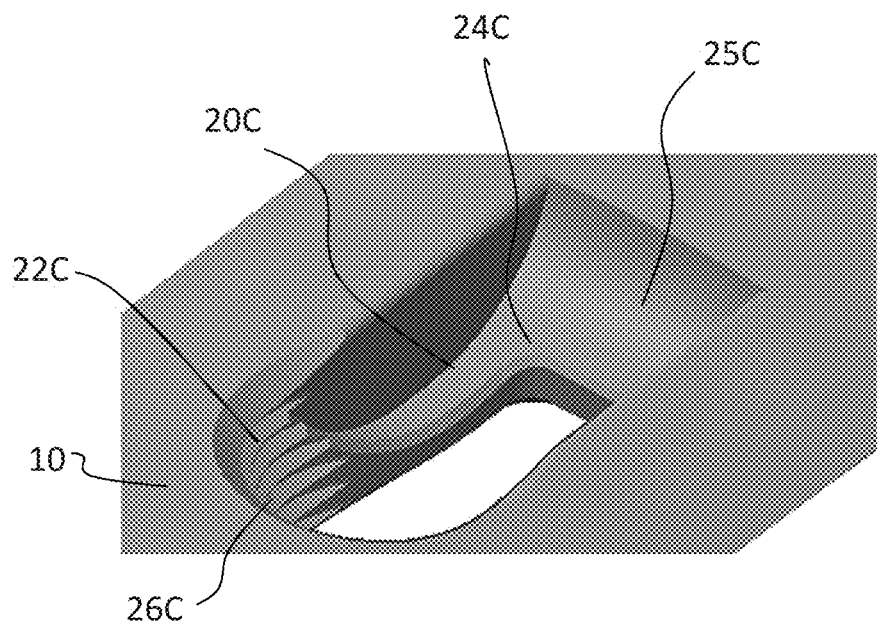
FIGS. 12A-12C show a perspective view, top view, and cross-section view, respectively, of another embodiment of a hole for receiving a fastener.
Figure 12B:
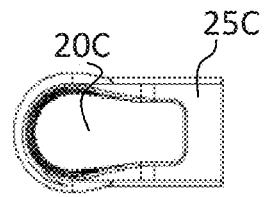
Figure 12C:
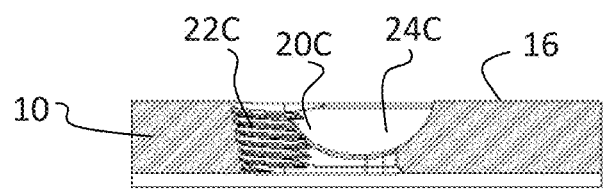

With reference to FIGS. 12A-12C, the opening 20C includes locking hole 22C and dynamic compression hole 24C with a more open configuration. The locking portion 22C has a textured portion 26C in the form of a tapered thread. This tapered thread may generally correspond to a similar tapered thread on the locking fastener 30. The opposite portion 24C of the opening 20C is oblong with a ramp 25C milled into the top surface 16 of the plate 10 to allow for dynamic compression. As best seen in FIG. 12C, the ramp may be partially spherical in shape and extend from the top surface 16 of the plate 10 and connect to the textured portion 26C. When viewed from above in FIG. 12B, the ramp 25C creates a square-like, key-hole, and/or non-hole geometry that sweeps into the tapered threaded locking hole 22C. This alternative opening 20C also provides for the use of both locking and non-locking fasteners 30, 40 that are able to dynamically compress bone and/or lock the plate 10 to the bone.

Figure 13A:
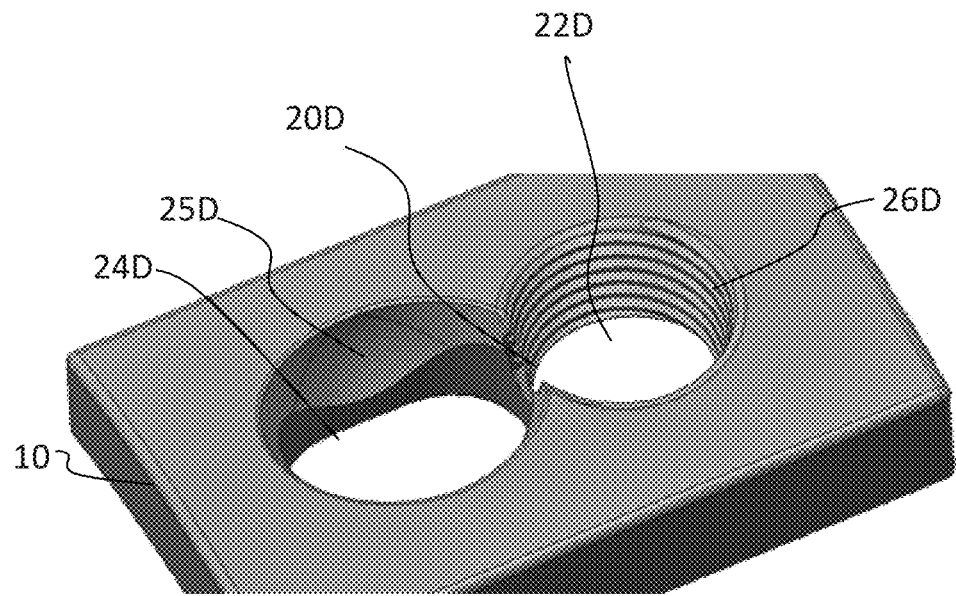
FIGS. 13A-13C show a perspective view, top view, and cross-section view, respectively, of another embodiment of a combination hole.
Figure 13B:
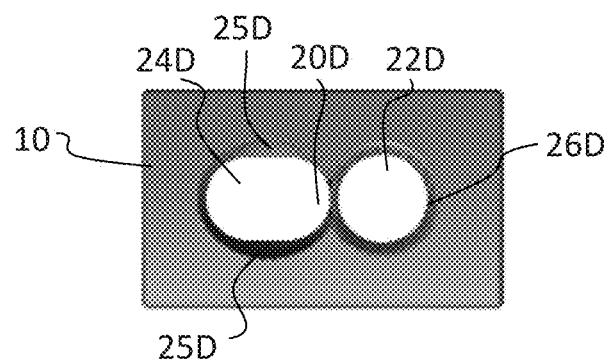
Figure 13C:
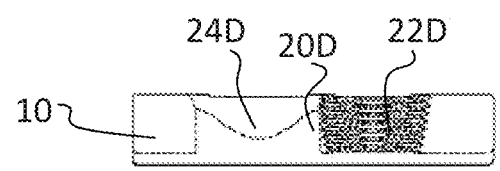

Turning now to FIGS. 13A-13C, the opening 20D includes locking hole 22D and dynamic compression hole 24D. These holes 22D, 24D are connected and close together but are not overlapping. The holes 22D, 24D are separated by a small portion or sliver of plate material proximate to the lower portion of the holes 22D, 24D (e.g., at bottom surface 18 of the plate 10 and partially extending between the holes 22D, 24D). The locking portion 22D has a textured portion 26D in the form of a tapered thread. The textured portion 26D extends around almost the entire circumference of the hole 22D except where connected to hole 24D. The dynamic compression hole 24D is elongated and has ramped portions 25D on opposite sides of the hole 24D to receive fastener 40. This configuration allows for a very close population of holes 22D, 24D on the plate 10 while giving structural stability at the holes 22D, 24D.

Figure 14A:
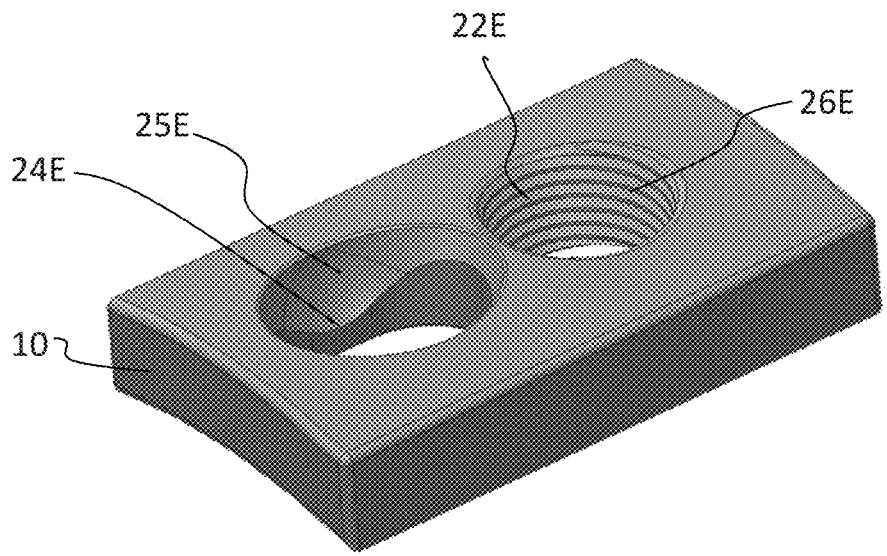
FIGS. 14A-14C show a perspective view, top view, and cross-section view, respectively, of another embodiment of separate locking and non-locking holes.
Figure 14B:
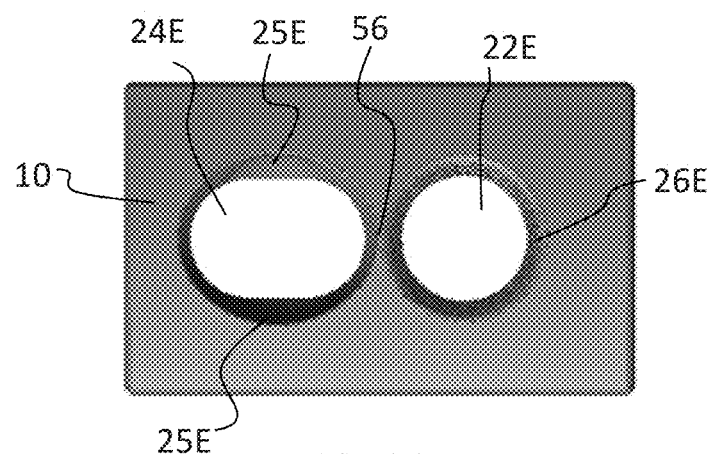
Figure 14C:
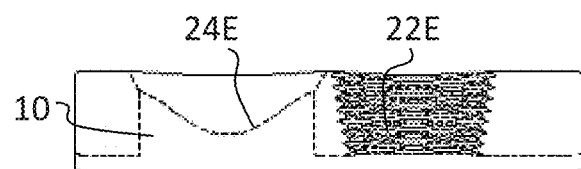

With reference to FIGS. 14A-14C, locking hole 22E and dynamic compression hole 24E are adjacent, but separate from one another. The holes 22E, 24E are completely separated from one another by a wall 56 of plate material. The locking portion 22E has a textured portion 26E in the form of a tapered thread extends around the entire perimeter of the hole 22E. The dynamic compression hole 24E is elongated and has ramped portions 25E on opposite sides of the hole 24E. This configuration also allows for a very close population of holes 22E, 24E on the plate 10 while giving options for both locking and/or dynamic compression.

Figure 15A:
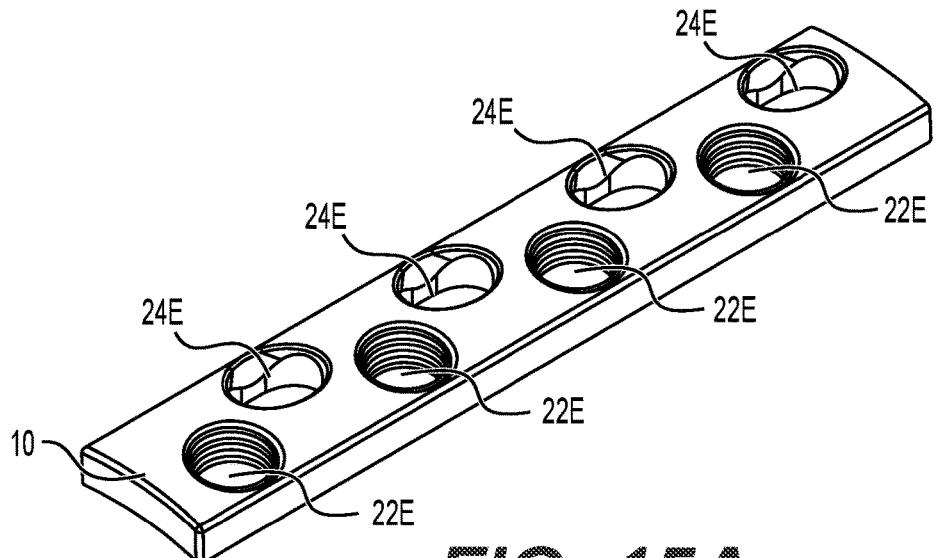
FIGS. 15A-15C show a perspective view, top view, and cross-section view, respectively, of one embodiment of a plate including the separate locking and non-locking holes.
Figure 15B:
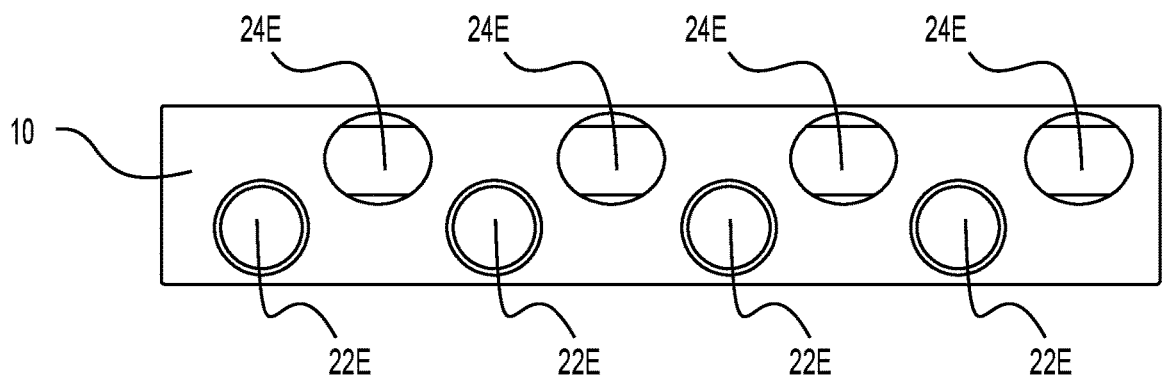
Figure 15C:
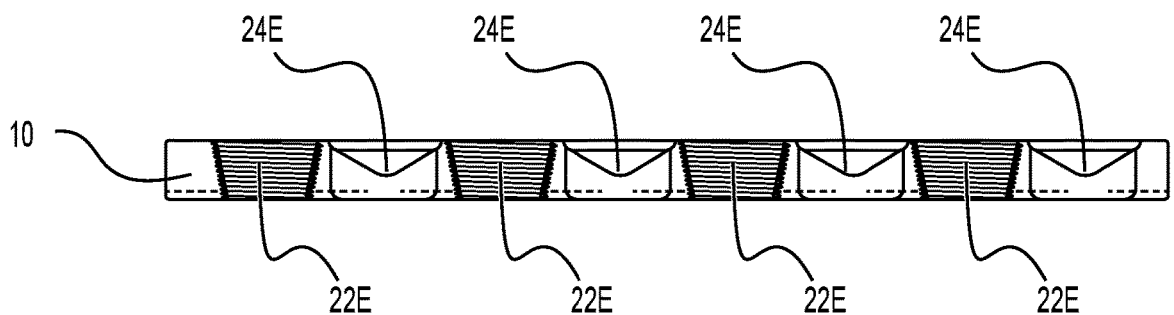
Figure 16A:
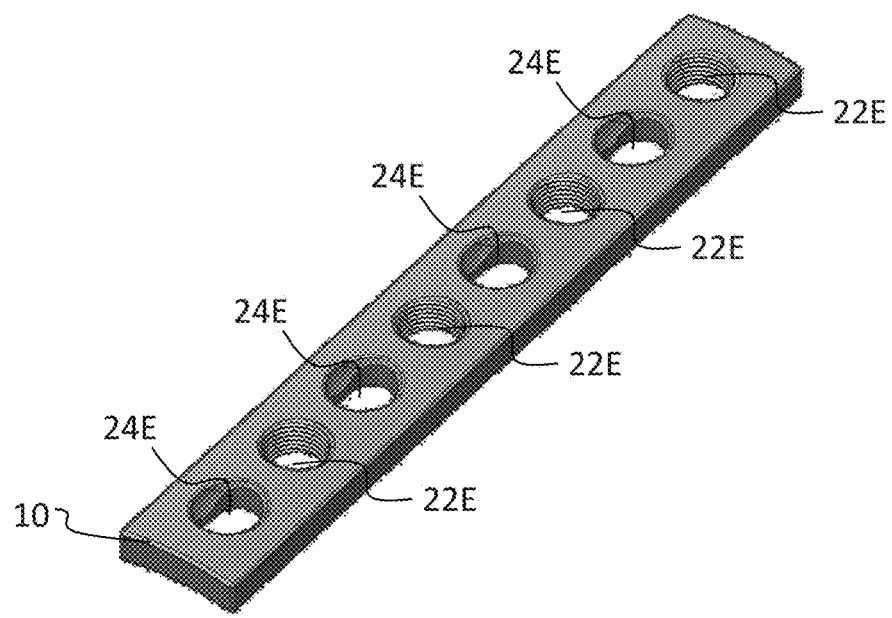
FIGS. 16A-16C show a perspective view, top view, and cross-section view, respectively, of another embodiment of a plate including the separate locking and non-locking holes.
Figure 16B:
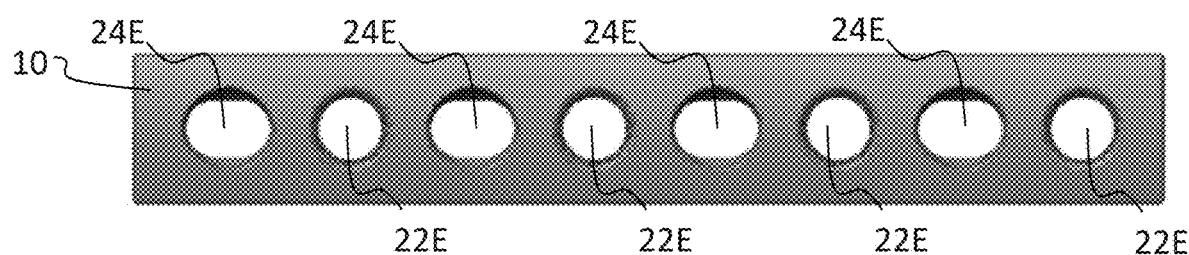
Figure 16C:
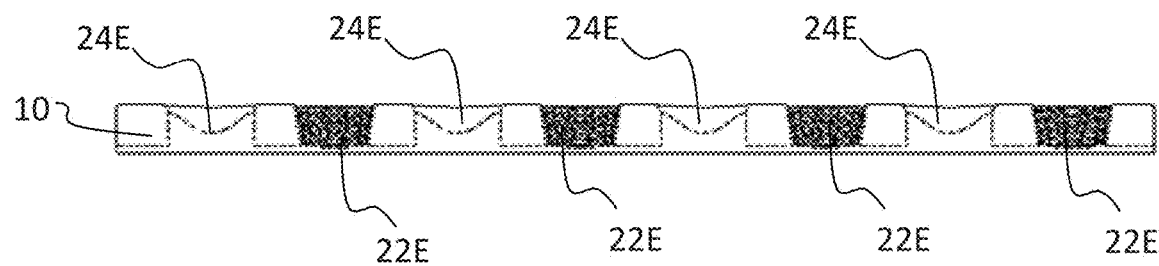

FIGS. 15A-15C and 16A-16C show alternative arrangements of locking holes 22E and dynamic compression holes 24E on plate 10. As shown in FIGS. 15A-15C, the locking and non-locking holes 22E, 24E are staggered over the length of the plate 10. A first series of locking holes 22E are arranged in a first line along the length of the plate 10, and a second series of non-locking holes 24E are arrange in a second line along the length of the plate 10. The first line of holes 22E are offset relative to the second line of holes 24E such that every other hole will be non-locking or locking. Although depicted in straight lines, it is contemplated that the holes 22E, 24E may not necessarily be arranged in a straight line. In FIGS. 16A-16C, the locking and non-locking holes 22E, 24E are staggered along the length of the plate 10 such that each hole alternates between a locking hole 22E and a non-locking hole 24E. The holes 22E, 24E are generally aligned along the central longitudinal axis of the plate 10, but it will be appreciated that the holes may be offset or aligned in any suitable number and configuration along the plate 10.

Turning now to FIGS. 17A-17D, an alternative version of opening 20F is provided. In this embodiment, the hole construct 20F is comprised of at least three overlapping conical threaded holes in the plate 10. The opening 20F includes a first, locking hole 22F, a second hole 24F, and a third hole 23F arranged along a longitudinal axis of the plate 10. The third hole 23F is the mirror image of hole 24F across the first locking hole 22F. The conically threaded holes 22F, 23F, 24F may or may not have parallel axes. Each hole 22F, 23F, 24F may include a textured portion 26F, for example, in the form of one or more threaded portions. Thus, the locking fastener 30 may lock to any of the holes 22F, 23F, 24F. Although each of the holes 22F, 23F, 24F are shown in with the textured portion 26F, it will be appreciated that one or more of the holes 22F, 23F, 24F may have a substantially smooth inner portion instead of the textured portion 26F. The upper part of the hole construct at the first and second ends of the hole 20F each have a ramped feature 25F (e.g., adjacent to holes 23F and 24F) to allow for dynamic compression of the plate 10. In addition, the ramped feature 25F may span the three or more conical holes 22F, 23F, 24F (e.g., around the entire perimeter of the opening 20F).

Figure 17A:
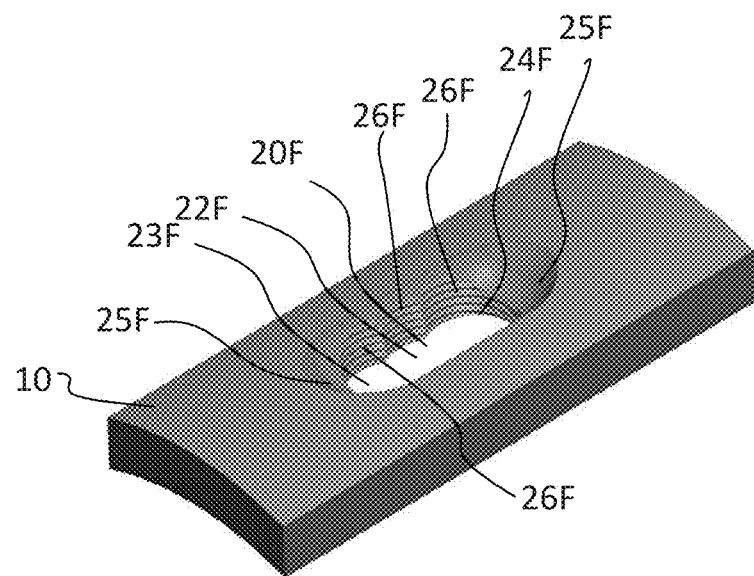
FIGS. 17A-17D show a perspective view, a top view, a cross-section view, and a perspective view with a locking fastener, respectively, according to another embodiment of a plate including three overlapping locking and non-locking holes.
Figure 17B:
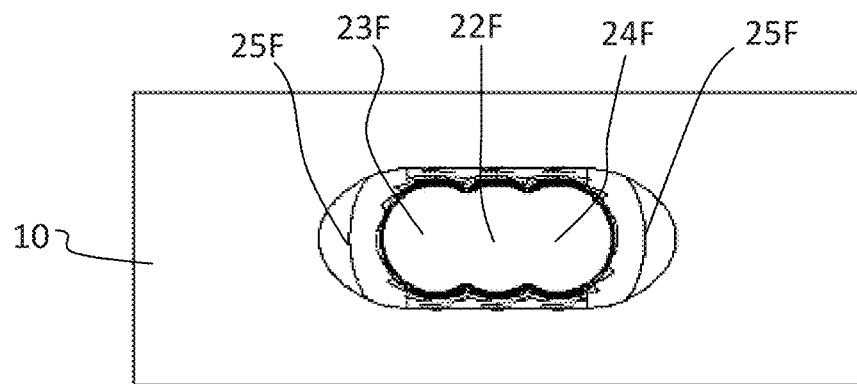
Figure 17C:
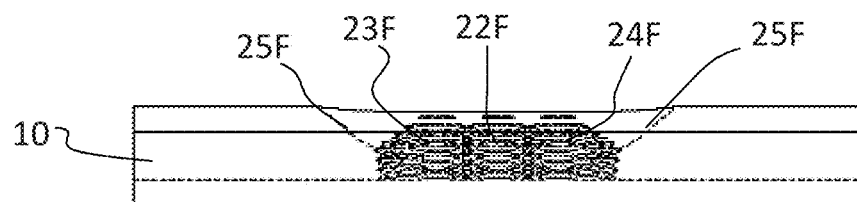
Figure 17D:
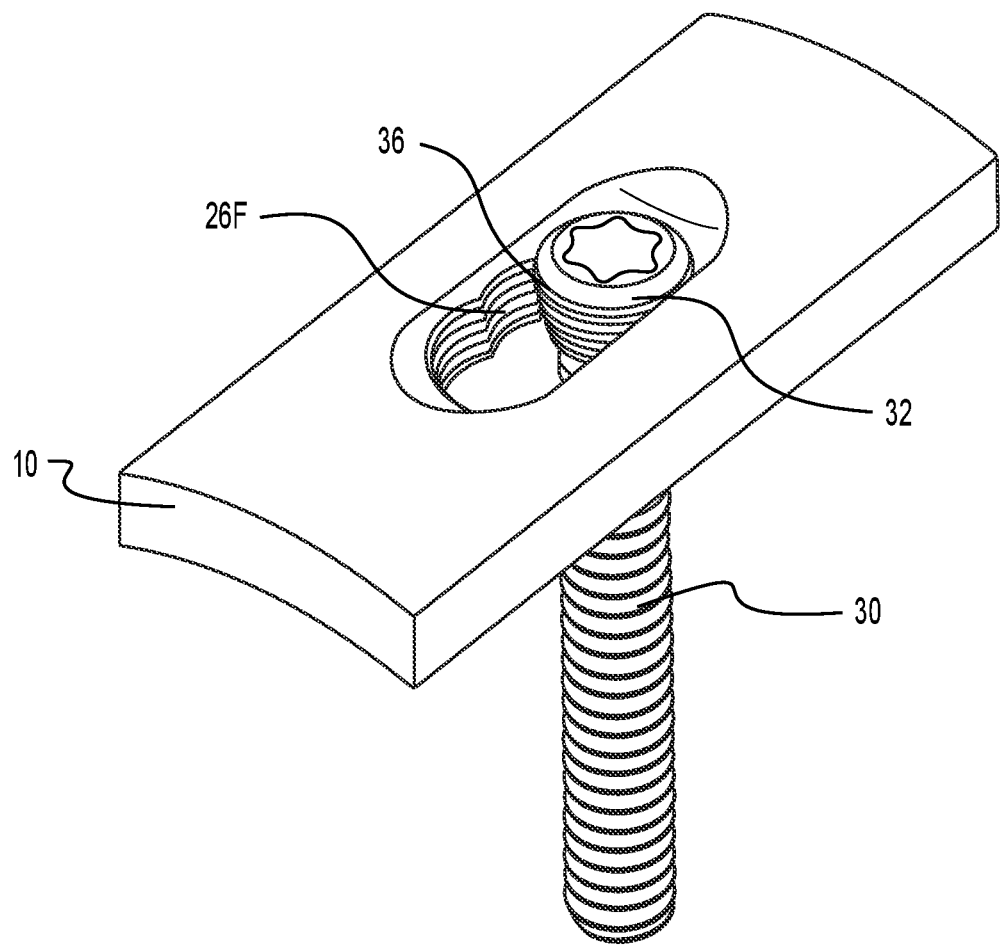

The non-locking compression fasteners 40 may have a major bone thread diameter such that the fastener 40 can translate between overlapping holes 22F, 24F, 23F without interference. As best seen in FIG. 17D, the locking fastener 30 may include a textured area 36, for example, in the form of a thread, configured to engage with the textured portion 26F of any of the holes 22F, 23F, 24F. The hole geometry of opening 20F can be applied to bone plates 10 to utilize either fixed angle and/or variable angle locking screws 30 and/or polyaxial non-locking screws 40 that can achieve dynamic compression. This allows surgeons more flexibility for screw placement, based on preference, anatomy, and fracture location.

Figure 18A:
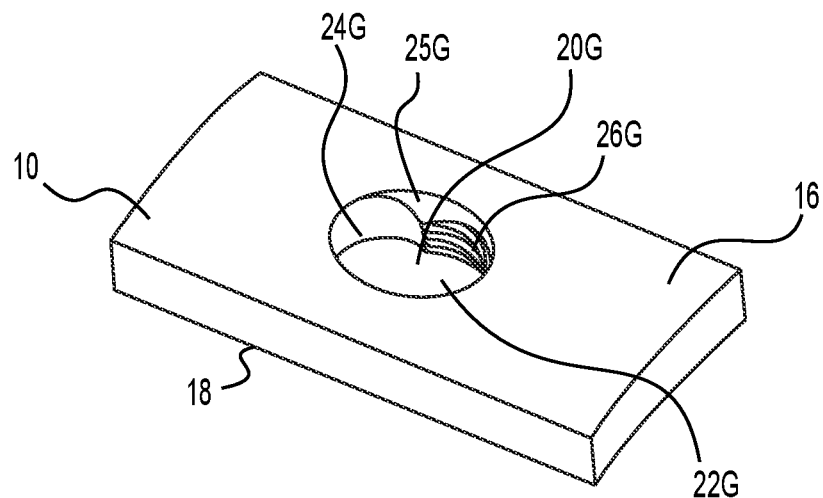
FIGS. 18A-18B show perspective views of a plate according to another embodiment with locking and non-locking functionality.
Figure 18B:
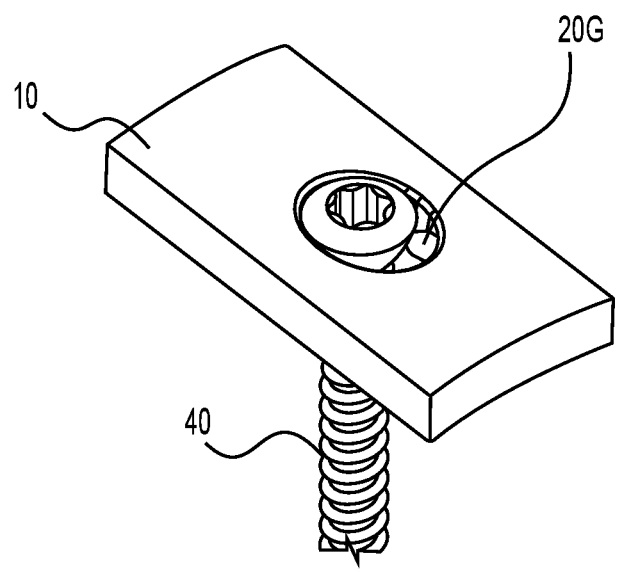

Turning now to FIGS. 18A-18B, another embodiment of opening 20G is provided. This opening 20G may be comprised of one elongate hole or slot extending from the top surface 16 to the bottom surface 18 of the plate 10. A locking portion 22G of the opening 20G may include a textured portion 26G having straight machine threads. The threads may extend more than 180 degrees to retain the locking fastener 30. A non-locking portion 24G of the opening 20G may be positioned opposite the locking portion 22G to complete the opening 20G. The upper part of the opening 20G may have one or more ramped features 25G to allow for dynamic compression of the plate 10. The ramp 25G may span along the entire upper perimeter of the elongated slot 20G or a portion thereof. The compression screws 40 may have a major bone thread diameter such that the screws 40 are able to translate along the opening 20G without interference.

With reference to FIGS. 19A-19E, alternative embodiments of the locking fastener 30 may be used with any plate 10. The head portion 32 of the fastener 30 may include a textured area 36 in the form of a thread, for example, to lock the fastener 30 to the plate 10. The fastener 30 and/or plate 10 may also include one or more mechanisms to prevent back out of the fastener 30 from the plate 10. In FIG. 19A, the head portion 32 includes at threaded portion 36A (e.g., having straight threads) that interface with the plate 10 and the top of the head extends larger than the threads. The head portion 32 bottoms out when the fastener 30 is fully inserted and creates preload in the fastener 30, thus locking the fastener 30 rotationally. In FIG. 19B, the head portion 32 includes threaded portion 36B. The head portion 32 has a constant major diameter while the minor diameter is tapered. The thread depth may go to zero at the top of the head portion 32 of the screw 30. The first few turns smoothly insert, but as the tapered portion of the male thread engages with the plate 10, interference occurs, jamming and/or locking the screw 30 and preventing backout. In FIG. 19C, a screw thread 36C on the head portion 32, similar to the design in FIG. 19B, except the minor diameter of the screw 30 stays constant while the major diameter of the head portion 32 gets larger toward the top of the screw 30. A similar jamming and locking mechanism results through tightening of the screw 30 in the plate 10. In FIG. 19D, the threaded portion 36D has areas of varying pitch. In particular, a straight screw thread on the head portion 32 of the screw 30 has a similar pitch to that of the plate 10 at the bottom of the head portion 32 of the screw 30. The pitch then increases or decreases towards the top of the head portion 32, which thereby results in jamming of the threads and preventing unwanted backout of the screw 30. In an alternative variation of the concept of FIG. 19D, shown in FIG. 19E, the opening in the plate 10 is provided with areas of varying pitch while the pitch of the threaded portion 36D remains constant. For example, the head portion 32 may include a straight thread with a constant pitch. The upper surface of the plate 10 may include a thread pitch is similar to that of the screw 30, but towards the bottom surface of the plate 10, the thread pitch would either increase or decrease to lock the screw 30 to the plate 10.

Figure 20A:
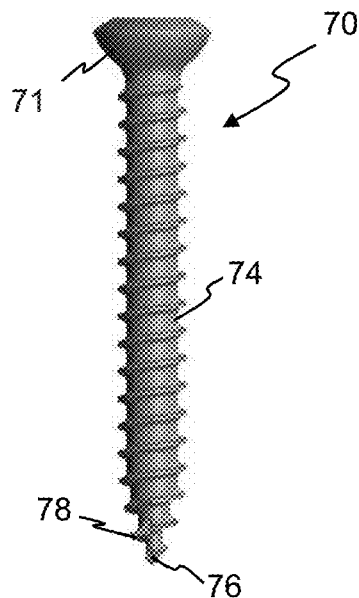
FIGS. 20A-20B show a self-drilling screw according to another embodiment.
Figure 20B:
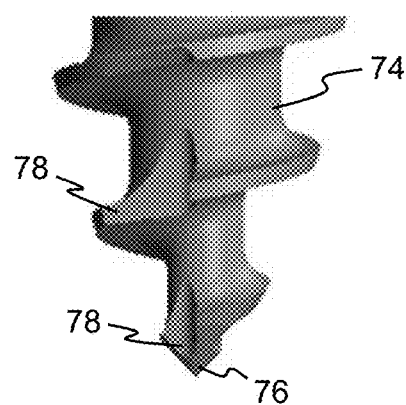

Turning now to FIGS. 20A and 20B, a self-drilling fastener 70, which may be utilized with any of the plates described herein, will be described. The self-drilling fastener 70 includes a head portion 71 and a shaft portion 74 configured to engage bone. The shaft portion 74 includes threads such that the fastener 70 may be threaded into the bone. The shaft portion 74 also includes a pointed tip 76 with cutting flutes 78. The pointed tip 76 and cutting flutes 78 allow the self-drilling fastener 70 to be inserted without a pre-drilled hole in the bone, thereby streamlining the insertion step. The head portion 71 of the self-drilling fastener 70 is substantially smooth around its outer surface such that it operates in a manner similar to the non-locking fasteners 40. It will be recognized that the head portion 71 of the fastener 70 may include a recess configured to receive a driver or the like. The self-drilling fasteners 70 may be manufactured from various materials, for example, stainless steel, titanium alloy, and cobalt chrome.

Figure 21A:
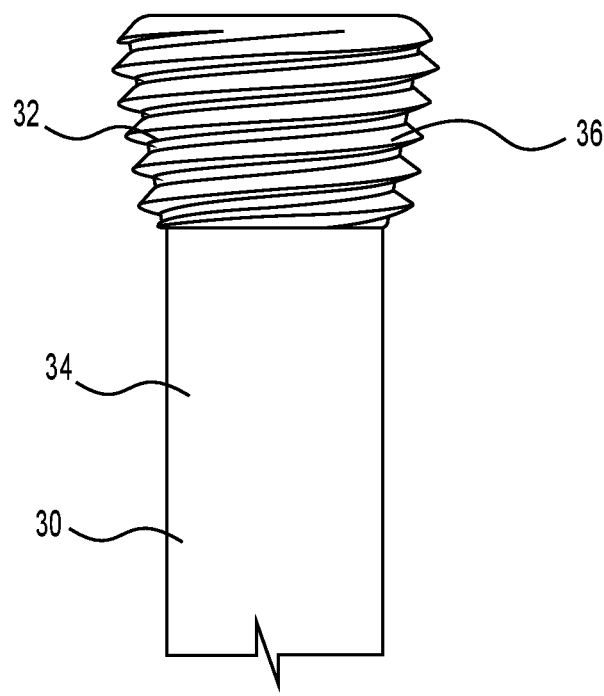
FIGS. 21A and 21B depict a fastener according to another embodiment with self-forming threads configured to form threads in the opening of a plate.
Figure 21B:
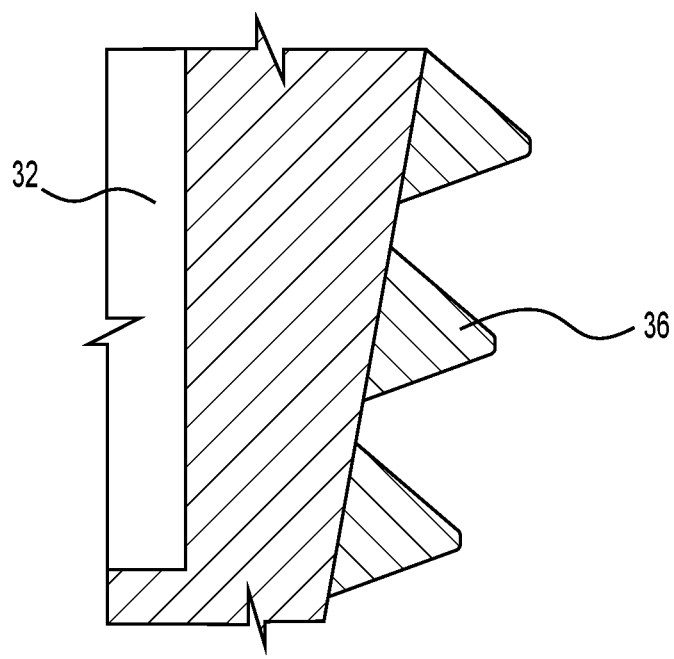
Figure 22A:
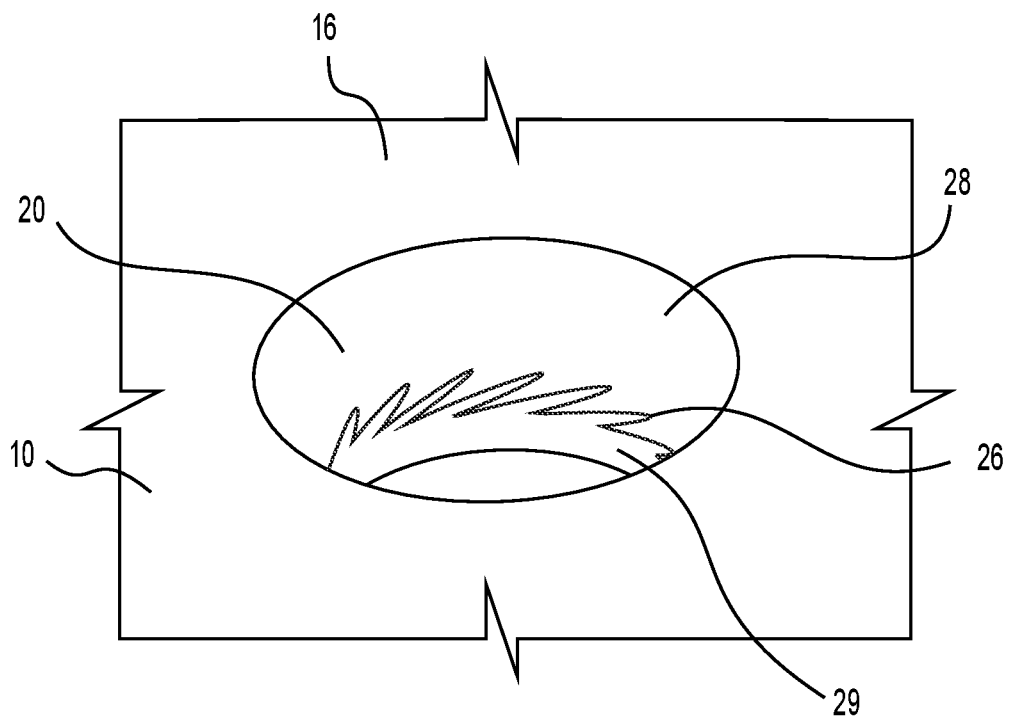
FIGS. 22A and 22B depict an opening in a plate according to one embodiment having a windswept cut configured to receive the self-forming threads of the fastener of FIGS. 21A-21B.
Figure 22B:
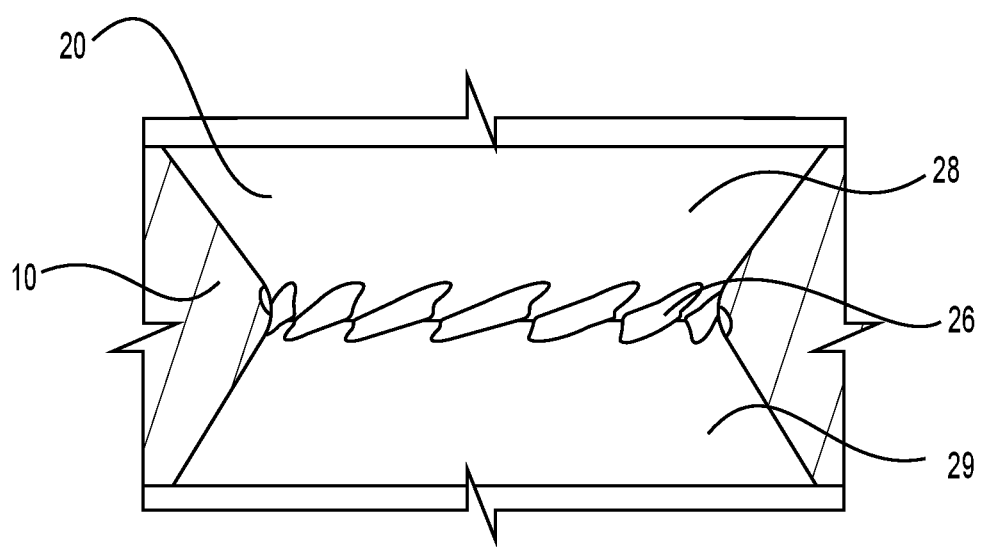

In FIGS. 21A-21B, the locking fastener 30 includes a head portion 32 and a shaft portion 34 configured to engage bone. Although not shown, the shaft portion 34 may be threaded such that the fastener 30 may be threaded into the bone. The head portion 32 may be tapered (e.g., at an angle of about 20°) such that the fit within the opening 20 in the plate 10 becomes tighter as the fastener 30 is advanced in to the bone. The head portion 32 of the locking fastener 30 includes a textured area 36 around its outer surface sized and configured to engage an opening 20 in the plate 10. The textured area 36 may include threads, ridges, bumps, dimples, serrations, or other types of textured areas. As shown, the textured area 36 preferably includes a threaded portion extending substantially from the top of the head portion 32 to the bottom of the head portion 32 proximate to the shaft portion 34. The threads 36 may run generally perpendicular to the conical surface of the head portion 32. The threaded portion 36 is in the form of self-forming threads configured to displace the plate material and create threads in the opening 20 of the plate 10. The threaded portion has an exaggerated sharp thread peak to facilitate cutting or forming of the plate material.

Turning now to FIGS. 22A-25B, alternative versions of the openings 20 are shown before being tapped with the fastener 30. Once the fastener 30 is inserted, these openings 20 are modified based on the self-forming threads. The geometry of the openings 20 are conducive to catching the threads 36 and designed to reduce the axial force necessary to initiate the thread formation. An upper portion of the hole 20 may be tapered 28, for example, with a conical straight tapered surface cut through the top surface 16 of the plate 10 for clearance of the head portion 32 of the fastener 30 during off angle insertion. A lower portion of hole 20 may further be tapered 29, for example, with a conical straight tapered surface cut through the bottom surface 18 of the plate 10 for clearance of the shaft portion 34 during off angle insertion. The upper tapered portion 28 may be larger, for example, with a larger degree of taper than the lower tapered portion 29. For example, the upper tapered portion 28 may have a taper in a range from about 60-90°, 70-80°, or 72-78°, preferably about 70°, 75°, or 80° whereas the lower tapered portion 29 may have a taper in a range from about 50-70°, 55-65°, or 57-63°, preferably about 55°, 60°, or 65°. The upper and/or lowered tapered portions 28, 29 may be substantially conical (e.g., FIG. 22B, 23B, 24B) or may be segmented with more than one section, such as two separate conical sections having different diameters or degrees of taper (e.g., FIGS. 25A and 25B).

At the intersection between the upper tapered portion 28 and the lower tapered portion 29 a narrowed central portion may have a textured portion 26. As described herein, the textured portion 26 may include threads, ridges, bumps, dimples, serrations, or other types of textured areas. In the embodiment shown in FIGS. 22A-22B, the textured portion 26 includes a windswept cut design comprised of a plurality of shallow cuts where each cut overlaps the next. For example, the windswept design may include a plurality of threadlike helical cut sweeps. Each cut has a smooth transition into the inner diameter of the hole 20 (e.g., into the upper and lower tapered portions 28, 29). The windswept cuts provide a positive surface for the self-forming threads to cut into, thereby helping to prevent peeling of the newly formed threads into the plate 10.

Figure 23A:
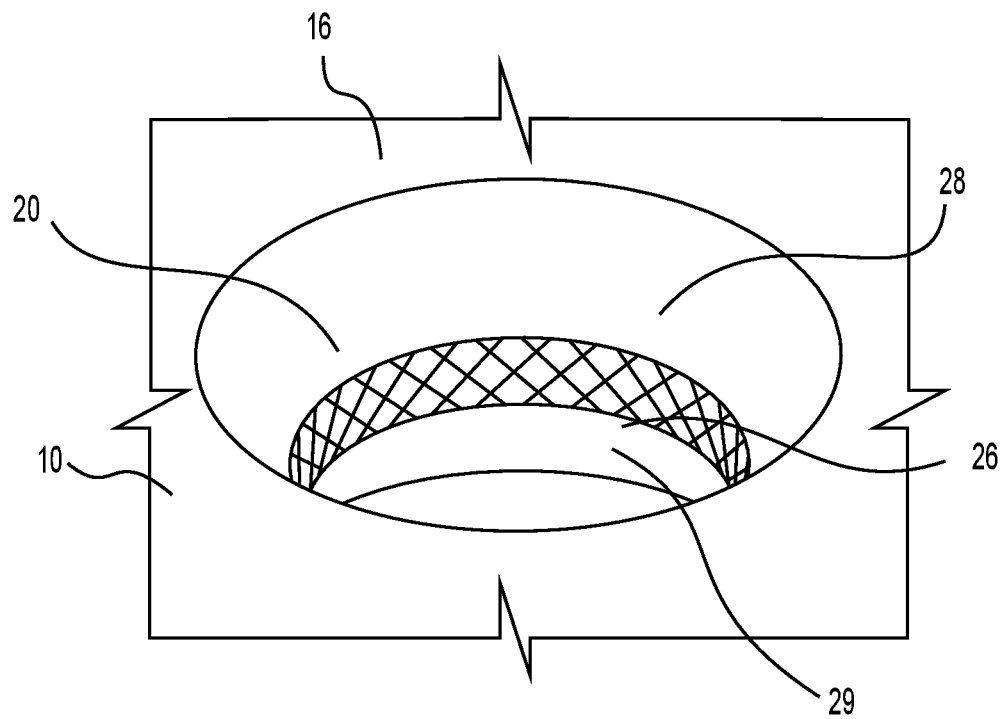
FIGS. 23A and 23B depict an opening in a plate according to another embodiment having a knurled cut configured to receive the self-forming threads of the fastener of FIGS. 21A-21B.
Figure 23B:
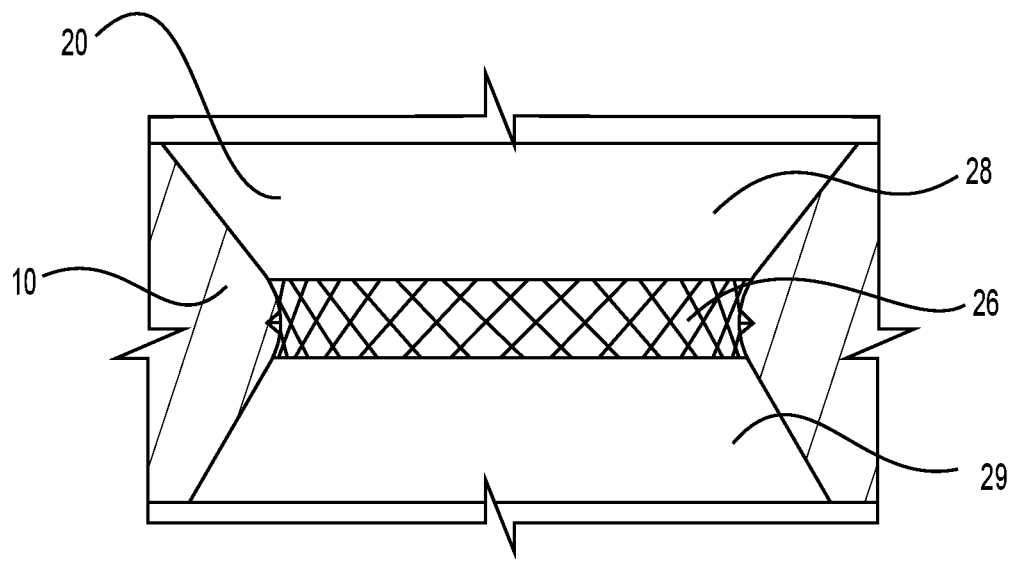
Figure 24A:
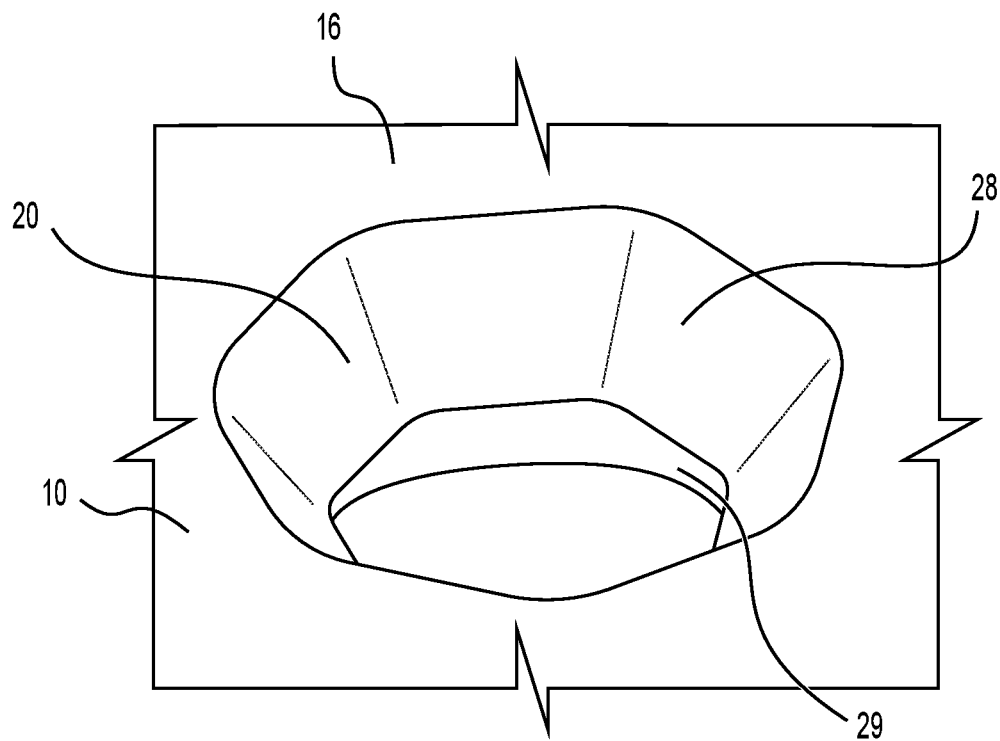
FIGS. 24A and 24B depict an opening in a plate according to another embodiment having a polygonal cut configured to receive the self-forming threads of the fastener of FIGS. 21A-21B.
Figure 24B:
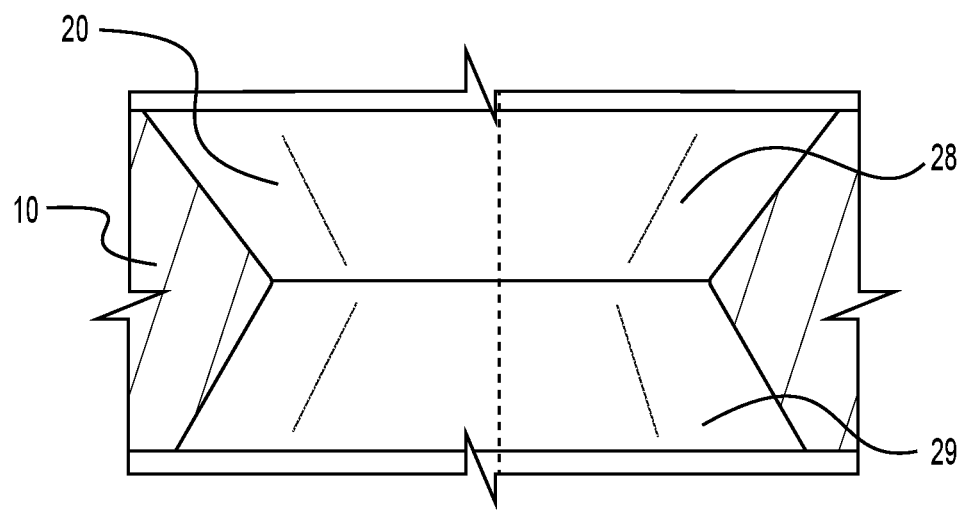

In FIGS. 23A-23B, the textured portion 26 includes a knurled cut design. A rounded transition between the upper tapered portion 28 and the lower tapered portion 29 (e.g., the two conical cuts) provides a workable surface for the knurling process as well as a surface for the head portion 32 to be able to roll over during off-axis locking. The knurled design may include a plurality of shallow knurled grooves set in a diamond pattern (e.g., about 45°) where each cut overlaps the next. The knurled grooves allow for the self-forming threads to cut more deeply into the material and reduce the necessary axial force to begin the thread forming process. FIGS. 24A-24B depict a polygon form cut design. In this design, there is no textured portion at the transition between the upper tapered portion 28 and the lower tapered portion 29. Instead, the narrowed central region has an overall polygonal form such that the hole 20 is neither cylindrical nor conical. The polygonal shape includes a number of sides with distinct linear section of material and rounded corners around which the form cut is allowed to sweep. For example, the polygonal shape may be substantially hexagonal (6-sided), heptagonal (7-sided), octagonal (8-sided), etc. The hole 20 may also be represented without lobe cuts, as a single concentric ring with the same geometry.

Figure 25A:
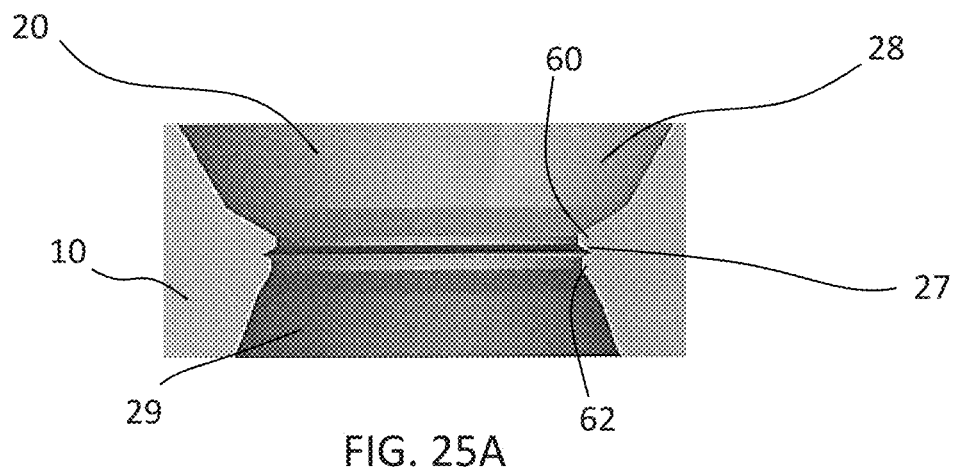
FIG. 25A depicts an alternative opening in a plate according to another embodiment.

In FIG. 25A, the upper tapered portion 28 includes a conical straight tapered surface cut for clearance of the head portion 32 of the fastener 30 during off angle insertion. The upper tapered portion 28 is segmented to have an upper area with a larger area relative to a lower area proximate the transition to the lower tapered portion 29 having a narrower diameter. The central area between the upper and lower tapered portions 28, 29, where the thread forming process occurs, includes two peaks or concentric rings of material (e.g., a superficial ring 60 and a deep ring 62) with a groove 27 being locating in between for material removal and thread forming relief. The groove 27 between the rings 60, 62 may be angled, for example, in the range of about 40-80°, about 50-70°, or about 60°. The superficial ring 60 is of a slightly smaller inner diameter than the deep ring 62, as the superficial ring 60 is responsible for supporting a majority of the cantilever loads. The deep ring 62 provides additional fixation and support during off-angle insertion as well as additional support during nominal trajectory insertion. The lower tapered portion 29 includes a straight tapered surface that provides clearance for the shaft 34 of the fastener 30 when inserted off angle.

Figure 25B:
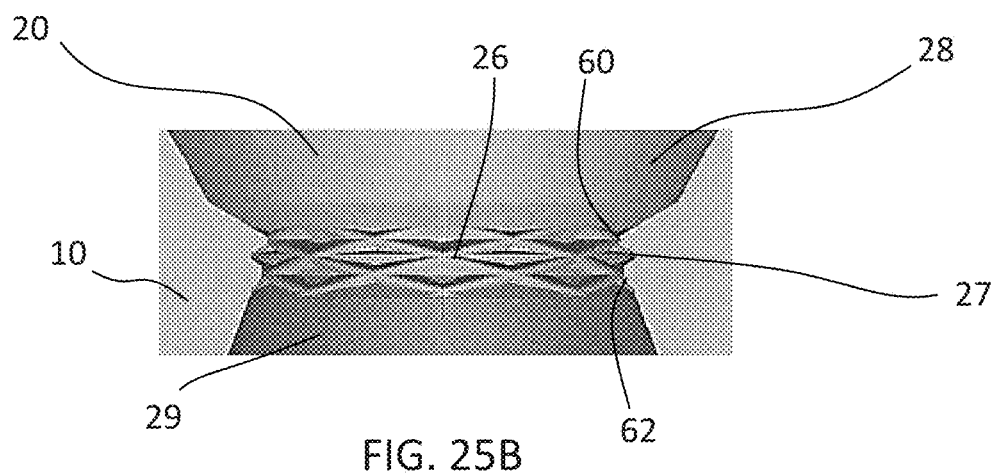
FIG. 25B depicts another alternative opening in a plate according to yet another embodiment.

The embodiment of the opening 20 in FIG. 25B is similar to FIG. 25A, but further includes textured portion 26 in the form of a plurality of helical swept cuts at the transition between the upper tapered portion 28 and the lower tapered portion 29. The shallow helical cuts or windswept cuts may include a series of cuts at a steep pitch. The windswept cuts may be angled, for example, at about 50-70°, or about 60°. The same number of cuts may be made in both a clockwise and counter-clockwise fashion. The cuts may create plateaus of material protruding into the opening 20. The resultant geometry provides positive surfaces for the fastener 30 to cut into, which can dramatically reduce the axial force necessary to lock the fastener 30 to the plate 10. Thus mechanism does not need to rely on bone purchase in order to engage the threads in the head portion 32 of the fastener 30. The material removed during insertion of the fastener 30 allows the self-forming threads to cut deeper by removing material which much be formed and reducing friction between the fastener 30 and the plate 10 during the forming process.

FIGS. 26A-26D depict a screw-plate assembly. The assembly, in FIG. 26C, shows the locking fastener 30 placed at an angle, other than perpendicular, to the upper surface 16 of the plate 10. In FIG. 26D, a non-locking fastener 40 is placed generally perpendicular to the plate 10. It will be appreciated that the locking fastener 30 and non-locking fastener 40 may be oriented at any appropriate angle relative to the plate 10. The section view in FIG. 26C shows the thread engagement with the plate 10 in which material of the plate 10 is displaced around the threads of the fastener 30. By using the self-forming threads, the fastener 30 is able to be inserted into the plate 10 at variable angles and engages with the plate 10 with one-step locking requiring no additional steps to lock the fastener 30 to the plate 10. The section view in FIG. 26D show the compressive, non-locking screw 40 received in the opening 20, without threadedly locking thereto. The non-locking screw 40 may provide for dynamic compression of the bone. Accordingly, the fasteners and openings described herein provide a wide variety of options for the surgeon, thereby providing appropriate locking and/or unlocking capability for dynamic compression depending on the desired treatment of the fracture and the bone.

Turning now to FIGS. 27A-35D, a series of trauma plates 10 and screws 30, 40 are shown which are configured for the fixation of fractures and fragments in diaphyseal and metaphyseal bone, for example. The different bone plates 10 and fasteners 30, 40 may be used in the treatment of various fractures.

FIGS. 27A-29J depict embodiments of straight plate offerings, which may be provided in a variety of lengths along with a variety of hole options and patterns. Additional features on these plates 10 may include k-wire holes 50, limiting contact undercut features 52, and/or tapered plate ends 12, 14.

FIGS. 27A-27E show an embodiment of a plate 10 with a dynamic compression plating (DCP) slot or elongated opening 20I. The DCP slot 20I allows motion of the plate 10 relative to the bone 2, 6. For example, a fracture 4 may separate bone into two bone fragments 2, 6, respectively. In order to move the bone fragments 2, 6 towards one another and minimize the fracture 4, plate 10 may be secured to bone 2 using non-locking fastener 40, for example. The shaft portion 44 of the fastener 40 may be driven into bone fragment 2. As depicted in FIGS. 27A-27C, by driving the non-locking fastener 40 into the bone 2, the plate 10 is able to move laterally, resulting in compression of the bone fracture 4. The DCP slot 20I may be elongated with a ramp 25 milled into the top surface 16 of the plate 10. The ramp 25 may span along the entire upper perimeter of the elongated slot 20I. An upper portion of the hole 20I may be tapered 28, for example, to form the ramp 25 or a portion thereof, a lower portion of hole 20I may further be tapered 29, and at the intersection between the upper tapered portion 28 and the lower tapered portion 29 a narrowed central portion may be configured to receive the head portion 42 of the non-locking fastener 40. As shown, the narrowed central portion may be downwardly curved such that the head portion 42 of the fastener 40 may be urged into the center of the slot 20I as the fastener 40 is secured further to the bone 2. Thus, as best seen in FIG. 27C, the fastener 40 is seated securely in the center of the slot 20I, thereby resulting in dynamic compression of the fracture 4.

FIGS. 28A-28E depict an embodiment of a plate 10 with a stacked hole 20J configured to receive a plurality of alternative screw offerings. The stacked holes 20J allow multiple screw options to be used in each hole location. In this embodiment, the hole 20J may be comprised of a conical chamfer 28 over top of a textured portion 26, for example, in the form of a conically threaded hole. The bottom of the hole 20J includes an additional conical chamfer 29 to allow for variable trajectories of the non-locking screws 40. The bottom conical chamfer 29 may be greater in diameter than the upper conical chamfer 28. The textured portion 26, or conically threaded hole, may be positioned closer to the top surface 16 of the plate 10, for example, such that the bottom conical chamfer 29 has a greater surface area than the upper conical chamfer 28.

Figure 3:
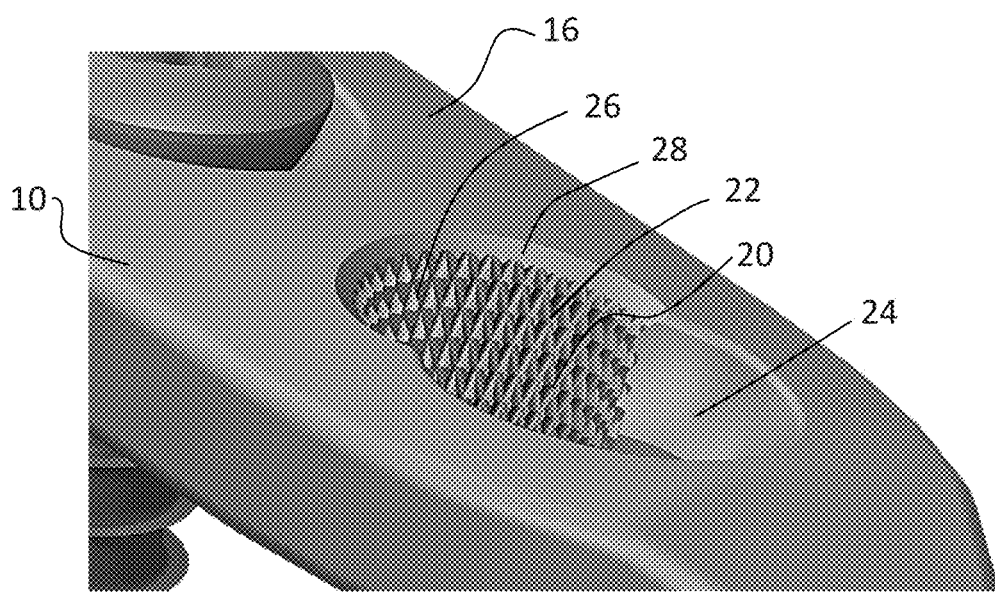
FIG. 3 is a close-up view of a combination hole according to one embodiment.

As best seen in FIGS. 28A-28C, a plurality of screw offerings is compatible with this hole 20J. For example, non-locking fasteners 40 and locking fasteners 30 may be used in hole 20J. FIG. 28A shows 3.5 mm non-locking screws and 4.0 mm cancellous bone screws in stacked hole 20J. FIG. 28B shows a 2.5 mm non-locking screw. Each of the non-locking screws are configured to interface with the top chamfer 28 of the hole as shown in FIGS. 28A and 28B, respectively. Locking fasteners 30 are also configured to interface with the conical threads of the hole 20J. As shown in FIG. 28C, 3.5 mm locking screws engage with the threaded hole portion of the stacked hole 20J. In other words, the threaded outer portion of the head portion 32 of the locking fastener 30 is configured to thread to the corresponding conical threads of the textured portion 26, thereby locking the fastener 30 to the plate 10.

Figure 29A:
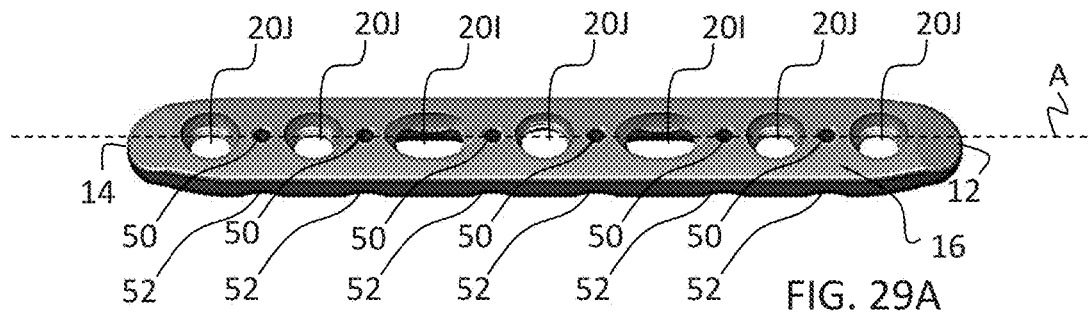
FIGS. 29A-29J show embodiments of straight plates and alternative hole configurations including dynamic compression slots; stacked holes and/or combination holes.
Figure 29B:
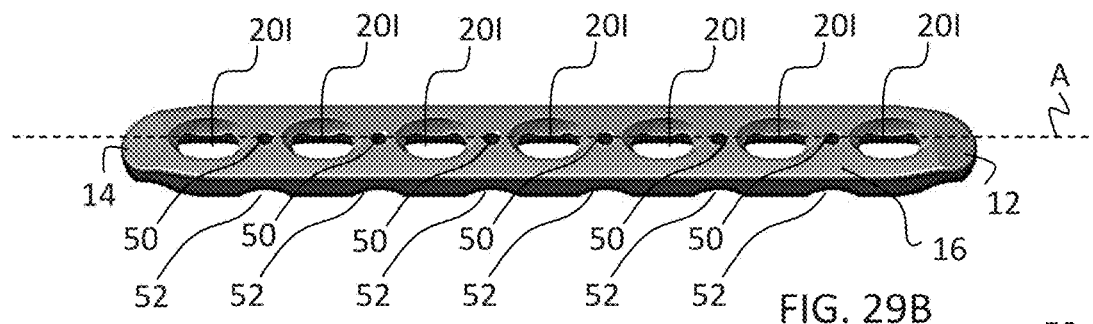
Figures 29C, 29D, 29E:
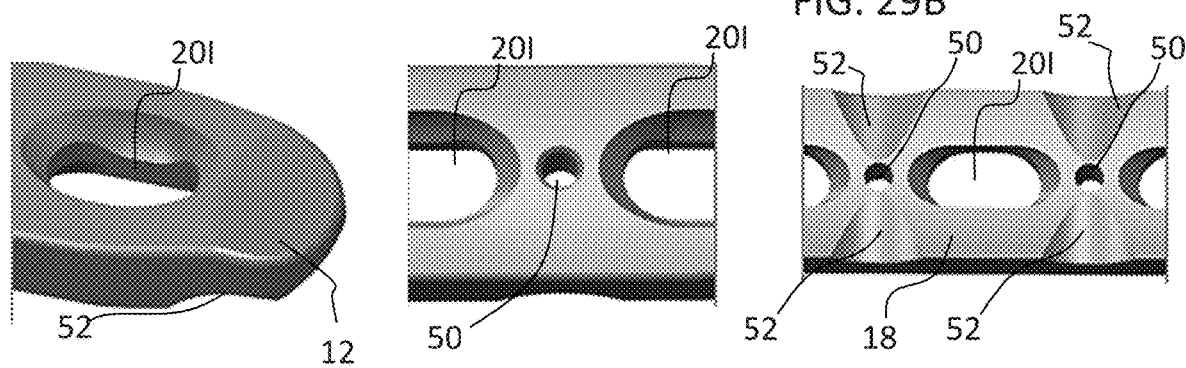
Figure 29F:
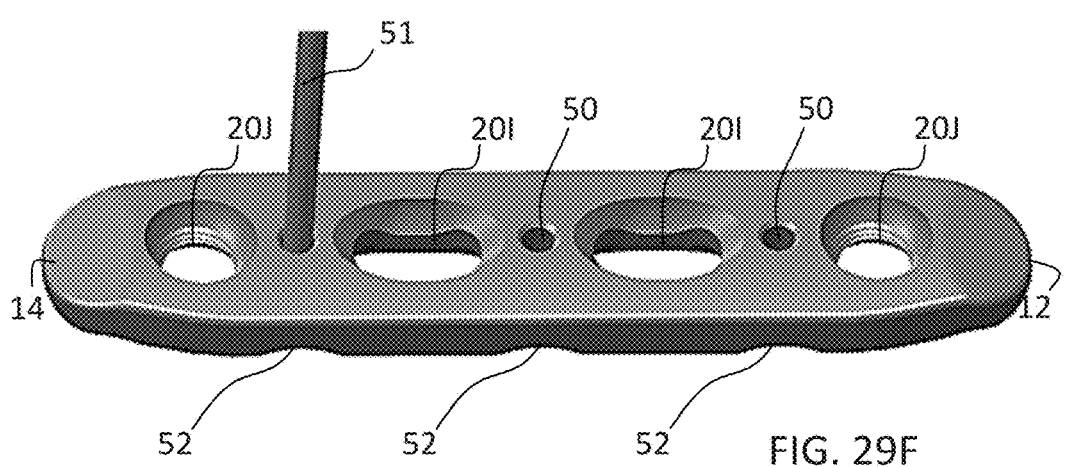

FIGS. 29A-29J depict alternative embodiments of plate offerings suitable for fixation of fractures and fragments in diaphyseal and metaphyseal bone. For example, FIG. 29A depicts one embodiment of a 3.5 mm straight plate 10 with a combination of DCP slots 20I and stacked holes 20J. FIG. 29B depicts a straight plate 10 with only DCP slots 20I positioned along the central longitudinal axis A of the plate 10. FIG. 29F shows an embodiment of a straight plate 10 with two central DCP slots 20I and stacked holes 20J at either end of the plate 10. The plate 10 may have a body that extends from a first end 12 to a second end 14 along central longitudinal axis A. The plate 10 includes a top surface 16 and an opposite, bottom surface 18 configured to contact adjacent bone. The top and bottom surfaces 16, 18 are connected by opposite side surfaces extending from the first to second ends 12, 14 of the plate 10. Although the plate 10 is shown having a generally longitudinal body, it will be appreciated that any suitable shape and contouring of the plate 10 may be provided depending on the location and type of fracture to be plated.

The plate 10 may comprise any suitable number and type of openings 20I, 20J in any suitable configuration. These openings 20I, 20J allow surgeons more flexibility for fastener placement, based on preference, anatomy, and fracture location. Surgeons may have differing opinions as to whether non-locking or locking screws 30, 40 (or some combination of the two) should be used. Further, complexity of fracture location and shape makes having as many locations for fasteners 30, 40 as possible necessary. This design offers surgeons a versatile method to achieve higher accuracy in placement of locking and/or non-locking screws 30, 40.

The plate 10 may have one or more additional features. For example, the plate 10 may include one or more through holes 50 extending through the plate 10. For example, holes 50 may extend from the top surface 16 to the bottom surface 18 of the plate 10. These holes 50 may be configured to receive k-wires, for example, k-wire 51 shown in FIG. 29F. In the embodiments shown, k-wire holes 50 are provided along the central longitudinal axis A of the plate 10 alternating between each of the respective fastener openings 20I, 20J. Although it will be appreciated that any number and location of holes 50 may be provided for receiving k-wires. The k-wire holes 50 offer an additional point of fixation for the plate 10. Driving a k-wire 51 through the appropriate hole in the plate 10 allows the plate 10 to be held on the bone while adjacent bone screws 30, 40 can be inserted.

The plate 10 may also include one or more tapers or reliefs to minimize contact of the plate 10 with the bone and preserve the anatomy. The plate 10 may include one or more tapered ends 12, 14. The tapered ends 12, 14 of the plate 10 may be configured to provide sub-muscular insertion during minimally invasive procedures. The reliefs may also be in the form of one or more conical cuts 52 along the bottom surface 18 of the plate 10. The conical cuts 52 may be positioned on either side of the k-wire holes 50 and extend outward towards the side surfaces of the plate 10. Each conical cut 52 may include a narrowed portion proximate to the k-wire hole 50 (e.g., along the central longitudinal axis A of the plate 10) and a widened portion proximate to the outer side surfaces. The limited contact undercuts 52 may minimize the plate contact with the bony anatomy in an effort to preserve the blood supply to the bone and the surrounding soft tissues.

Referring to FIGS. 29G-J, each of the straight plates 10 illustrated therein have beveled ends 12, 14, with both the top and bottom surfaces 16, 18 having sloped portions 17, 19 to the tip of the respective end 12, 14. As in the previous embodiment, the beveled ends 12, 14 of the plate 10 may be configured to provide sub-muscular insertion during minimally invasive procedures. Additionally, each of plates 10 has a scalloped central portion 21 on the underside 18 of the plate 10. The scalloped central portion 21 extends substantially the length of the plate 10 and acts to limit contact between the plate 10 and the bone to preserve the anatomy.

Figure 29G:
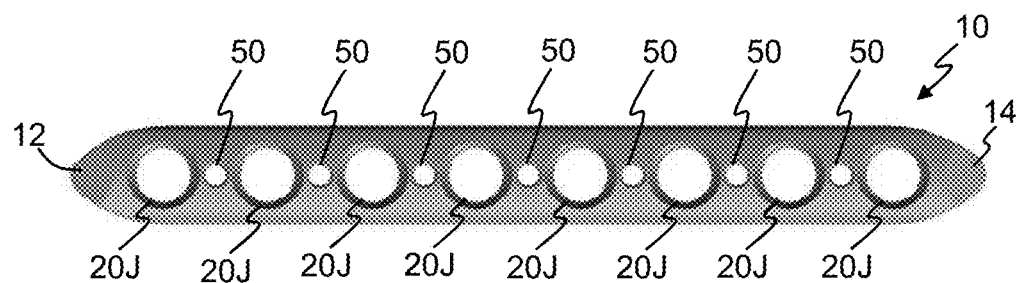
Figure 29H:
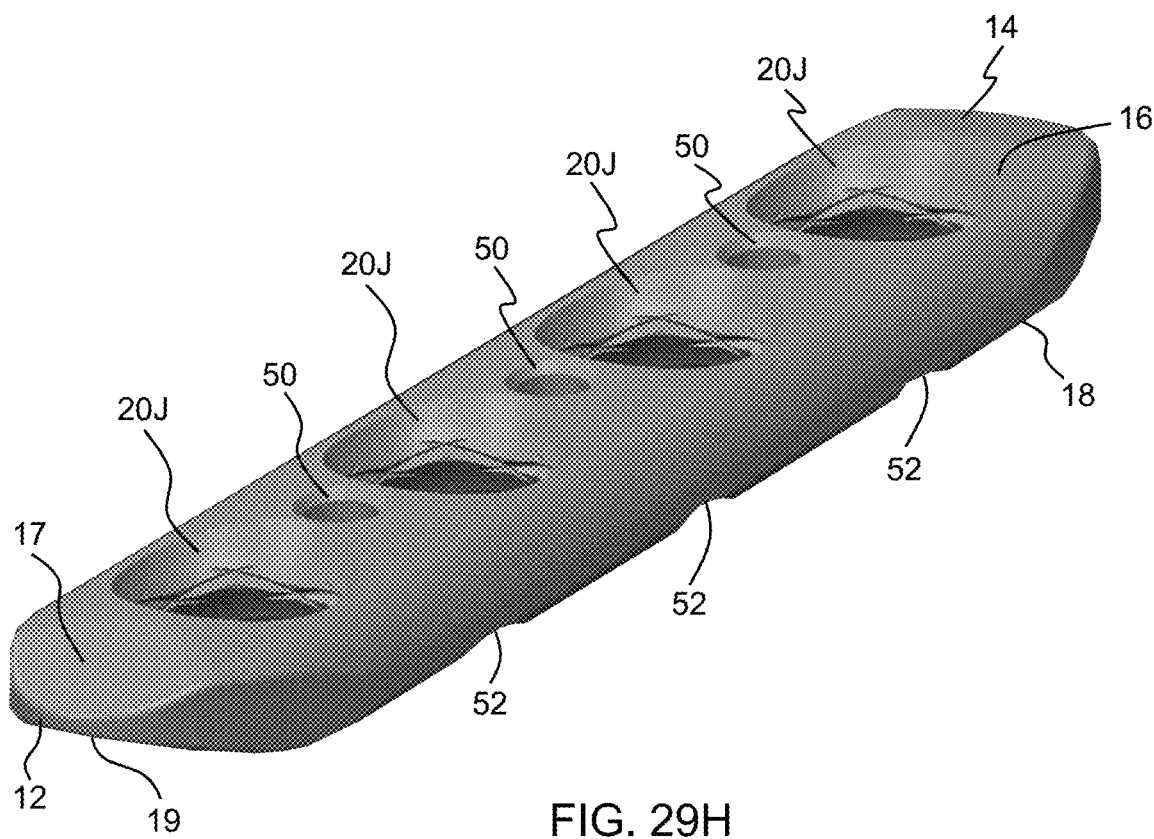
Figure 29I:
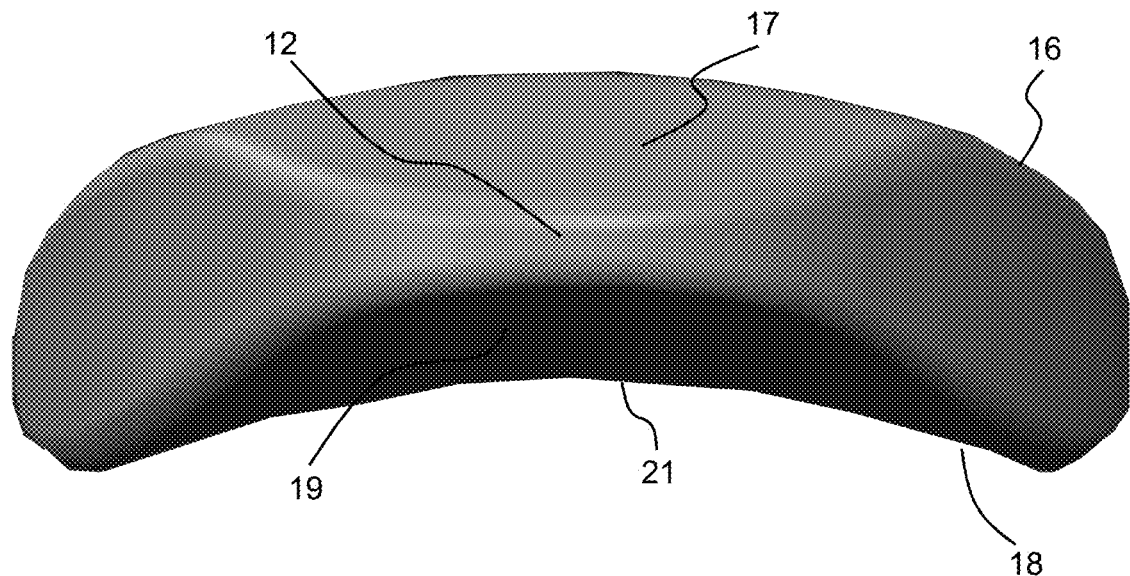
Figure 29J:
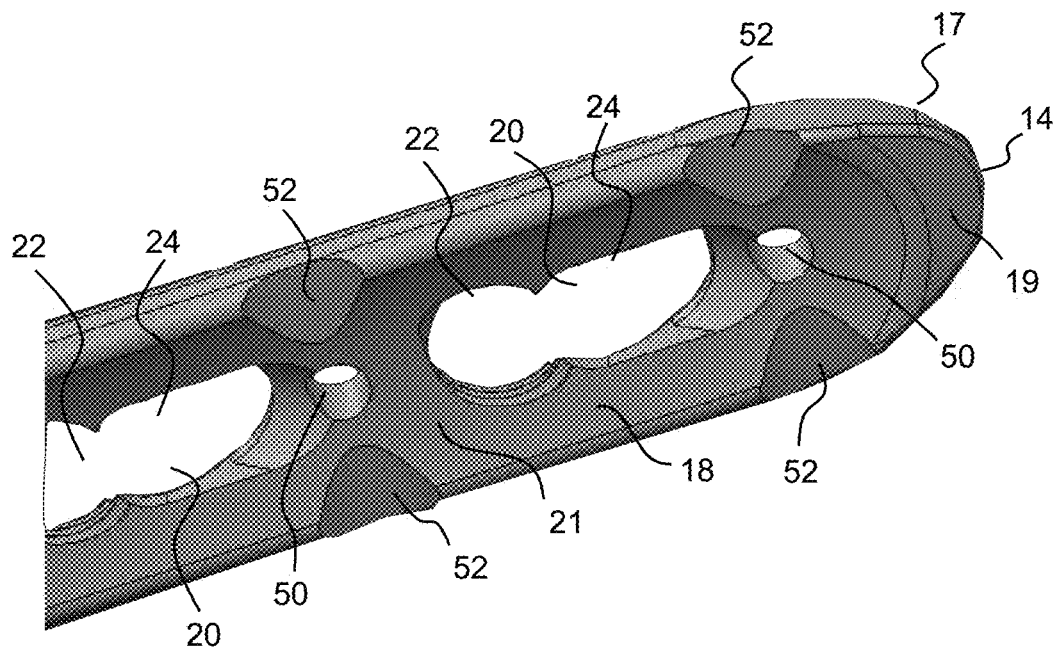

The straight plates 10 illustrated in FIGS. 29G and 29H each have a plurality of stacked holes 20J alternating with k-wire holes 50. The plate 10 illustrated in FIG. 29J has a plurality of combination holes 20 with overlapping locking holes 22 and dynamic holes 24. In at least one embodiment, the plates 10 include either all stacked holes 20J, all locking holes 22, all DCP slots 20I, all combination holes 20, or a combination of stacked holes 20J and DCP slots 20I. Additionally, in at least one embodiment, all of the holes of the straight plate 10 have the same diameter such that they may all be utilized with screws, whether locking screws 30, non-locking screws 40 or self-drilling screws 70, all having the same diameter. While straight plates 10 having specific hole combinations and diameters are described, the disclosure is not limited to such, and the straight plates 10 may have any desired combination of the various holes described herein in any combination of diameters.

Figure 30A:
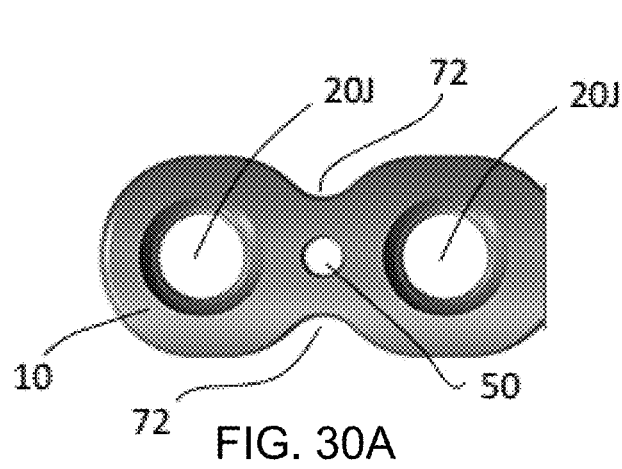
FIGS. 30A-30I depict alternative embodiments of reconstruction plates with alternative hole patterns.
Figure 30B:
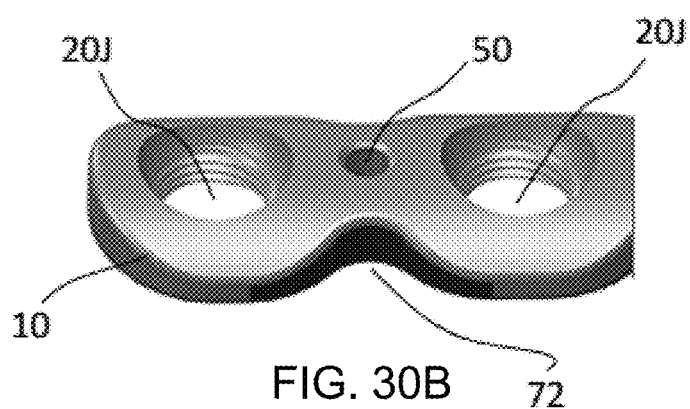
Figure 30C:
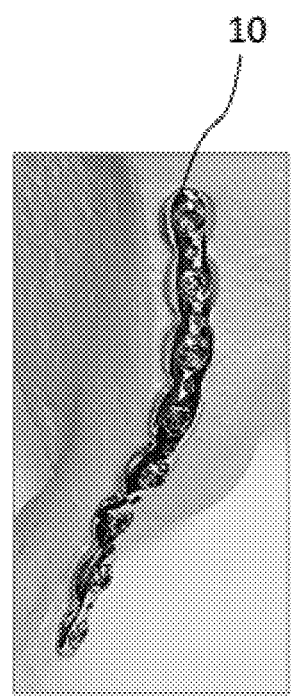
Figure 30D:
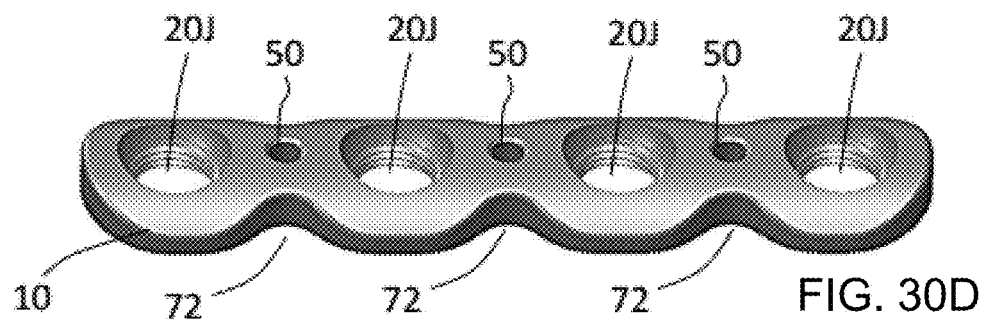
Figure 30E:
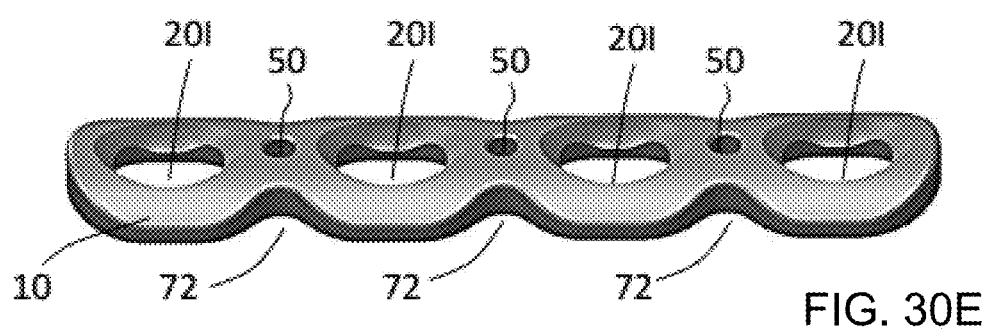
Figure 30F:
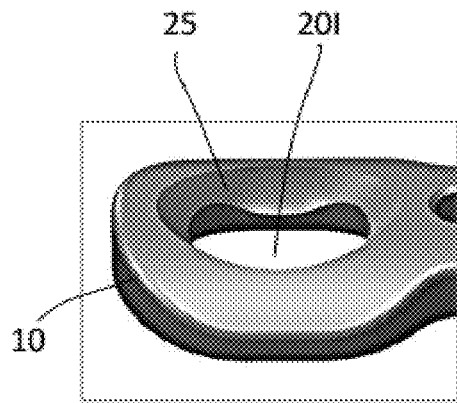
Figure 30G:
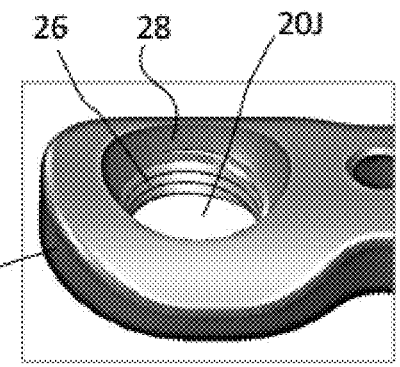

Turning now to FIGS. 30A-30I, reconstruction (recon) plates 10 may be offered in a variety of lengths along with a variety of hole options. The reconstruction plate 10 includes a plurality of side relief cuts 72 along the length of the plate 10, which allow the plate 10 to be bent, for example, in three dimensions. The side relief cuts 72 may be in the form of one or more curves having a widened portion along the sides of the plate 10 and a narrowed portion towards the center of the plate 10. The side relief cuts 72 may be positioned in line and on opposite sides of each of the k-wire holes 50, for example. The plurality of relief cuts 72 may form a scalloped or wavy profile along the side edges of the plate 10. As best seen in FIG. 30C, the plate 10 is able to be shaped to a multi-contour surface as a result. FIGS. 30E and 30F show an embodiment of a plate 10 with dynamic compression plating (DCP) slots or elongated openings 20I, similar to the DCP slots 20I shown in FIG. 27D. FIGS. 30D and 30G-I depict embodiments of a plate 10 with stacked holes 20J, similar to stacked holes 20J in FIG. 23A or FIG. 28D.

Figure 30H:
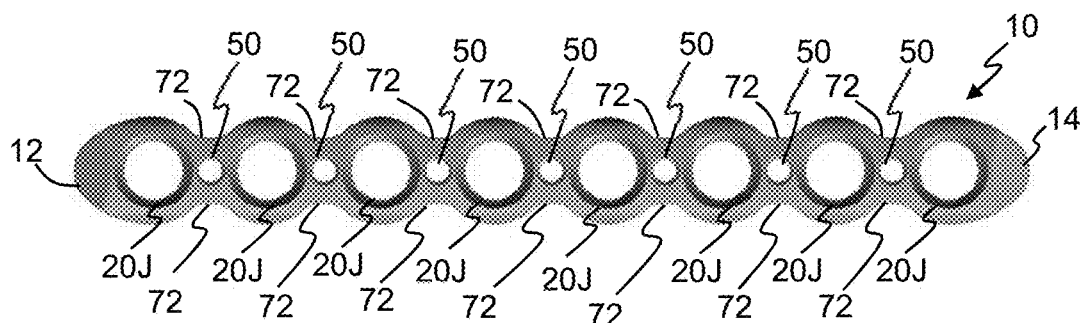
Figure 30I:
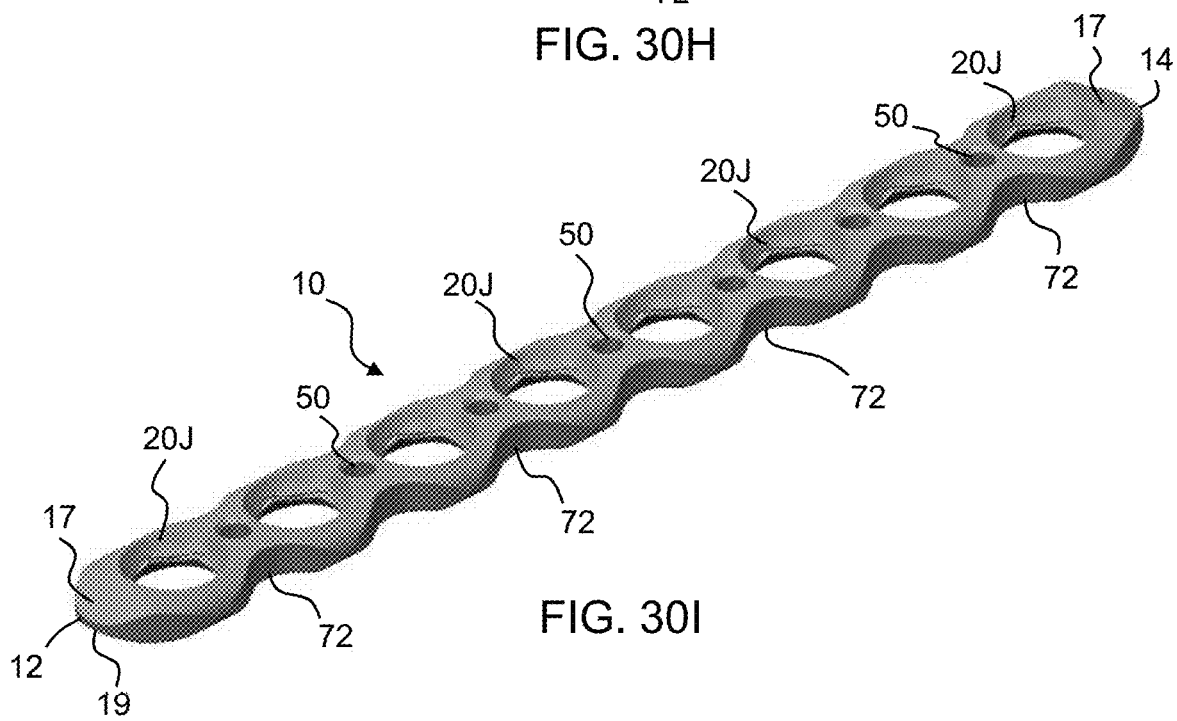

The plate 10 illustrated in FIGS. 30H and 30I also includes beveled ends 12, 14 and a scalloped underside similar to that described with respect to the plate 10 in FIGS. 29G-29J. In at least one embodiment, the plates 10 include either all stacked holes 20J, all locking holes 22, all DCP slots 20I, or all combination holes 20. Additionally, in at least one embodiment, all of the holes of the reconstruction plate 10 have the same diameter such that they may all be utilized with screws, whether locking screws 30, non-locking screws 40 or self-drilling screws 70, all having the same diameter. While reconstruction plates 10 having specific hole combinations and diameters are described, the disclosure is not limited to such, and the reconstruction plates 10 may have any desired combination of the various holes described herein in any combination of diameters.

FIGS. 31A-31G provide embodiments of T-plates 10, which may be available in a variety of lengths along with a variety of hole options. The T-plates 10 have a body with a substantially "T" shaped profile. The T-plates 10 have an elongate portion extending along the longitudinal axis A of the plate 10 from the first end 12 of the body and a transverse cross-portion at the second end 14 of the body. The transverse cross-portion may include one or more wings or extensions 80 extending from the elongate portion of the plate 10. The extensions 80 may each be perpendicular to or at an angle slightly greater than 90° relative to the longitudinal axis A of the plate 10. The "T" shaped profile provides a greater screw density and is configured to capture fractures most often located near periarticular surfaces.

Figure 31A:
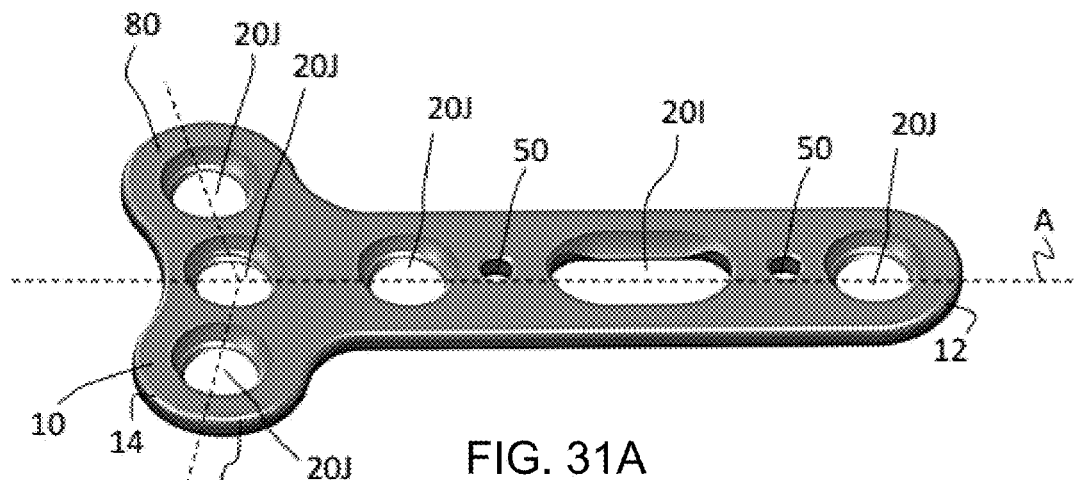
FIGS. 31A-31G show embodiments of T-plates with alternative hole arrangements.
Figure 31B:
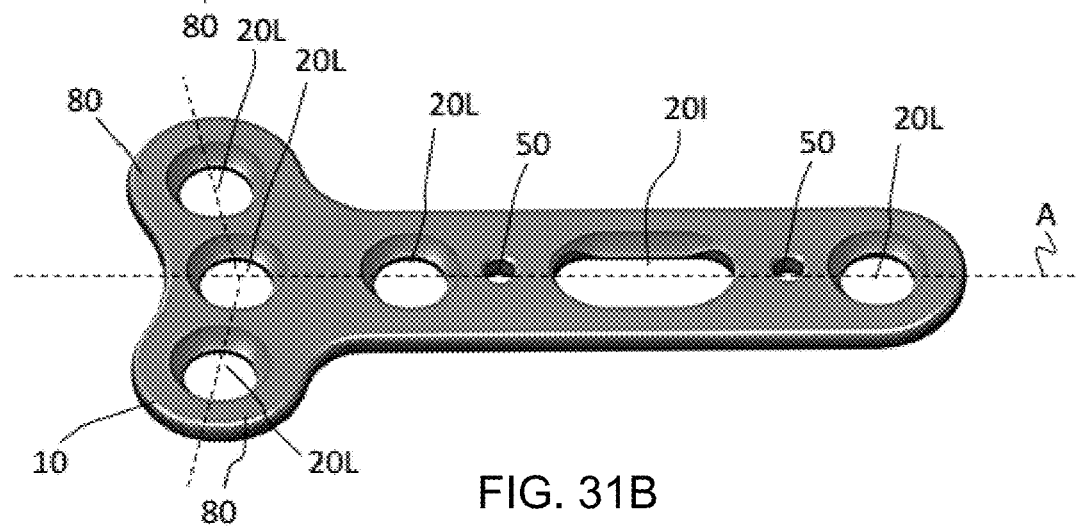
Figure 31C:
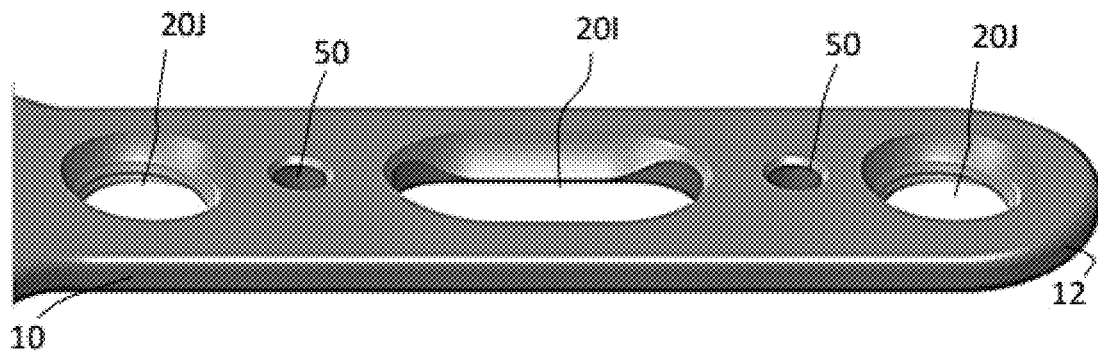
Figure 31D:
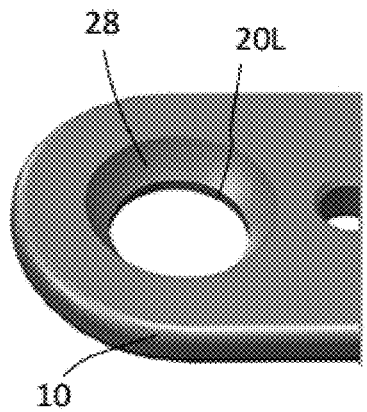
Figure 31E:
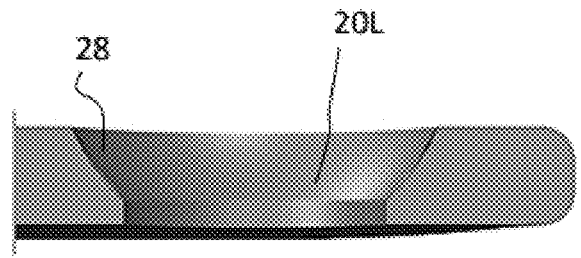

FIG. 31A depicts a T-plate 10 with a DCP slot 20I flanked on either side by stacked holes 20J on the elongate portion of the plate 10. The cross-portion also includes stacked holes 20J offset from one another. A first stacked hole 20J may be in line with the longitudinal axis A of the plate. A second stacked hole 20J may be positioned in the first extension 80, and a third stacked hole 20J may be positioned in the second extension 80. FIG. 31B depicts another embodiment of the T-plate 10 with the same configuration as FIG. 31A having the non-locking holes 20L substituted for each of the stacked holes 20J. FIGS. 31D-31E show a non-locking hole 20L in the form of a cylindrical hole with a top chamfer 28 configured to be compatible with non-locking fasteners 40, including the 2.5 mm and 3.5 mm non-locking screws and the 4.0 mm cancellous screw. The chamfer or tapered portion 28 narrows towards the bottom of the hole 20L. These non-locking holes 20L may be substitute for any of the other slots or holes 20I, 20J in the plate 10.

Figure 31F:
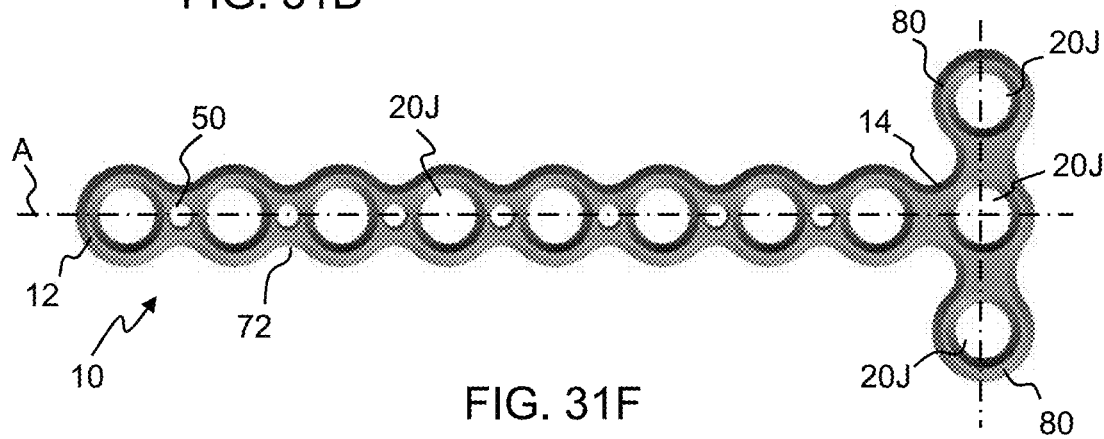
Figure 31G:
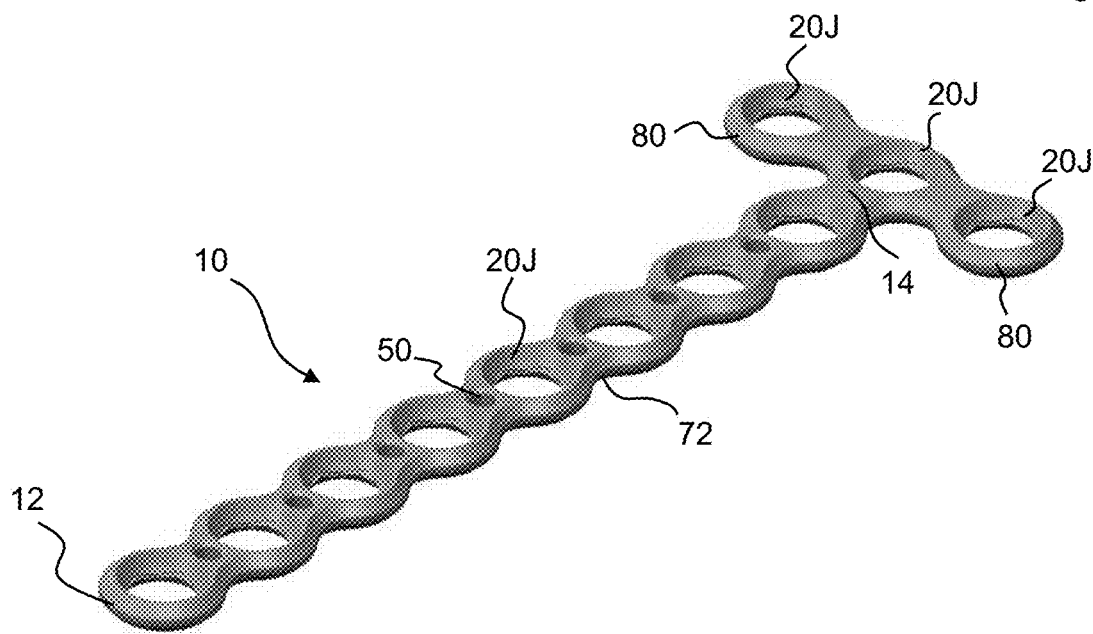

The plate 10 illustrated in FIGS. 31F and 31G also includes a beveled end 12 and a scalloped underside similar to that described with respect to the plate 10 in FIGS. 29G-29J. In at least one embodiment, the T-plate 10 includes either all stacked holes 20J, all locking holes 22, a combination of stacked holes 20J and DCP slots 20I, or a combination of stacked holes 20J and combination holes 20. Additionally, in at least one embodiment, all of the holes of the T-plate 10 have the same diameter such that they may all be utilized with screws, whether locking screws 30, non-locking screws 40 or self-drilling screws 70, all having the same diameter. While T-plates 10 having specific hole combinations and diameters are described, the disclosure is not limited to such, and the T-plates 10 may have any desired combination of the various holes described herein in any combination of diameters.

Figure 32A:
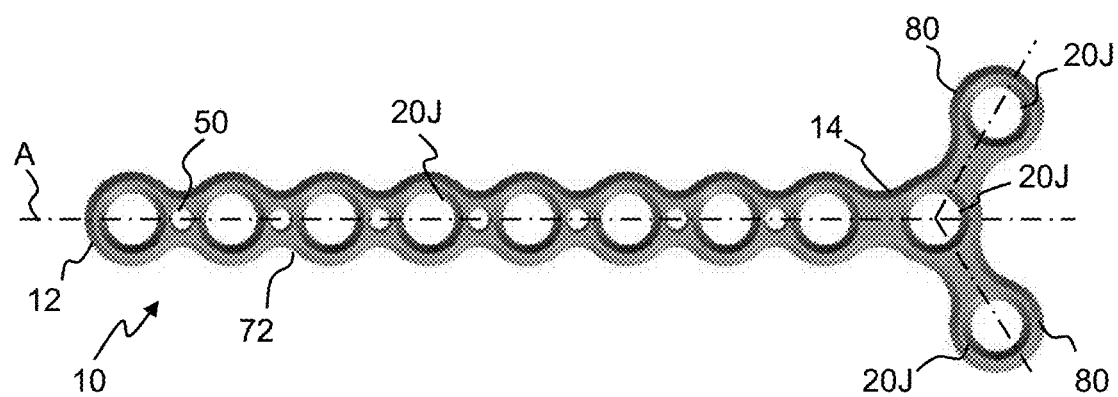
FIGS. 32A-32B show an embodiment of an illustrative Y-plate.
Figure 32B:
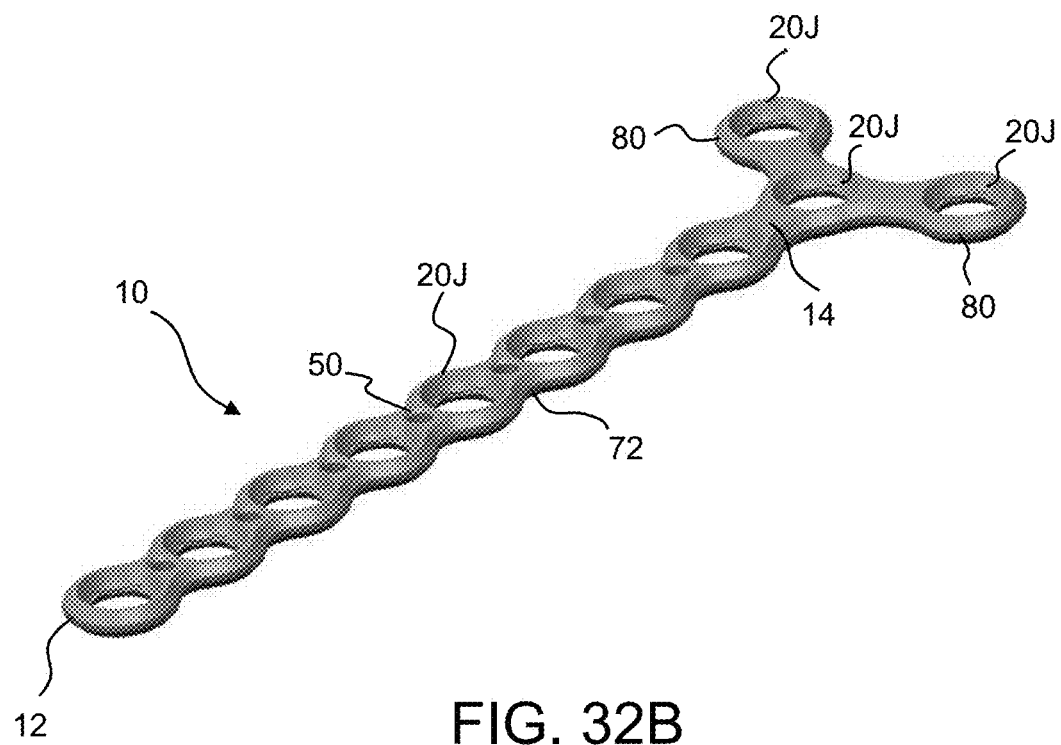

FIGS. 32A-32B provide embodiments of Y-plates 10, which may be available in a variety of lengths along with a variety of hole options. The Y-plates 10 have a body with a substantially "Y" shaped profile. The Y-plates 10 have an elongate portion extending along the longitudinal axis A of the plate 10 from the first end 12 of the body and a pair of diverging wings or extensions extending from the second end 14 of the body. The extensions 80 are each at an acute angle relative to the longitudinal axis A of the plate 10. The "Y" shaped profile provides a greater screw density and is configured to capture fractures most often located near periarticular surfaces.

The plate 10 illustrated in FIGS. 32A and 32B also includes a beveled end 12 and a scalloped underside similar to that described with respect to the plate 10 in FIGS. 29G-29J. The plate 10 may also include k-wire holes 50. In at least one embodiment, the Y-plate 10 includes either all stacked holes 20J, all locking holes 22, a combination of stacked holes 20J and DCP slots 20I, or a combination of stacked holes 20J and combination holes 20. Additionally, in at least one embodiment, all of the holes of the Y-plate 10 have the same diameter such that they may all be utilized with screws, whether locking screws 30, non-locking screws 40 or self-drilling screws 70, all having the same diameter. While Y-plates 10 having specific hole combinations and diameters are described, the disclosure is not limited to such, and the Y-plates 10 may have any desired combination of the various holes described herein in any combination of diameters.

Figure 33A:
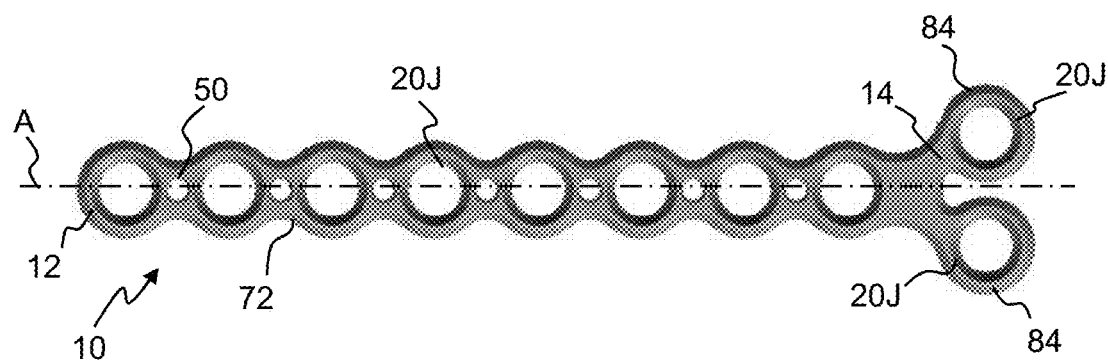
FIGS. 33A-33B show an embodiment of an illustrative condylar plate.
Figure 33B:
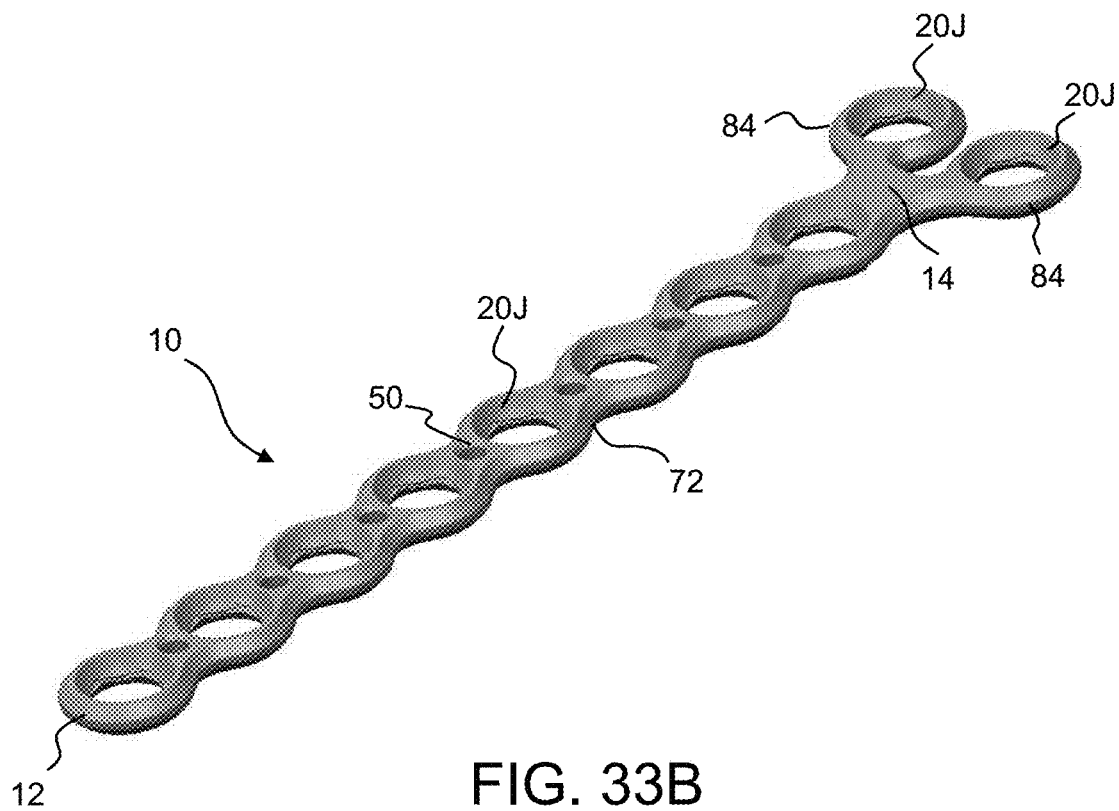

FIGS. 33A-33B provide embodiments of condylar plates 10, which may be available in a variety of lengths along with a variety of hole options. The condylar plates 10 have an elongate portion extending along the longitudinal axis A of the plate 10 from the first end 12 of the body and a pair of ears 84 extending from the second end 14 of the body. The ears 84 are each at slight angle relative to the longitudinal axis A of the plate 10, however, each extends proximate to the longitudinal axis A such that there is a space less than the width of the body. The configuration provides for greater contouring of the end 14.

The plate 10 illustrated in FIGS. 33A and 33B also includes a beveled end 12 and a scalloped underside similar to that described with respect to the plate 10 in FIGS. 29G-29J. The plate 10 may also include k-wire holes 50. In at least one embodiment, the condylar plate 10 includes either all stacked holes 20J, all locking holes 22, a combination of stacked holes 20J and DCP slots 20I, or a combination of stacked holes 20J and combination holes 20. Additionally, in at least one embodiment, all of the holes of the condylar plate 10 have the same diameter such that they may all be utilized with screws, whether locking screws 30, non-locking screws 40 or self-drilling screws 70, all having the same diameter. While condylar plates 10 having specific hole combinations and diameters are described, the disclosure is not limited to such, and the condylar plates 10 may have any desired combination of the various holes described herein in any combination of diameters.

Figure 34A:
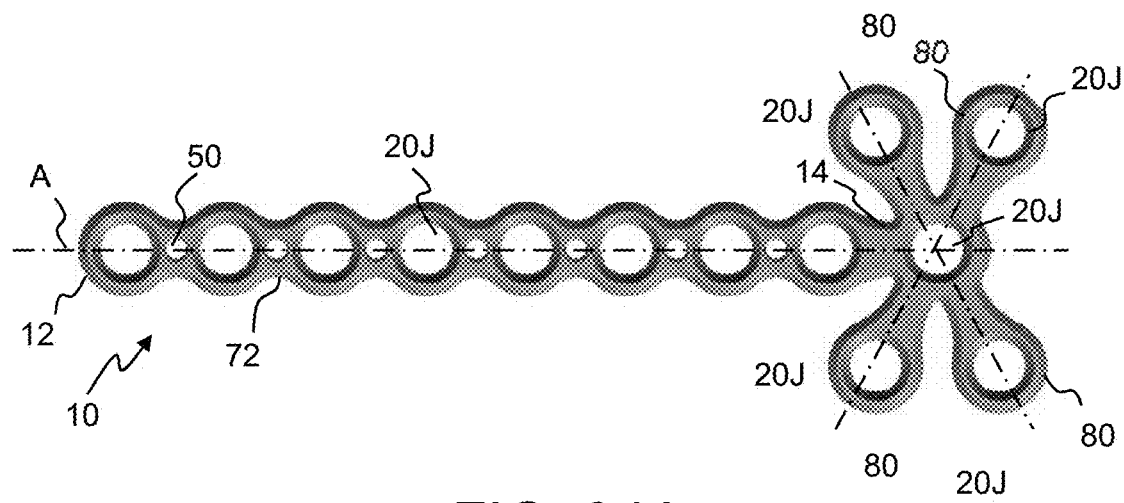
FIGS. 34A-34B show an embodiment of an illustrative X-plate.
Figure 34B:
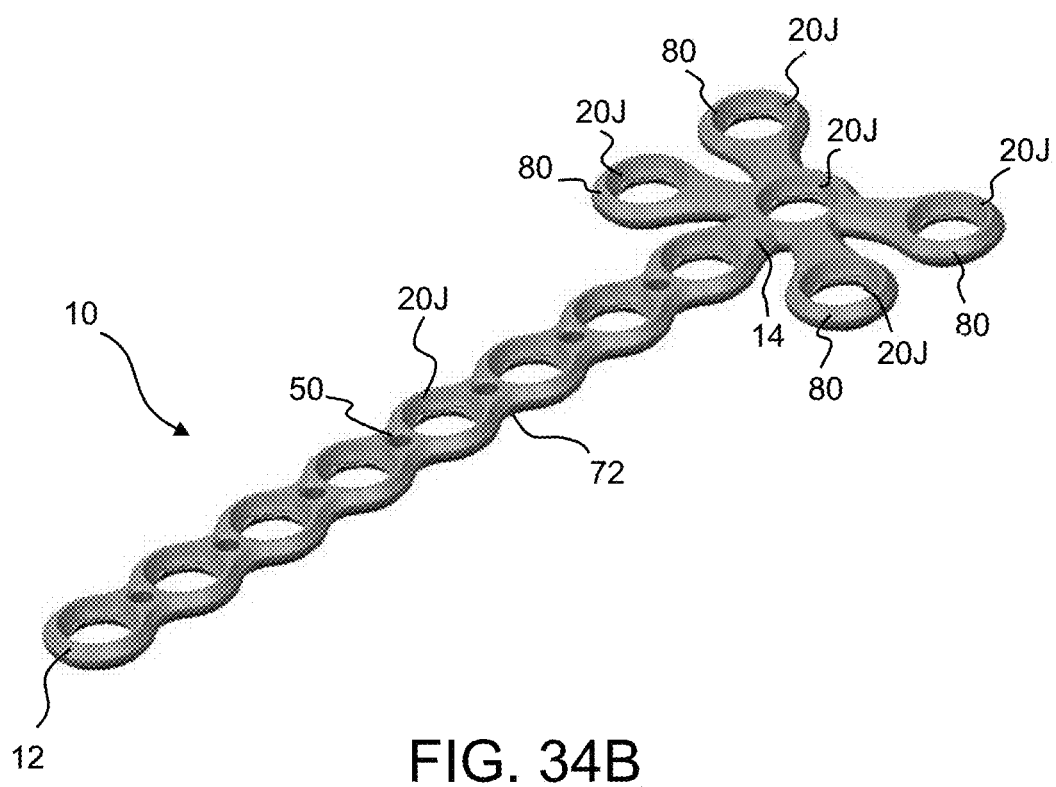

FIGS. 34A-34B provide embodiments of X-plates 10, which may be available in a variety of lengths along with a variety of hole options. The X-plates 10 have a body with an elongate portion extending along the longitudinal axis A of the plate 10 from the first end 12 of the body and a clustered 5-hole head at the second end 14 of the body. The clustered head is defined by four extensions 80 extending from the end 14 of the body in an X configuration. The "X" shaped profile provides a greater screw density and is configured to capture fractures most often located near periarticular surfaces.

The plate 10 illustrated in FIGS. 34A and 34B also includes a beveled end 12 and a scalloped underside similar to that described with respect to the plate 10 in FIGS. 29G-29J. The plate 10 may also include k-wire holes 50. In at least one embodiment, the X-plate 10 includes either all stacked holes 20J, all locking holes 22, a combination of stacked holes 20J and DCP slots 20I, or a combination of stacked holes 20J and combination holes 20. Additionally, in at least one embodiment, all of the holes of the X-plate 10 have the same diameter such that they may all be utilized with screws, whether locking screws 30, non-locking screws 40 or self-drilling screws 70, all having the same diameter. While X-plates 10 having specific hole combinations and diameters are described, the disclosure is not limited to such, and the X-plates 10 may have any desired combination of the various holes described herein in any combination of diameters.

Figure 35A:
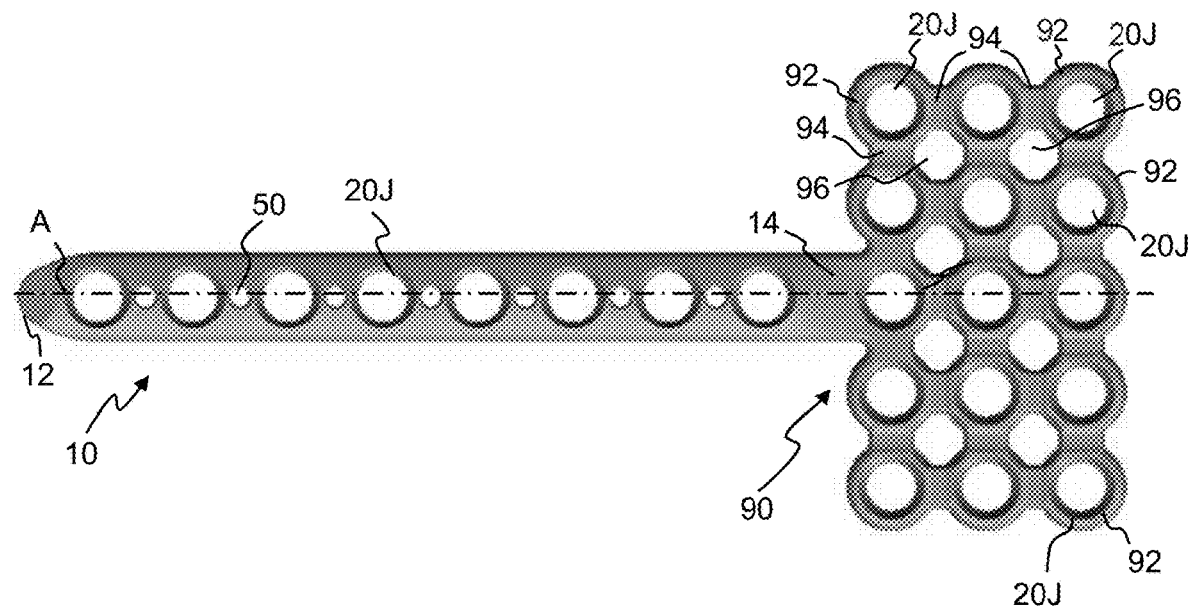
FIGS. 35A-35B show an embodiment of an illustrative cluster plate.
Figure 35B:
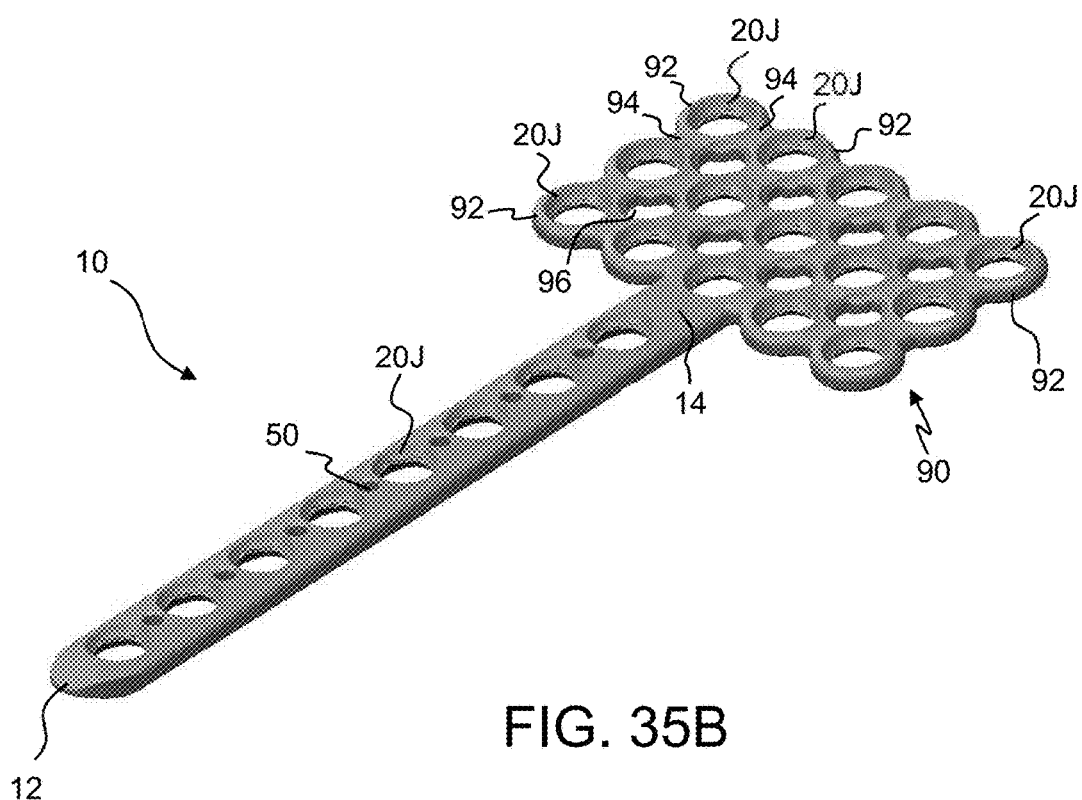

FIGS. 35A-35B provide embodiments of cluster plates 10, which may be available in a variety of lengths along with a variety of hole options. The cluster plates 10 have a body with an elongate portion extending along the longitudinal axis A of the plate 10 from the first end 12 of the body and a clustered mesh head 90 at the second end 14 of the body. The plate 10 includes a beveled end 12 and a scalloped underside similar to that described with respect to the plate 10 in FIGS. 29G-29J. The plate 10 may also include k-wire holes 50. The elongate body provides the strength of the straight plates described above while the mesh head 90 allows for significant customization.

The mesh head 90 is defined by a plurality of holes 20, in the illustrated embodiment stacked holes 20J, each with a rim 92 thereabout. The rims 92 of adjacent holes 20 are interconnected to one another via bridge portions 94 with through spaces 96 also provided between groups of holes 20. The bridge portions 94 are preferably thinner than the rims 92. The rims 92 preferably have a thickness equal to or less than the thickness of the elongate body. The thinner configuration of the bridge portions 94 along with the through spaces 96 allow the mesh head 90 to be easily contoured. Additionally, the mesh head 90 may be cut along the bridge portions 94 to shape the mesh head 90 to achieve a desired shape or size. The illustrated mesh head 90 has a 3×5 hole arrangement defining a rectangular configuration, however, the disclosure is not limited to such. The mesh head 90 may have various numbers of holes 20 which may be arranged in various configurations including, for example, square, rectangular or round (similar to mesh plate 100 illustrated in FIG. 36A).

In at least one embodiment, the cluster plate 10 includes either all stacked holes 20J, all locking holes 22, a combination of stacked holes 20J and DCP slots 20I, or a combination of stacked holes 20J and combination holes 20. Additionally, in at least one embodiment, all of the holes of the cluster plate 10 have the same diameter such that they may all be utilized with screws, whether locking screws 30, non-locking screws 40 or self-drilling screws 70, all having the same diameter. While cluster plates 10 having specific hole combinations and diameters are described, the disclosure is not limited to such, and the cluster plates 10 may have any desired combination of the various holes described herein in any combination of diameters.

Figure 36A:
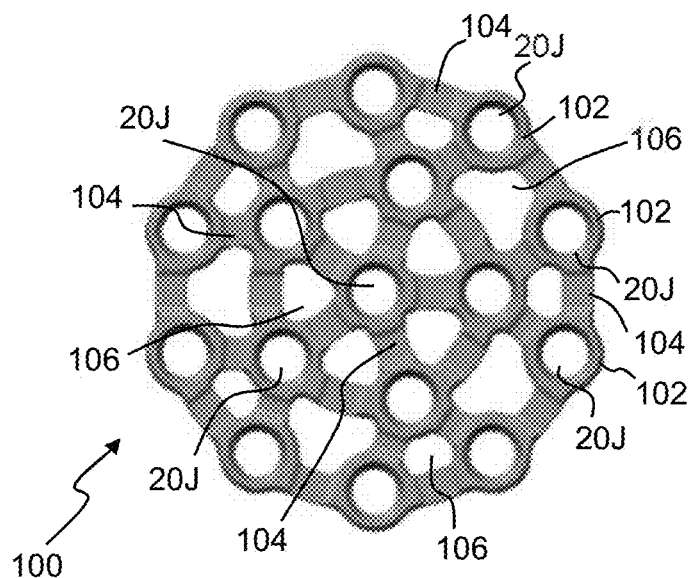
FIGS. 36A-36B show embodiments of illustrative mesh plates.
Figure 36B:
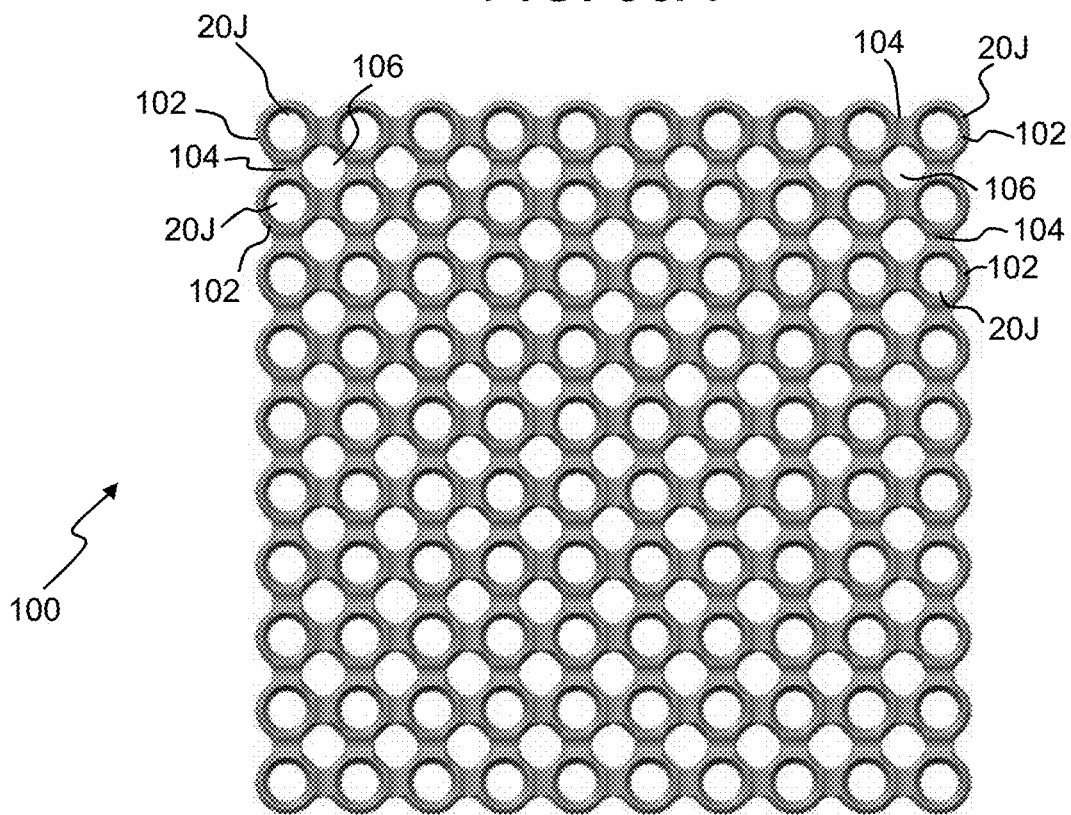

FIGS. 36A-36B provide embodiments of mesh plates 100, which may be available in a variety of sizes along with a variety of hole options. The mesh plates 100 do not include an elongate body but instead include only a clustered mesh of holes 20. Similar to the mesh head 90, the mesh plate 100 is defined by a plurality of holes 20, in the illustrated embodiment stacked holes 20J, each with a rim 102 thereabout. The rims 102 of adjacent holes 20 are interconnected to one another via bridge portions 104 with through spaces 106 also provided between groups of holes 20. The bridge portions 104 are preferably thinner than the rims 102. The thinner configuration of the bridge portions 104 along with the through spaces 106 allow the mesh plate 100 to be easily contoured. Additionally, the mesh plate 100 may be cut along the bridge portions 104 to shape the mesh plate 100 to achieve a desired shape or size. In the embodiment of FIG. 36A, the mesh plate 100 has a circular configuration with a central hole 20 and two bands of holes 20 thereabout. The bridge portions 104 interconnect the rings 102 within each band and also interconnect the bands to each other and with the ring 102 of the central hole 20. In the embodiment illustrated in FIG. 36B, the mesh plate 100 has a 10×10 hole arrangement defining a square configuration. The mesh plate 100 may have various numbers of holes 20 which may be arranged in various configurations including, for example, square, rectangular or round.

In at least one embodiment, the mesh plate 100 includes either all stacked holes 20J, all locking holes 22, or all non-locking holes 24. Additionally, in at least one embodiment, all of the holes of the mesh plate 100 have the same diameter such that they may all be utilized with screws, whether locking screws 30, non-locking screws 40 or self-drilling screws 70, all having the same diameter. While mesh plates 100 having specific hole combinations and diameters are described, the disclosure is not limited to such, and the mesh plates 100 may have any desired combination of the various holes described herein in any combination of diameters.

FIGS. 37A-37D relate to cloverleaf plates 10. The cloverleaf plates 10 have a three-pronged plate head profile. The cloverleaf plates 10 have an elongate portion extending along the longitudinal axis A of the plate 10 from the first end 12 of the body and one or more wings or extensions 80 extending from the elongate portion of the plate 10. As shown, the wings or extensions 80 may include three extensions 80; namely, a first extension 80 extending in along the longitudinal axis A of the plate 10, a second extension 80 extending at a first angle relative to the longitudinal axis A of the plate 10, and a third extension 80 extending at a second angle, mirroring the first angle, relative to the longitudinal axis A of the plate 10. These plates 10 are also available in a variety of lengths along with a variety of hole options. The cloverleaf plate 10 may be configured with a three-pronged plate head profile to capture fractures most often located near periarticular surfaces.

Figure 37A:
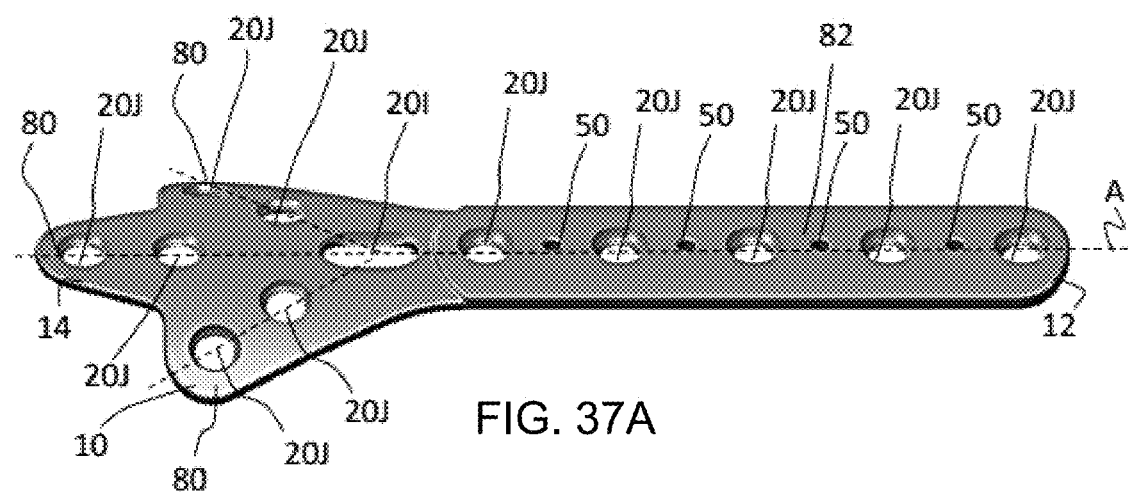
FIGS. 37A-37D relate to cloverleaf plates with alternative hole configurations.
Figure 37B:
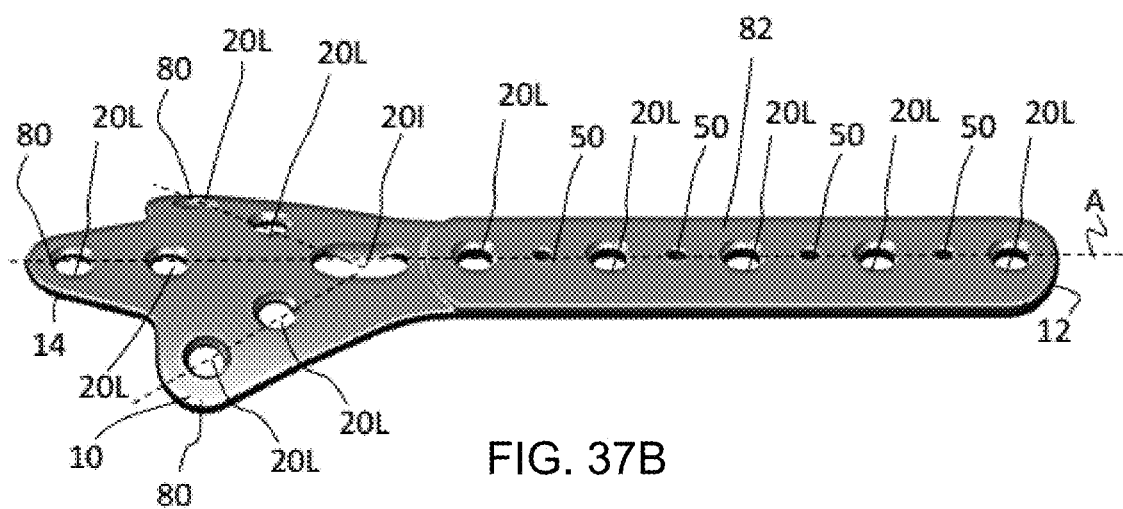
Figure 37C:
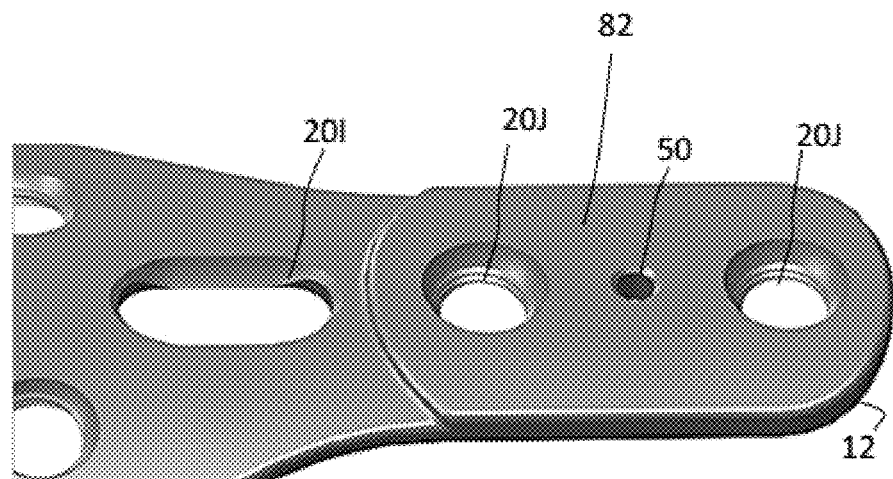
Figure 37D:
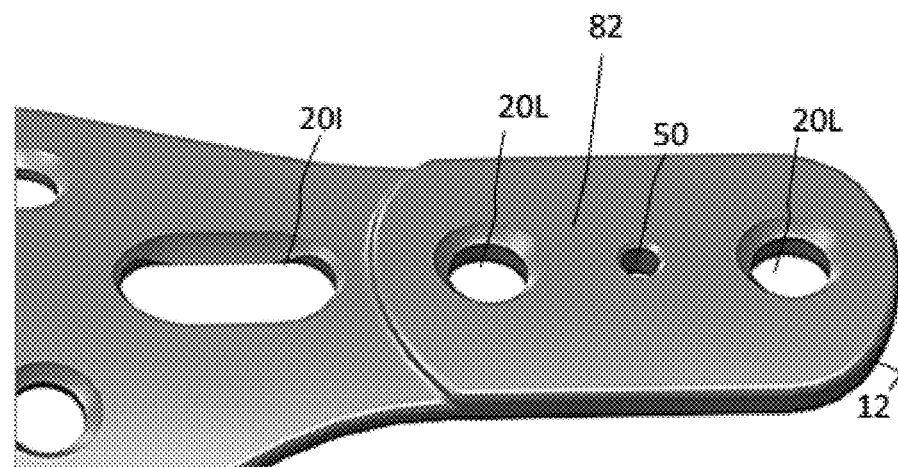

FIG. 37A depicts a cloverleaf plate 10 with a plurality of stacked holes 20J positioned along the elongate portion of the plate 10. As shown, the elongate portion of the plate 10 may include a raised portion 82, for example, with a greater thickness than the remainder of the plate 10. In other words, the extensions 80 may have a narrower or thinner thickness as compared to the raised portion 82 of the plate 10. The first extensions 80 may include a DCP slot 20I and two stacked holes 20J along the longitudinal axis A of the plate 10. Two additional stacked holes 20J may be positioned in the second extension 80, and two additional stacked holes 20J may be positioned in the third extension 80. FIG. 37B depicts another embodiment of the cloverleaf plate 10 with the same configuration as FIG. 37A but having the non-locking holes 20L replacing each of the stacked holes 20J. The cloverleaf plates 10 comprise a streamlined offering to treat a vast array of fracture patterns in various anatomical areas. The plate geometry is simplified by providing locking screw holes which accept locking screws at monoaxial trajectories as well as non-locking screws.

In at least one embodiment, the system includes a variety of self-tapping and self-drilling screws offered in stainless steel, titanium alloy, and cobalt chrome. An illustrative system may include, for example, 1.5 mm non-locking screws, locking screws, and self-drilling screws (6 mm-24 mm), 2.0 mm non-locking screws, locking screws, and self-drilling screws (6-40 mm), and 2.5 mm non-locking screws, locking screws, and self-drilling screws (6-80 mm).

Figure 38A:
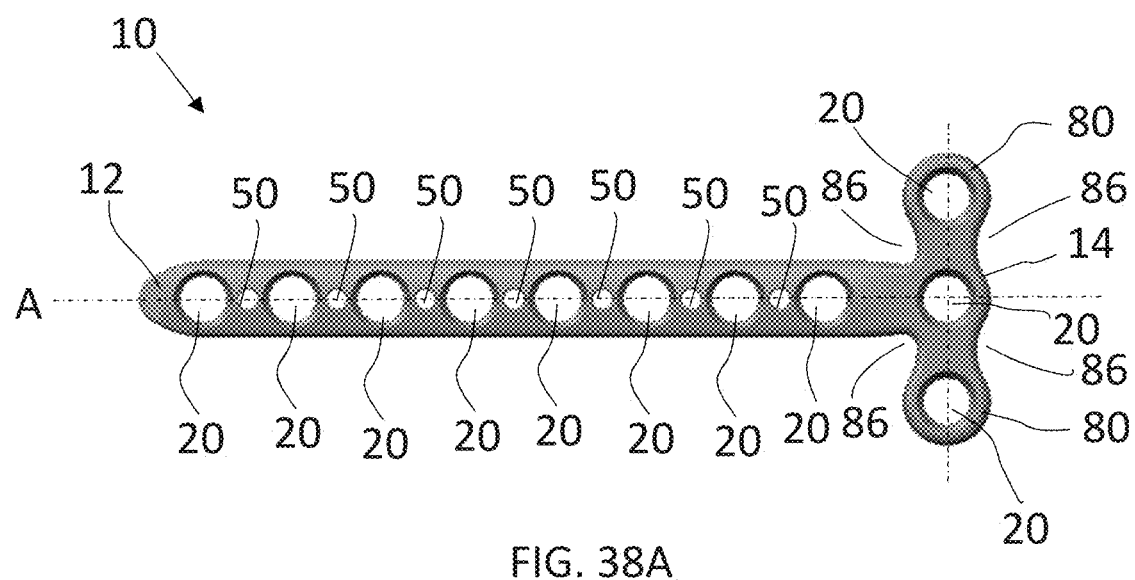
FIGS. 38A-38B show an embodiment of an alternative T-plate.
Figure 38B:
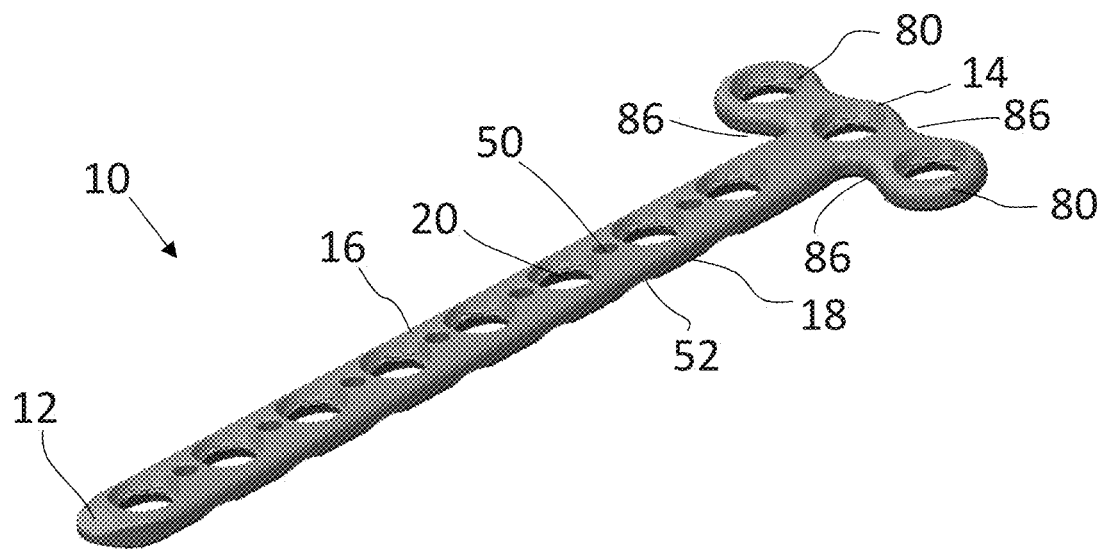

With reference to FIGS. 38A and 38B, an alternative plate 10 having a T-shaped design is shown. The T-plate 10 has a similar design to the T-plate shown in FIGS. 31F and 31G, but has a greater thickness along the length of the plate 10, and a shaft similar to the straight plate shown in FIG. 29G (e.g., without side relief cuts) for greater strength and rigidity. The plate 10 extends from first end 12 to second end 14 where extensions 80 extend in opposite directions creating a substantially T-shaped plate 10. A plurality of holes 20 are provided along the length of the plate 10 and within each of the extensions 80.

The holes 20 along the shaft of the plate 10 may be substantially aligned along the longitudinal axis A of the plate 10. The holes 20 in the extensions 80 may also be generally aligned along a common axis, perpendicular to the longitudinal axis A of the plate 10. The hole 20 near the second end 14 may be separated a distance from the next respective hole 20 along the length of the plate 10. At the intersection where the extensions 80 meet the shaft of the plate 10, one or more indentations 86 may be provided (for example, along the edges of the plate 10) such that the width of the plate 10 is narrowed relative to the width at the respective holes 20 and/or the overall width of the extensions 80. The narrowing may permit bending or contouring of the extensions 80 relative to the longitudinal axis A of the plate 10. The holes 20 provided along the plate 10 may include polyaxial holes, locking holes, non-locking holes, dynamic compression slots, or any of the holes described herein, and any combination thereof. The plate 10 may also include k-wire holes 50 and relief undercuts or conical cuts 52, for example, as shown and described for the plates in FIGS. 29A-29J.

The plates 10 may be available in different size and style options depending on the style of the holes 20 including polyaxial holes, locking holes, non-locking holes, dynamic compression slots, and any combination thereof. The T-Plates 10 provide for an optimized T-shape, with a 3-hole head design, for example, to provide enhanced screw density, strength and rigidity.

Figure 39A:
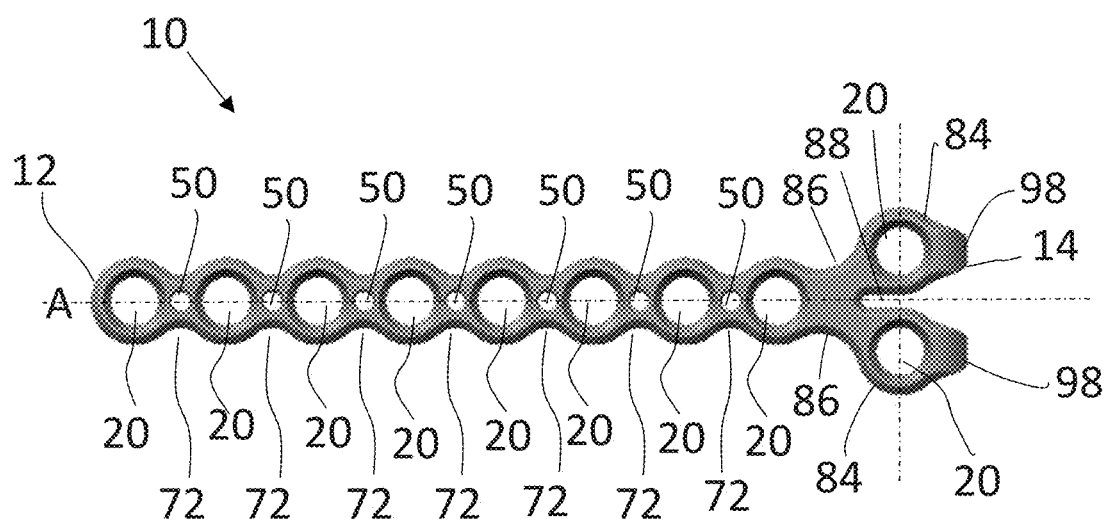
FIGS. 39A-39B show an embodiment of a tine plate.
Figure 39B:
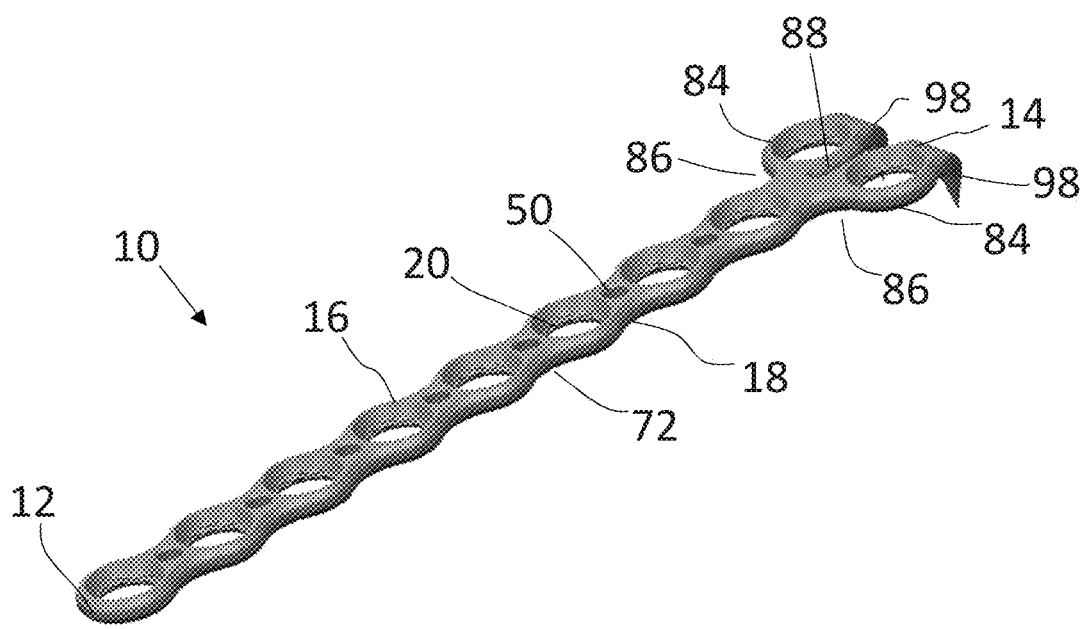

Turning now to FIGS. 39A and 39B, a tine plate 10 is shown. The tine plate 10 has a similar design to the condylar plate 10 shown in FIGS. 33A-33B, with a 2-hole ear-shaped head for enhanced contouring. The tine plate 10 has an elongate shaft portion extending along the longitudinal axis A of the plate 10 from the first end 12 of the body and a pair of ears 84 extending from the second end 14 of the body. The ears 84 are divided by a groove 88 separating the ears 84 and respective holes 20 therein. The groove 88 may extend along the longitudinal axis A of the plate 10. The groove 88 may extend a distance from the second end 14 greater than a distance of the holes 20 within the ears 84 from the second end 14. In other words, the groove 88 may be deeper than a radius of the screw holes 20 in the first and second ears 84. The groove 88 may also be narrow but expand in width proximate end 14. The groove 88 may have a first width proximate the elongate body and a second width, greater than the first width, proximate the first and second tines 98. As evident in FIG. 39A, the edges of the plate 10 may be contoured in these areas to mimic the radius of the holes 20.

The ears 84 terminate as sharp tines or hooks 98 on each head 84, thereby providing for two extra points of distal bone fixation. The hooks 98 may terminate as sharpened points. The hooks 98 may be bent at an angle relative to the remainder of the plate 10 and ears 84. For example, the hooks 98 may be provided at 90° relative the ears 84. The hooks 98 may also be provided at an angle less than 90° such that the tips of the hooks 98 are pointed back towards the first end 12 of the plate 10. Similar to the other embodiments described herein, the tine plate 10 may include holes 20, k-wire holes 50, and side relief cuts 72, thereby providing one or more scalloped edges along the length of the shaft of the plate 10. Narrowed portions of the scalloped edges may coincide with locations of the k-wire holes, for example. These tine plates 10 may be provided with different sizes and options of hole styles, e.g., polyaxial holes, locking holes, non-locking holes dynamic compression slots, and a combination of these.

The holes 20 in the ears 84 near the second end 14 may be separated a distance from the next respective hole 20 along the length of the plate 10. At the intersections where the ears 84 meet the shaft of the plate 10, one or more indentations 86 may be provided such that the width of the plate 10 is narrowed relative to the width at the respective holes 20 and/or the overall width of the ears 84. The narrowing may permit bending or contouring of the ears 84 relative to the plate 10. The 2-hole ear-shaped tine plate 10 may allow for enhanced contouring and the angled sharp hooks 98 may allow for extra points of distal bone fixation.

Figures 40A, 40B, 40C, 40D:
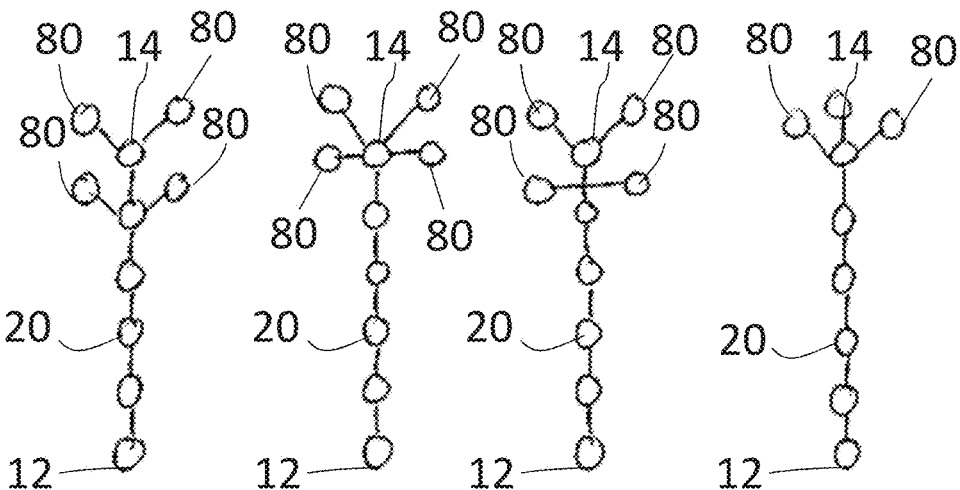
FIGS. 40A-40H show alternative embodiments of plates having different geometrical configurations.

Turning now to FIGS. 40A-40H, alternative configurations are shown for the plates 10 described herein, with the circles signifying the holes 20 and the line segments representing plate portions between the holes 20. It will be appreciated that the holes 20 may include any of the hole types described herein and the plates 10 may incorporate other features described herein, such as k-wire holes, scalloped or straight edges, undercuts, etc. In FIG. 40A, the plate features a double-Y head design. A plurality of extensions 80 are provided as two extensions 80 on each respective side of the plate 10. The upper and lower extensions 80 are aligned in parallel, and angled toward end 14, thereby providing a double Y-shaped configuration. FIG. 40B shows extensions 80 with a generally sideways k-shaped configuration. The upper extensions 80 angled toward end 14, thereby forming a generally y-shaped end. The lower extensions 80 extending generally perpendicular to the longitudinal axis A of the shaft of the plate 10 forming a generally t-shaped configuration. The extensions 80 may extend out at different angles from the outermost screw hole 20 for additional head fixation. FIG. 40C is similar to FIG. 40B with a generally sideways k-shape, but the perpendicular extensions 80 are moved to extend from the plate portion instead of from a hole segment. FIG. 40D is a plate that includes two angled extensions 80 positioned along the plate 10 (e.g., on the second opening 20) to create a 3-pronged head portion. The two independent y-shaped arms 80 extend from the second outermost screw hole 20, with an additional shaft hole 20 forming a third independent arm.

Figures 40E, 40F, 40G, 40H:
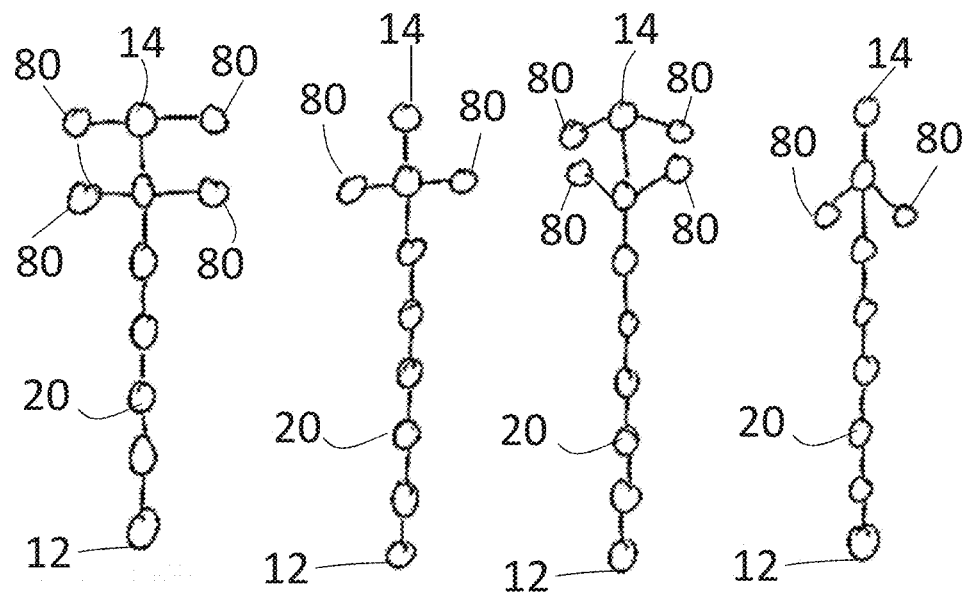

FIG. 40E creates an I-like configuration or sideways H-like configuration with the upper and lower extensions 80 each extending generally perpendicularly from the shaft portion and remaining parallel to one another. FIG. 40F provides a t-like or cross-shaped configuration with only first and second extensions 80 extending from plate 10 (e.g., from the second opening 20) generally perpendicular to the longitudinal axis of the plate 10. FIG. 40G features a diamond-like head design with upper extensions 80 generally angled downward towards end 12 and lower extensions 80 generally angled upward towards end 14 such that the distal ends of the upper and lower extensions 80 are closer to one another relative to the proximal portions attached to the shaft portion of the plate 10. The outermost and second outermost screw holes may each have two independent arms 80 extending outward forming a diamond shaped head. FIG. 40H is similar to FIG. 40D or FIG. 40F except that the extensions 80 are generally angled downward toward end 12 to form an inverse Y-shaped design. Although a number of variations are shown, it will be appreciated that the extensions 80 could connected at different locations along the plate 10, could be angled differently, could include more or less extensions 80, or could be otherwise configured.

Figure 41A:
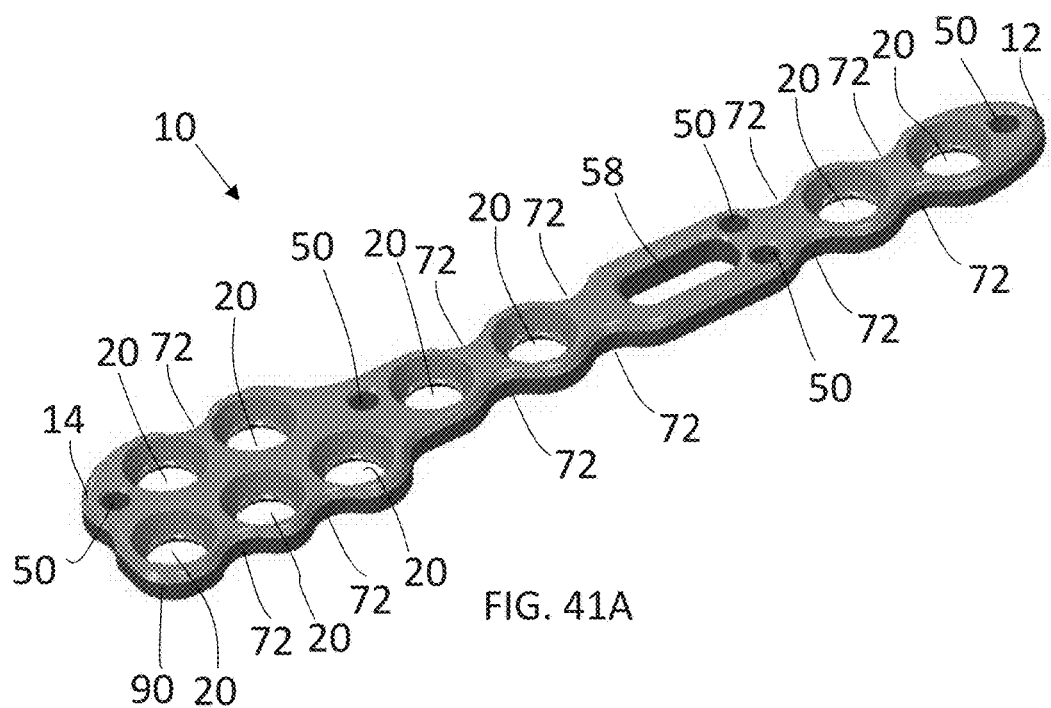
FIGS. 41A-41B show an alternative embodiment of a trauma plate which may be suitable, for example, for miniature bone fragments.
Figure 41B:
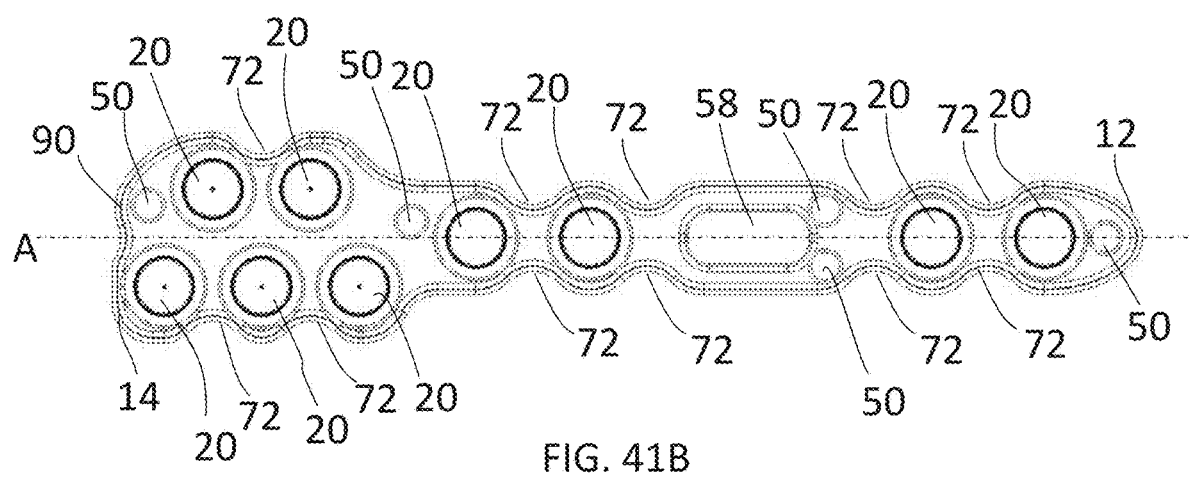

Turning now to FIGS. 41A and 41B, an alternative trauma plate 10 is provided, which may be suitable, for example, for securing smaller or miniature bone fragments. The plate 10 extends from a distal, first end 12 to a proximal, second end 14 along longitudinal axis A. The plate 10 may include an elongate body and the second end 14 may have an enlarged head portion 90 relative to the remainder of the plate 10. Similar to the other embodiments described herein, the plate 10 may include screw or fastener holes 20 (including polyaxial holes, locking holes, non-locking holes, etc.), k-wire holes 50, and side relief cuts 72. The elongate body may also include a sliding slot 58 in the form of an elongate opening having a length greater than its width configured to receive a fastener or screw to allow for positioning of the plate 10 during implantation. The sides of the slot 58 may be provided with one or more markings to indicate the amount of movement and/or position of the plate 10.

In the embodiment shown, the plate 10 includes two polyaxial openings 20 near the end 12 and two polyaxial openings 20 near the enlarged head 90, which are all aligned along the center longitudinal axis A of the plate 10. The elongate sliding slot 58 may be positioned between these two respective pairs of openings 20 along the axis A. The enlarged head 90 also include a plurality of openings 20. The openings 20 may be arranged such that three holes 20 are positioned along one axis to one side of the axis A and two holes 20 are positioned along another axis to the opposite side of the axis A. The three holes 20 and two holes 20 may also be offset relative to one another. The head 90 may be contoured with the relief cuts 72 such that the outer, edge surface of the plate 10 mimics the configurations of the openings 20. It will be appreciated that other configurations, numbers and types of openings may be provided to maximize fixation of the fractures.

The illustrated plates 10, 100 provide a comprehensive offering to treat a vast array of fracture patterns in various anatomical areas of varying sizes. The plates 10, 100 are capable of being used for both definitive, permanent fixation, as well as temporary or supplemental fixation in accordance with other systems. The specific plate styles afford the ability to accommodate multiple fracture patterns. The cluster plates accommodate optimal contouring in the head portion, while still maintaining strength and stability in the shaft portion of the plate by incorporating variable thickness between the two. The mesh plates are capable of being cut and contoured to accommodate an extremely expanded range of sizes, shapes, and contours. The large range of screw and plate sizes can accommodate multiple anatomies and anatomical regions.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A bone stabilization plate comprising:
   an elongate body extending from a first end to a second end along a longitudinal axis, the elongate body defining a plurality of screw holes;
   first and second ears extending from the second end of the elongate body, the first ear defining a first screw hole and the second ear defining a second screw hole therethrough, wherein the first and second ears are separated by a groove, wherein a deepest point of the groove is at a position closer to the first end than the first screw hole and the second screw hole; and
   a first tine extending from the first ear and a second tine extending from the second ear, the first and second tines each terminating at a sharp point,
   wherein the first ear and the second ear have an upper portion and a lower portion, the first screw hole positioned between the upper portion and the lower portion of the first ear and the second screw hole positioned between the upper portion and lower portion of the second screw hole, wherein the first tine is flush with the upper portion of the first ear and extends downward from a tip of the first screw hole at the second end and the second tine is flush with the upper portion of the second ear and extends downward from a tip of the second screw hole at the second end.

2. The bone stabilization plate of claim 1, wherein the first and second tines are bent at an angle relative to the longitudinal axis of the elongate body.

3. The bone stabilization plate of claim 1, wherein the first and second tines are bent at 90° relative to the longitudinal axis of the elongate body.

4. The bone stabilization plate of claim 1, wherein the groove is deeper than a radius of the screw holes in the first and second ears.

5. The bone stabilization plate of claim 1, wherein the groove has a first width proximate the elongate body and a second width, greater than the first width, proximate the first and second tines.

6. The bone stabilization plate of claim 1, wherein the elongate body has scalloped edges.

7. The bone stabilization plate of claim 6, wherein narrowed portions of the scalloped edges coincide with locations of a plurality of k-wire holes.

8. The bone stabilization plate of claim 1, wherein one or more indentations are provided where the first and second ears meet the elongate body such that a width of the plate is narrowed relative to a width of the first and second ears at the respective screw holes.

9. The bone stabilization plate of claim 1, wherein the screw holes are selected from a group consisting of locking holes, non-locking holes, polyaxial holes, dynamic compression slots, combination locking and non-locking holes, and stacked holes.

10. A bone stabilization plate comprising:
an elongate body extending from a first end to a second end along a longitudinal axis, the elongate body defining a plurality of screw holes;
first and second ears extending from the second end of the elongate body, the first ear defining a first screw hole and the second ear defining a second screw hole therethrough, the first and second ears are separated by a groove extending along the longitudinal axis wherein a deepest point of the groove is at a position closer to the first end than the first screw hole and the second screw hole; and
a first tine extending from the first ear and a second tine extending from the second ear, wherein the groove has a first width proximate the elongate body and a second width, greater than the first width, proximate the first and second tines,
wherein the first ear and the second ear have an upper portion and a lower portion, the first screw hole positioned between the upper portion and the lower portion of the first ear and the second screw hole positioned between the upper portion and lower portion of the second screw hole,
wherein the first tine is flush with the upper portion of the first ear and extends downward from a tip of the first screw hole at the second end and the second tine is flush with the upper portion of the second ear and extends downward from a tip of the second screw hole at the second end.

11. The bone stabilization plate of claim 10, wherein the first and second tines each terminate at a sharp point.

12. The bone stabilization plate of claim 10, wherein the first and second tines are bent at an angle relative to the longitudinal axis of the elongate body.

13. The bone stabilization plate of claim 10, wherein the first and second tines are bent at 90° relative to the longitudinal axis of the elongate body.

14. The bone stabilization plate of claim 10, wherein the groove is deeper than a radius of the screw holes in the first and second ears.

15. The bone stabilization plate of claim 10, wherein the elongate body has scalloped edges.

16. The bone stabilization plate of claim 15, wherein narrowed portions of the scalloped edges coincide with locations of a plurality of k-wire holes.

17. The bone stabilization plate of claim 10, wherein one or more indentations are provided where the first and second ears meet the elongate body such that a width of the plate is narrowed relative to a width of the first and second ears at the respective screw holes.

18. The bone stabilization plate of claim 10, wherein the screw holes are selected from a group consisting of locking holes, non-locking holes, polyaxial holes, dynamic compression slots, combination locking and non-locking holes, and stacked holes.

19. A bone stabilization plate comprising:
an elongate body extending from a first end to a second end along a longitudinal axis, the elongate body defining a plurality of screw holes therethrough, the elongate body having scalloped edges with narrowed portions between the plurality of screw holes;
first and second ears extending from the second end of the elongate body, the first and second ears being separated by a groove extending along the longitudinal axis, the first ear defining a first screw hole and the second ear defining a second screw hole, wherein a deepest point of the groove is at a position closer to the first end than the first screw hole and the second screw hole; and
a first tine extending from the first ear and a second tine extending from the second ear, the first and second tines each terminating at a sharp point, wherein the groove has a first width proximate the elongate body and a second width, greater than the first width, proximate the first and second tines,
wherein the first ear and the second ear have an upper portion and a lower portion, the first screw hole positioned between the upper portion and the lower portion of the first ear and the second screw hole positioned between the upper portion and lower portion of the second screw hole,
wherein the first tine is flush with the upper portion of the first ear and extends downward from a tip of the first screw hole at the second end and the second tine is flush with the upper portion of the second ear and extends downward from a tip of the second screw hole at the second end.

* * * * *